(12) United States Patent
Hara et al.

(10) Patent No.: US 11,618,742 B2
(45) Date of Patent: Apr. 4, 2023

(54) RADICAL POLYMERIZATION INITIATOR, COMPOSITION CONTAINING SAME, CURED PRODUCT OF COMPOSITION, PRODUCTION METHOD FOR CURED PRODUCT, AND COMPOUND

(71) Applicant: ADEKA CORPORATION, Tokyo (JP)

(72) Inventors: Kenji Hara, Tokyo (JP); Wataru Miyata, Tokyo (JP); Masatomi Irisawa, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 16/970,116

(22) PCT Filed: Feb. 15, 2019

(86) PCT No.: PCT/JP2019/005539
§ 371 (c)(1),
(2) Date: Aug. 14, 2020

(87) PCT Pub. No.: WO2019/160079
PCT Pub. Date: Aug. 22, 2019

(65) Prior Publication Data
US 2021/0107887 A1 Apr. 15, 2021

(30) Foreign Application Priority Data
Feb. 16, 2018 (JP) .............................. JP2018-026292

(51) Int. Cl.
*C08F 2/46* (2006.01)
*C08F 2/50* (2006.01)
(Continued)

(52) U.S. Cl.
CPC .............. *C07D 335/16* (2013.01); *C08F 2/44* (2013.01); *C08F 2/50* (2013.01); *C08F 16/06* (2013.01)

(58) Field of Classification Search
CPC ...... C08F 2/44; C08F 2/48; C08F 2/50; C08F 220/58; C08F 220/286; C08F 16/06; C07D 335/16
(Continued)

(56) References Cited

U.S. PATENT DOCUMENTS 4,101,668 A * 7/1978 Samour ................. C07D 333/68
514/419
2005/0288384 A1 12/2005 Kanke et al.
(Continued)

FOREIGN PATENT DOCUMENTS

EP 2 592 074 A1 5/2013
GB 1 458 185 12/1976
(Continued)

OTHER PUBLICATIONS

Mayer, Derivate der Thiosalicylsaure und des Thioxanthone, Feb. 4, 1910, Aus dem Chem. Laboratorium des physikalischen Voreins und der Akademie zu Frankfort am Main (Year: 1910).*
Ishikawa, JP 2004-195664 Machine Translation, Jul. 15, 2004 (Year: 2004).*
Jiang et al, Photoirradiation-generated radicals in two-component supramolecular gel for polymerization, 2018, Soft Matter, 14, 2295-2300 (Year: 2018).*
Esen et al., "One-Component Thioxanthone Acetic Acid Derivative Photoinitiator for Free Radical Polymerization," Photochemistry and Photobiology, vol. 90, 2014, pp. 463-469.
International Search Report (PCT/ISA/210) issued in PCT/JP2019/005539, dated May 21, 2019.
(Continued)

*Primary Examiner* — Jessica Whiteley
(74) *Attorney, Agent, or Firm* — Birch, Stewart, Kolasch & Birch, LLP

(57) ABSTRACT

Provided are: a radical polymerization initiator which has excellent sensitivity and solubility in water; a composition containing the same; a cured product of the composition; a method of producing the cured product; and a compound. The radical polymerization initiator contains a compound represented by Formula (A) below (wherein $Z^1$ represents a direct bond or the like; $Z^2$ represents —$C(R^{102})_2$— or the like; $R^1$ to $R^8$ each represent a hydrogen atom or the like, or a group containing a salt-forming group, which is represented by Formula (B1) below (wherein $L_1$ represents a direct bond or the like, B represents an acidic group salt or the like, b represents 1 to 10, and the asterisk (*) represents a binding site), at least one of $R^1$ to $R^8$ is the group containing a salt-forming group; $R^{101}$ and the like each represent a hydrogen atom or the like; one or more hydrogen atoms in the alkyl group and the like used as $R^1$ to $R^8$ and the like are optionally substituted with an ethylenically unsaturated group or the like; one or more methylene groups in $R^1$ to $R^8$ and the like are optionally substituted with a double bond or the like; adjacent groups such as $R^1$ and $R^2$ are optionally bound together to, form a ring and optionally form a fused ring with a benzene ring in Formula (A); and represents a hydrogen atom or the like).

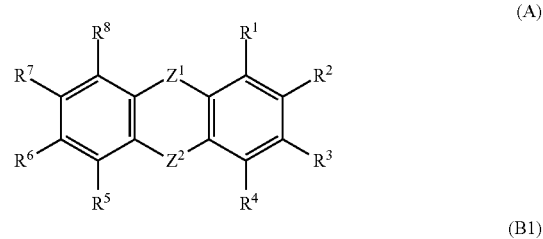

16 Claims, No Drawings

(51) Int. Cl.
*C08G 61/04* (2006.01)
*C07D 335/16* (2006.01)
*C08F 2/44* (2006.01)
*C08F 16/06* (2006.01)

(58) Field of Classification Search
USPC .......... 522/53, 49, 6, 71, 1, 189, 184; 520/1
See application file for complete search history.

(56) References Cited

U.S. PATENT DOCUMENTS

| 2012/0142806 A1 | 6/2012 | Motofuji et al. |
| 2014/0045966 A1 | 2/2014 | Motofuji et al. |
| 2015/0159032 A1 | 6/2015 | Yofu |

FOREIGN PATENT DOCUMENTS

| JP | 49-92072 A | | 9/1974 |
| JP | 2000-159621 A | | 6/2000 |
| JP | 2001-206903 A | | 7/2001 |
| JP | 2004-195664 A | | 7/2004 |
| JP | 2004195664 | * | 7/2004 |
| JP | 2005-289961 A | | 10/2005 |
| JP | 2005-307198 A | | 11/2005 |
| JP | 2012-7070 A | | 1/2012 |
| JP | 2013-530994 A | | 8/2013 |
| JP | 2017-3911 A | | 1/2017 |
| WO | WO 2010/143560 A1 | | 12/2010 |
| WO | WO 2012/121235 A1 | | 9/2012 |
| WO | WO 2014/050551 A1 | | 4/2014 |

OTHER PUBLICATIONS

Karaca et al., "Preparation of hydrogels by photopolymerization of acrylates in the presence of Type I and one-component Type II photoinitiators," Journal of Photochemistry and Photobiology A: Chemistry, vol. 209, 2010, pp. 1-6.

PubChem, "9-oxo-9H-thioxanthene-4carboxylic acid, sodium salt," Version 3, Dec. 19, 2011, PubChem SID: 569068, 2 pages.

Written Opinion of the International Searching Authority (PCT/ISA/237) issued in PCT/JP2019/005539, dated May 21, 2019.

Yilmaz et al., "Counteranion Sensitization Approach to Photoinitiated Free Radical Polymerization," Macromolecules, vol. 45, 2012, pp. 2219-2224.

* cited by examiner

RADICAL POLYMERIZATION INITIATOR, COMPOSITION CONTAINING SAME, CURED PRODUCT OF COMPOSITION, PRODUCTION METHOD FOR CURED PRODUCT, AND COMPOUND

TECHNICAL FIELD

The present invention relates to: a radical polymerization initiator; a composition containing the same; a cured product of the composition; a method of producing the cured product; and a novel compound. More particularly, the present invention relates to: a radical polymerization initiator which has excellent sensitivity and solubility in water; a composition containing the same; a cured product of the composition; a method of producing the cured product; and a compound.

BACKGROUND ART

Water-soluble compositions are used in a variety of applications, such as paints, inks, adhesives, and optical films. Focusing attention on water-soluble initiators of water-soluble compositions, Patent Document 1 proposes a photopolymerization initiator having a betaine structure; Patent Document 2 proposes an α-aminoacetophenone having a morpholine structure; and Patent Document 3 proposes an acylphosphine oxide compound.

RELATED ART DOCUMENTS

Patent Documents

[Patent Document 1] WO 2014/050551
[Patent Document 2] JP2012-007070A [Patent Document 3] JP2000-159621A

SUMMARY OF THE INVENTION

Problems to be Solved by the Invention

The initiators proposed in the above-described Patent Documents are soluble in water; however, they are poor in sensitivity and thus have a problem of causing defects, such as insufficient curing when a color material such as a pigment is incorporated, and insufficient curing of a deep part of a composition (a part deep from the surface layer in the cross-sectional direction).

In view of the above-described problems, an object of the present invention is to provide a radical polymerization initiator having excellent sensitivity and solubility in water, a composition containing the same, a cured product of the composition, a method of producing the cured product, and a compound.

Means for Solving the Problems

The present inventors intensively studied to solve the above-described problems and consequently discovered that a compound having a prescribed tricyclic structure and a group containing a salt-forming group can function as a radical polymerization initiator excellent in sensitivity and solubility in water, thereby completing the present invention.

That is, a radical polymerization initiator of the present invention is characterized by containing a compound represented by the following Formula (A):

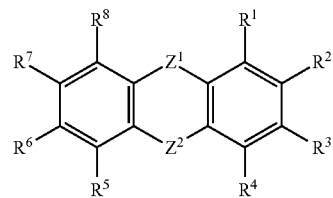

(wherein,
$Z^1$ represents a direct bond, $NR^{101}$—, —O—, —S—, —SO—, or —CO—;
$Z^2$ represents —C($R^{102}$)$_2$—, —$NR^{101}$—, —O—, —S—, —SO—, or —CO—;
$R^1$, $R^2$, $R^3$, $R^4$, $R^5$, $R^6$, $R^7$ and $R^8$ each independently represent a hydrogen atom, CN, $NO_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group represented by the following Formula (B1):

$$*\text{-}L_1\text{-}(B)_b \tag{B1}$$

(wherein,
$L_1$ represents a direct bond or a (b+1)-valent linking group,
B represents an acidic group salt or a basic group salt,
b represents an integer of 1 to 10, and
the asterisk (*) represents a site of binding with a benzene ring);
at least one of $R^1$, $R^2$, $R^3$, $R^4$, $R^5$, $R^6$, $R^7$ and $R^8$ is the group containing a salt-forming group;
$R^{101}$ and $R^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms;
one or more hydrogen atoms in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;
one or more methylene groups in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another;

adjacent groups of R$^1$ and R$^2$, R$^2$ and R$^3$, R$^3$ and R$^4$, R$^5$ and R$^6$, R$^6$ and R$^7$, and R$^7$ and R$^8$ are optionally bound together to form a ring, and optionally form a fused ring with a benzene ring constituting a three-membered ring in Formula (A); and R' represents a hydrogen atom or an alkyl group having 1 to 8 carbon atoms).

In the radical polymerization initiator of the present invention, the above-described compound preferably has a maximum absorption wavelength of 380 nm or longer in a range of 300 nm to 600 nm. Further, in the radical polymerization initiator of the present invention, a combination of Z$^1$ and Z$^2$ is preferably a combination of —S— and —CO—. Still further, in the radical polymerization initiator of the present invention, it is preferred that B be an acidic group salt and L$_1$ be a direct bond. Yet still further, in the radical polymerization initiator of the present invention, it is preferred that B be an acidic group salt and an anionic group constituting the acidic group salt be a carboxylic acid ion group. In the radical polymerization initiator of the present invention, it is preferred that B be an acidic group salt and a cationic component constituting the acidic group salt be an alkali metal ion, an alkaline earth metal ion, or an amine cation. In the radical polymerization initiator of the present invention, the above-described compound preferably has a solubility of 0.5 parts by mass in 100 parts by mass of water. The radical polymerization initiator of the present invention preferably further contains a compound represented by the following Formula (I):

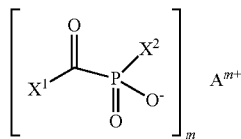

(wherein,

X$^1$ represents an aryl group having 6 to 15 carbon atoms which optionally has a substituent;

X$^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms which optionally has a substituent;

A$^{m+}$ represents an m-valent cationic component;

m represents a number of 1 to 3;

one or more hydrogen atoms in the aryl group used as X$^1$ and X$^2$ and the alkyl group or alkoxy group used as X$^2$ are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;

one or more methylene groups in the aryl group used as X$^1$ and X$^2$ and the alkyl group or alkoxy group used as X$^2$ are optionally substituted with a carbon-carbon double bond, —O—, —S—, —CO—, —O—CO—, —OO—O—, —OCO—O—, —O—COO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another; and R' represents a hydrogen atom or an alkyl group having 1 to 8 carbon atoms).

A composition of the present invention is characterized by containing:

a compound represented by the following Formula (A):

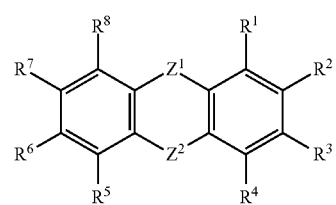

(wherein,

Z$^1$ represents a direct bond, NR$^{101}$—, —O—, —S—, —SO—, or —CO—;

Z$^2$ represents —C(R$^{102}$)$_2$—, —NR$^{101}$—, —O—, —S—, —SO—, or —CO—;

R$^1$, R$^2$, R$^3$, R$^4$, R$^5$, R$^6$, R$^7$ and R$^8$ each independently represent a hydrogen atom, CN, NO$_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group, which is represented by the following Formula (B1):

$$*\text{-}L_1\text{\textemdash}(B)_b$$ (B1)

(wherein,

L$_1$ represents a direct bond or a (b+1)-valent linking group,

B represents an acidic group salt or a basic group salt, b represents an integer of 1 to 10, and the asterisk (*) represents a site of binding with a benzene ring);

at least one of R$^1$, R$^2$, R$^3$, R$^4$, R$^5$, R$^6$, R$^7$ and R$^8$ is the group containing a salt-forming group;

R$^{101}$ and R$^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms;

one or more hydrogen atoms in the alkyl group, the aryl group optionally substituted with an alkyl group, the arylalkyl group optionally substituted with an alkyl group, and the heterocycle-containing group, which groups are used as R$^1$, R$^2$, R$^3$, R$^4$, R$^5$, R$^6$, R$^7$ and R$^8$ and R$^{101}$ and R$^{102}$, are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;

one or more methylene groups in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO₂—, or a combination of groups selected from the above such that oxygen atoms are not arranged adjacent to one another;

adjacent groups of $R^1$ and $R^2$, $R^2$ and $R^3$, $R^3$ and $R^4$, $R^5$ and $R^6$, $R^6$ and $R^7$, and $R^7$ and $R^8$ are optionally bound together to form a ring, and optionally form a fused ring with a benzene ring constituting a three-membered ring in Formula (A); and R' represents a hydrogen atom or an alkyl group having 1 to 8 carbon atoms); and a radical polymerizable compound.

It is preferred that the composition of the present invention further contain a solvent, and that the solvent contain water. The composition of the present invention preferably further contains a compound represented by the following Formula (1):

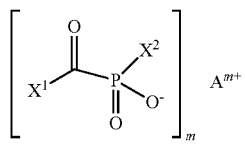

(wherein, $X^1$ represents an aryl group having 6 to 15 carbon atoms which optionally has a substituent;

$X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms which optionally has a substituent;

$A^{m+}$ represents an m-valent cationic component;

m represents a number of 1 to 3;

one or more hydrogen atoms in the aryl group used as $X^1$ and $X^2$ and the alkyl group or alkoxy group used as $X^2$ are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;

one or more methylene groups in the aryl group used as $X^1$ and $X^2$ and the alkyl group or alkoxy group used as $X^2$ are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO₂—, or a combination of groups selected from the above such that oxygen atoms are not arranged adjacent to one another; and R' represents a hydrogen atom or an alkyl group having 1 to 8 carbon atoms).

A cured product of the present invention is characterized by containing the composition of the present invention.

A method of producing the cured product according to the present invention is characterized by including a step of irradiating the composition of the present invention with light.

A compound of the present invention is characterized by being represented by the following Formula (A):

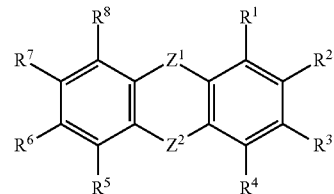

(wherein, $Z^1$ represents a direct bond, —NR¹⁰¹—, —O—, —S—, —SO—, or —CO—;

$Z^2$ represents —C(R¹⁰²)₂—, —NR¹⁰¹—, —O—, —S—, —SO—, or —CO—;

$R^1$, $R^2$, $R^3$, $R^4$, R, $R^6$, $R^7$ and $R^8$ each independently represent a hydrogen atom, CN, NO₂, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group, which is represented by the following Formula (B1):

*-L₁-(-B)_b    (B1)

(wherein, $L_1$ represents a direct bond or a (b+1)-valent linking group,

B represents an acidic group salt or a basic group salt, b represents an integer of 1 to 10, and the asterisk (*) represents a site of binding with a benzene ring);

at least one of $R^1$, $R^2$, $R^3$, $R^4$, $R^5$, $R^6$, $R^7$ and $R^8$ is the group containing a salt-forming $R^4$, group;

$R^{101}$ and $R^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms;

one or more hydrogen atoms in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{t2}$, are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;

one or more methylene groups in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another;

adjacent groups of $R^1$ and $R^2$, $R^2$ and $R^3$, $R^3$ and $R^4$, $R^5$ and $R^6$, $R^6$ and $R^7$, and $R^7$ and $R^8$ are optionally bound together to form a ring, and optionally form a fused ring with a benzene ring constituting a three-membered ring in Formula (A); and R' represents a hydrogen atom or an alkyl group having 1 to 8 carbon atoms).

In the compound of the present invention, it is preferred that a combination of $Z^1$ and $Z^2$ be a combination of —S— and —CO—; that B be an acidic group salt; that an anionic group constituting the acidic group salt be a carboxylic acid ion group; and that $L_1$ be a direct bond.

Effects of the Invention

According to the present invention, a radical polymerization initiator which has excellent sensitivity and solubility in water, a composition containing the same, a cured product of the composition, a method of producing the cured product, and a compound can be provided. In other words, the radical polymerization initiator of the present invention exhibits excellent sensitivity and solubility in water by containing a compound having a structure represented by the above-described Formula (A) (this compound is hereinafter also referred to as "compound A").

In addition, the compound A has superior sensitivity by controlling the maximum absorption wavelength in a range of 300 nm to 600 nm to be 380 nm or longer. Further, the compound A has superior sensitivity and solubility in water when a combination of $Z^1$ and $Z^2$ is a combination of —S— and —CO—. Still further, the compound A has superior sensitivity when B and $L_1$ are an acidic group salt and a direct bond, respectively. Yet still further, the compound A has superior sensitivity when B is an acidic group salt and an anionic group constituting the acidic group salt is a carboxylic acid ion group. Yet still further, the compound A has superior solubility in water when B is an acidic group salt and a cationic component constituting the acidic group salt is an alkali metal ion, an alkaline earth metal ion or an amine cation. Yet still further, the radical polymerization initiator of the present invention has superior solubility in water when the compound A has a solubility of not less than 0.5 parts by mass in 100 parts by mass of water. Yet still further, the radical polymerizable compound of the present invention has superior sensitivity by further containing a compound represented by Formula (I).

According to the composition of the present invention, because of the use of the above-described compound A, a composition having excellent sensitivity and a low organic solvent content can be easily obtained. The composition of the present invention contains a solvent, and this solvent contains water; therefore, it is easy to attain excellent sensitivity and a low organic solvent content. In addition, the composition of the present invention attains superior sensitivity by containing a compound represented by the above-described Formula (I).

According to the cured product of the present invention, curing is easily performed, and the generation of an organic solvent is limited.

According the method of producing the cured product according to the present invention, the use of the composition of the present invention enables to easily obtain a cured product with limited generation of an organic solvent.

The compound of the present invention can be used as a radical polymerization initiator which has excellent sensitivity and solubility in water.

In the compound of the present invention, it is preferred that a combination of $Z^1$ and $Z^2$ be a combination of —S— and —CO—, B be an acidic group salt, an anionic group constituting the acidic group salt be a carboxylic acid ion group, and $L_1$ be a direct bond. By adopting this structure, the compound of the present invention can be easily used as a radical polymerization initiator which has superior sensitivity and solubility in water.

MODE FOR CARRYING OUT THE INVENTION

The present invention relates to: a radical polymerization initiator which has excellent sensitivity and solubility in water; a composition containing the same; a cured product of the composition; a method of producing the cured product; and a compound. Embodiments of the present invention will now be described in detail.

A. Compound

First, the compound of the present invention will be described.

The compound of the present invention is represented by the following Formula (A):

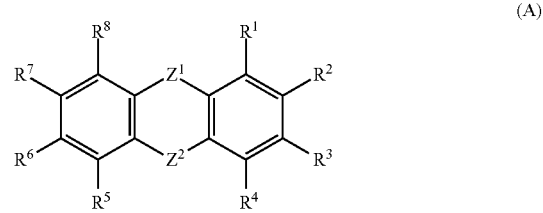

(A)

In Formula (A), $Z^1$ represents a direct bond, —NR$^{101}$—, —O—, —S—, —SO—, or —CO—; $Z^2$ represents —C(R$^{102}$)$_2$—, —NR$^{101}$—, —O—, —S—, —SO—, or —CO—; $R^1$ to $R^8$ each independently represent a hydrogen atom, CN, NO$_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group, which is represented by the below-described Formula (B1), with at least one of which $R^1$ to $R^8$ being the group containing a salt-forming group; and $R^{101}$ and $R^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms:

*-L$_1$-(-B)$_b$  (B1)

In Formula (B), $L_1$ represents a direct bond or a (b+1)-valent linking group; B represents an acidic group salt or a basic group salt; b represents an integer of 1 to 10; and the asterisk (*) represents a site of binding with a benzene ring.

The compound A of the present invention has the above-described structure and, therefore, can be used as a radical polymerization initiator which has excellent sensitivity and solubility in water. The reasons why the above-described structure allows the compound A of the present invention to be used as a radical polymerization initiator which has excellent sensitivity and solubility in water are presumed as follows.

That is, the compound A of the present invention is, by having the tricyclic structure represented by Formula (A), capable of absorbing light in a broad wavelength range including long-wavelength light. For example, when the combination of $Z^1$ and $Z^2$ is a combination of —S— and —CO— the compound A of the present invention functions as a radical polymerization initiator that is capable of absorbing light in a broad wavelength range including light having a long wavelength of 360 nm or longer.

In addition, for example, by adopting a substituent that forms a conjugated structure with the tricyclic structure and selecting a component capable of absorbing light in a long-wavelength range as a cationic component or anionic component that forms a salt with an anionic group or cationic group contained in the salt-forming group, the compound A of the present invention is easily made capable of absorbing light in a long wavelength range than the tricyclic structure by itself.

Because of the above, the compound A of the present invention is capable of absorbing light in a broad wavelength range and has excellent sensitivity. In addition, the compound A of the present invention exhibits excellent solubility in water by having a group containing a salt-forming group as a substituent of its tricyclic structure. Accordingly, the compound A of the present invention can be used as a radical polymerization initiator which has excellent sensitivity and solubility in water.

Moreover, by being capable of absorbing light in a long-wavelength range, the compound A of the present invention has excellent depth curability in that it allows even a deep part of a composition to be cured in a stable manner. This depth curability makes the compound A of the present invention particularly useful for, for example, curing a thick composition, or curing a colorant-containing composition such as a water-soluble photocurable ink. Furthermore, by having excellent solubility in water, the compound A of the present invention also exhibits excellent compatibility with water-soluble resins, such as radical polymerizable compounds and resin components that contain a hydrophilic group, such as a carboxyl group, a hydroxy group, an acrylamide group or an ester group. Consequently, the compound A of the present invention can also be suitably used in, for example, a solvent-free composition, when used in combination with a water-soluble resin.

The compound A of the present invention will now be described in detail.

1. Group Containing Salt-Forming Group

The compound A of the present invention has a group containing a salt-forming group, which is represented by the above-described Formula (B1). The salt-forming group represented by B in Formula (B1) is hereinafter referred to as "salt-forming group B".

(1) Salt-Forming Group B

The salt-forming group B used in Formula (B1) is an acidic group salt or a basic group salt. In the compound of the present invention, the salt-forming group B is preferably an acidic group salt. This is because, with the salt-forming group B being an acidic group salt, the compound A of the present invention can be used as a radical polymerization initiator having superior sensitivity. The acidic group salt contains an anionic group bound to $L_1$, and a cationic component forming a salt with the anionic group. Meanwhile, the basic group salt contains a cationic group bound to $L_1$, and an anionic component forming a salt with the cationic group. The valence of an anion and that of a cation in the salt-forming group B may be the same. For example, when the salt-forming group B is an acidic group salt and the anionic group is a divalent anion, the salt-forming group B may contain two monovalent cationic components or a single divalent cationic component.

(1-1) Acidic Group Salt

The anionic group constituting the acidic group salt may be any anionic group as long as it can impart the compound A with the desired sensitivity and solubility in water and, for example, a phosphoric acid ion group, a carboxylic acid ion group, a sulfonic acid ion group, a phosphate ion group, a sulfate ion group, a nitrate ion group, a phosphorous acid ion group, a phosphonic acid ion group, a phosphinic acid ion group, and a sulfinic acid ion group can be used. Thereamong, the anionic group is preferably a carboxylic acid ion group (—COO$^-$) or a sulfonic acid ion group (—SO$_3^-$), particularly preferably a carboxylic acid ion group (—COO$^-$). This is because such an anionic group allows the compound A of the present invention to be used as a radical polymerization initiator having superior sensitivity.

The cationic component forming a salt with the anionic group may be any cationic component as long as it can impart the compound A with the desired sensitivity and solubility in water. The cationic component may be an inorganic ion or an organic ion.

Examples of the inorganic ion include alkali metal ions and alkaline earth metal ions.

Examples of the organic ion include a tertiary sulfonium cation, a tertiary oxonium cation, a quaternary phosphonium cation, an amine cation, and a tertiary carbocation.

In the compound A of the present invention, from the standpoint of the ease of synthesis, the cationic component is preferably an alkali metal ion, an alkaline earth metal ion, or an amine cation, more preferably an alkali metal ion or an amine cation. This is because, with the cationic component being any of these ions, the compound A has superior solubility in water and storage stability.

Examples of the alkali metal ion include a lithium ion, a sodium ion, a potassium ion, a rubidium ion, and a cesium ion. Thereamong, the alkali metal ion is preferably a potassium ion. This is because it allows the compound A of the present invention to be used as a radical polymerization initiator having superior solubility in water.

Examples of the alkaline earth metal ion include a magnesium ion and a calcium ion.

The amine cation may be any cation as long as it has a positive charge on a nitrogen atom, and any of an ammonium cation (N$^+$H$_4$) and primary to quaternary ammonium cations can be used. Thereamong, the amine cation is preferably a tertiary ammonium cation or a quaternary ammonium cation, particularly preferably a tertiary ammonium cation. This is because, with the amine cation being any of these cations, the compound A of the present invention has superior solubility in water.

As the tertiary ammonium cation, for example, a cation represented by Formula (C3) below (hereinafter, also referred to as "cation C3") can be used. It is noted here that, when plural ammonium cations are contained in one molecule, the term "ammonium cation" may correspond to an ammonium cation having the largest number of substitutions. For example, a cation that contains a tertiary ammonium cation and at least either one of a secondary ammonium cation and a primary ammonium cation in one molecule corresponds to a tertiary ammonium cation.

$$N^+HY^1Y^2Y^3 \quad (C3)$$

In Formula (C3), $Y^1$, $Y^2$ and $Y^3$ each independently represent a hydroxy group, an alkyl group having 1 to 6 carbon atoms, an alkenyl group having 2 to 6 carbon atoms, an aryl group having 6 to 15 carbon atoms, or an arylalkyl group having 7 to 13 carbon atoms.

The hydrogen atoms in the groups represented by $Y^1$, $Y^2$ and $Y^3$ may each be substituted with a hydroxy group; the methylene groups in the groups represented by $Y^1$, $Y^2$ and $Y^3$ may each be substituted with an oxygen atom or and two or more of $Y^1$, $Y^2$ and $Y^3$ may be bound together to form a ring.

Examples of the alkyl group having 1 to 6 carbon atoms that is used as $Y^1$ to $Y^3$ include methyl, ethyl, propyl, isopropyl, butyl, isobutyl, s-butyl, t-butyl, amyl, isoamyl, t-amyl, and hexyl.

Examples of the alkenyl group having 2 to 6 carbon atoms that is used as $Y^1$ to $Y^3$ include vinyl, ethylene, 2-propenyl, 3-butenyl, 2-butenyl, 4-pentenyl, 3-pentenyl, 2-hexenyl, 3-hexenyl, and 5-hexenyl.

Examples of the aryl group having 6 to 15 carbon atoms that is used as $Y^1$ to $Y^3$ include phenyl, trimethylphenyl, tolyl, xylyl, naphthyl, and anthryl.

The arylalkyl group having 7 to 13 carbon atoms used as $Y^1$ to $Y^3$ means a group having 7 to 13 carbon atoms that is obtained by substituting a hydrogen atom of an alkyl group with an aryl group. Examples thereof include benzyl, α-methylbenzyl, α,α-dimethylbenzyl, phenylethyl, and naphthylpropyl.

In the compound A of the present invention, it is preferred that two or more of $Y^1$ to $Y^3$ be bound together to form a ring. This is because it allows the compound A of the present invention to have superior solubility in water and sensitivity. It is noted here that the below-described compound Nos. A1 to A14 represent examples of the cation C3 in which two or more of $Y^1$ to $Y^3$ are bound together to form a ring.

In the compound A of the present invention, it is preferred that one or more hydrogen atoms of $Y^1$ to $Y^3$ be substituted with hydroxy groups. This is because it allows the compound A of the present invention to have superior solubility in water. It is noted here that the below-described compound Nos. A5, A6 and A15 to A34 represent examples of the cation C3 in which one or more hydrogen atoms of $Y^1$ to $Y^3$ are substituted with hydroxy groups.

More specific examples of the cation C3 include the following compound Nos. A1 to A34.

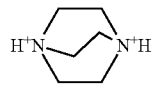

Compound No. A1

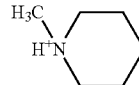

Compound No. A2

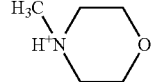

Compound No. A3

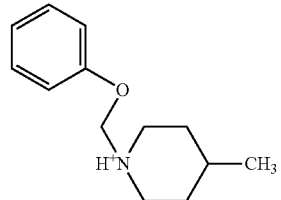

Compound No. A4

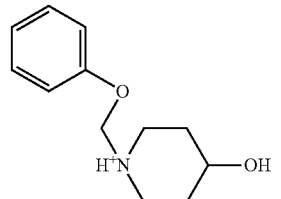

Compound No. A5

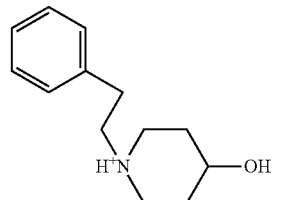

Compound No. A6

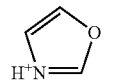

Compound No. A7

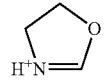

Compound No. A8

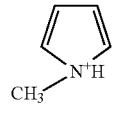

Compound No. A9

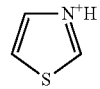

Compound No. A10

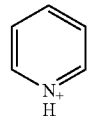

Compound No. A11

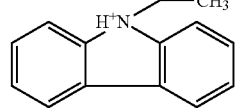

Compound No. A12

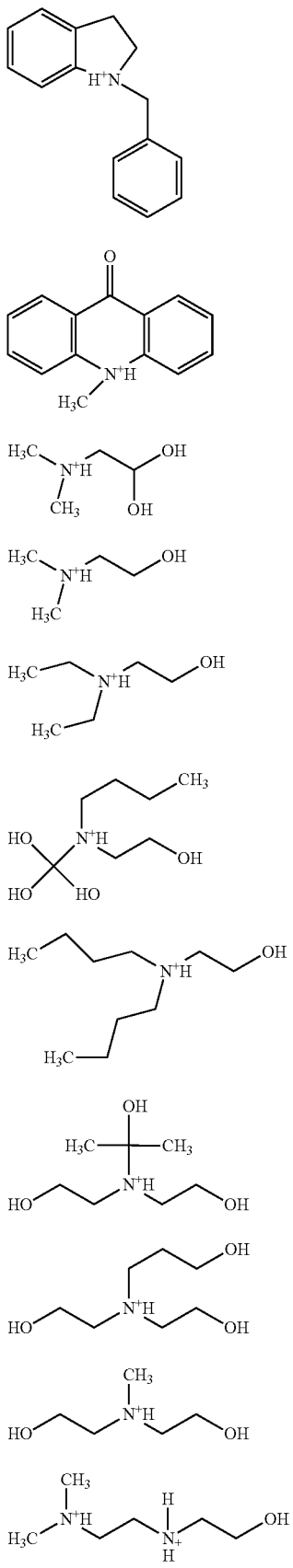
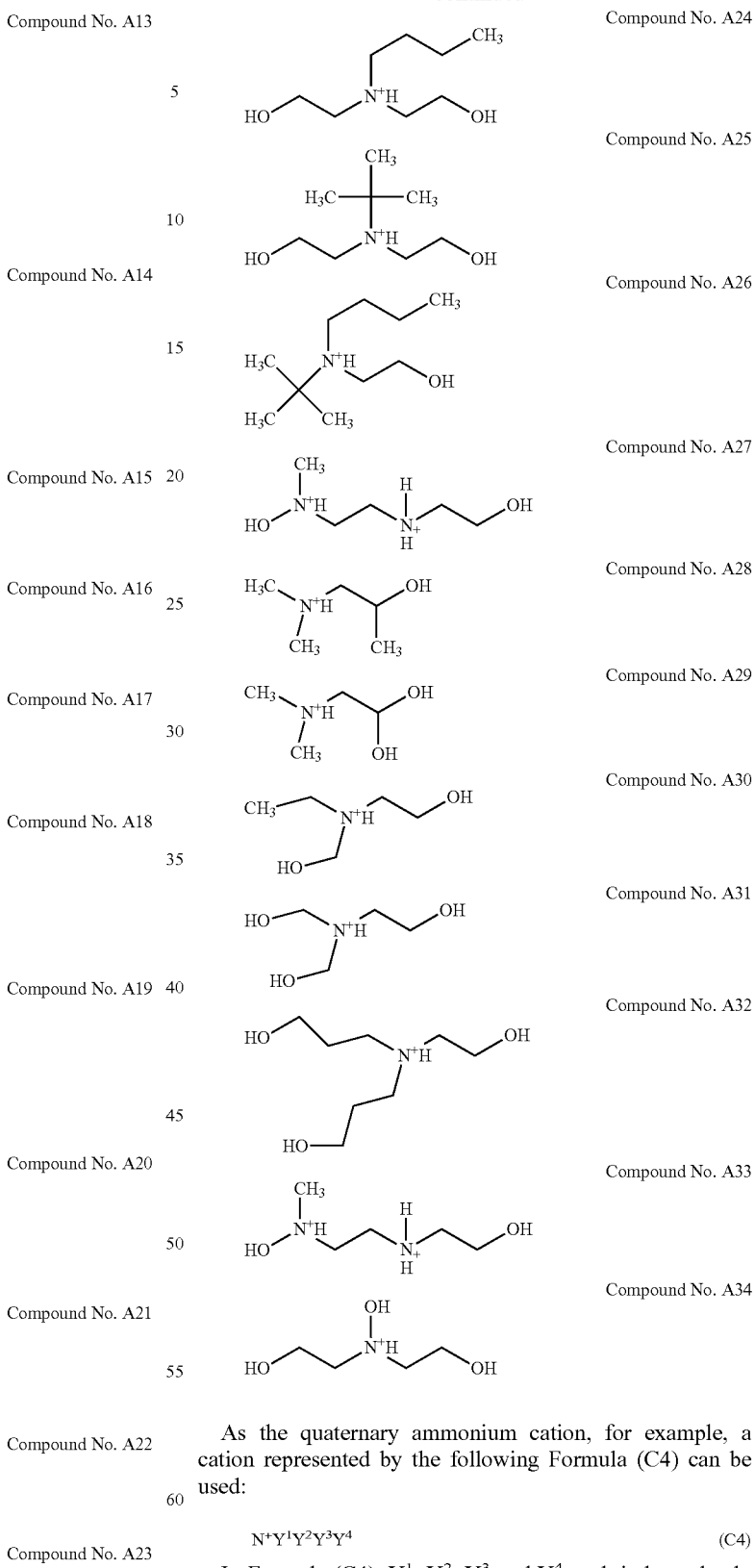

As the quaternary ammonium cation, for example, a cation represented by the following Formula (C4) can be used:

$$N^+Y^1Y^2Y^3Y^4 \qquad (C4)$$

In Formula (C4), $Y^1$, $Y^2$, $Y^3$ and $Y^4$ each independently represent a hydroxy group, an alkyl group having 1 to 6 carbon atoms, an alkenyl group having 2 to 6 carbon atoms, an aryl group having 6 to 15 carbon atoms, or an arylalkyl group having 7 to 13 carbon atoms.

The alkyl group having 1 to 6 carbon atoms, the alkenyl group having 2 to 6 carbon atoms, the aryl group having 6 to 15 carbon atoms and the arylalkyl group having 7 to 13 carbon atoms, which are used as $Y^1$, $Y^2$, $Y^3$ and $Y^4$, may be the same as the respective groups used as $Y^1$ and the like in the above-described Formula (C3).

More specific examples of the quaternary ammonium cation include a tetraalkyl ammonium cation, a pyrrolidine cation, an imidazolium cation, a piperidinium cation, an imidazolinium cation, a morpholinium cation, and a piperazinium cation.

Examples of the tetraalkyl ammonium include tetramethyl ammonium, ethyltrimethyl ammonium, diethyldimethyl ammonium, triethylmethyl ammonium, and tetraethyl ammonium.

Examples of the pyrrolidine cation include N,N-dimethylpyrrolidinium, N-ethyl-N-methyl pyrrolidinium, N,N-diethyl pyrrolidinium, spiro-(1,1')-bipyrrolidinium, and piperidine-1-spiro-1'-pyrrolidinium.

Examples of the imidazolium cation include N,N'-dimethyl imidazolium, N-ethyl-N'-methyl imidazolium, N,N'-diethyl imidazolium, 1-ethyl-2,3-dimethyl imidazolium, 1,2,3-trimethyl imidazolium, and 1,2,3,4-tetramethyl imidazolium.

Examples of the piperidinium cation include: pyridinium cations, such as N-methyl pyridinium, N-ethyl pyridinium, and 1,2-dimethyl pyridinium; N,N-dimethyl piperidinium; N-ethyl-N-methyl piperidinium; and N,N-diethyl piperidinium.

Examples of the imidazolinium cation include N,N-dimethyl imidazolinium, N-ethyl-N'-methyl imidazolinium, N,N-diethyl imidazolinium, 1,2,3,4-tetramethyl imidazolinium, 1,3,4-trim ethyl-2-ethyl imidazolinium, 1,3-dimethyl-2,4-diethyl imidazolinium, 1,2-dimethyl-3,4-diethyl imidazolinium, 1-methyl-2,3,4-triethyl imidazolinium, 1,2,3,4-tetraethyl imidazolinium, 1,2,3-trimethyl imidazolinium, 1,3-dimethyl-2-ethyl imidazolinium, 1-ethyl-2,3-dimethyl imidazolinium, 1-ethyl-2-methyl imidazolinium, and 1,2,3-triethyl imidazolinium.

Examples of the morpholinium cation include N,N-dimethyl morpholinium, N-ethyl-N-methyl morpholinium, and N,N-diethyl morpholinium.

Examples of the piperazinium cation include piperazinium cations, such as N,N,N',N'-tetramethyl piperazinium, N-ethyl-N,N',N'-trimethyl piperazinium, N,N-diethyl-N',N'-dimethyl piperazinium, N,N,N'-triethyl-N'-methyl piperazinium, and N,N,N',N'-tetraethyl piperazinium.

As the primary ammonium cation and the secondary ammonium cation, for example, cations represented by the following Formulae (C1) and (C2) can be used, respectively:

(C2), and

(C1)

$Y^1$ and $Y^2$ in Formula (C2) and $Y^1$ in Formula (C1) each independently represent a hydroxy group, an alkyl group having 1 to 6 carbon atoms, an alkenyl group having 2 to 6 carbon atoms, an aryl group having 6 to 15 carbon atoms, or an arylalkyl group having 7 to 13 carbon atoms.

The alkyl group having 1 to 6 carbon atoms, the alkenyl group having 2 to 6 carbon atoms, the aryl group having 6 to 15 carbon atoms and the arylalkyl group having 7 to 13 carbon atoms, which are used as $Y^1$ and $Y^2$, may be the same as the respective groups used as $Y^1$ and the like in the above-described Formula (C3).

More specific examples of the primary ammonium cation include cations of octylamine, dodecylamine, laurylamine, tetradecylamine, hexadecylamine, stearylamine, oleylamine, allylamine, benzylamine, aniline, and the like. It is noted here that a cation of aniline is specifically represented by $C_6H_5—N^+H^3$.

More specific examples of the secondary ammonium cation include cations of dilaurylamine, ditetradecylamine, dihexadecylamine, distearylamine, N-methylaniline, and the like. Further, as the secondary ammonium cation, for example, the following compound Nos. A51 to No. A57 can be used as well:

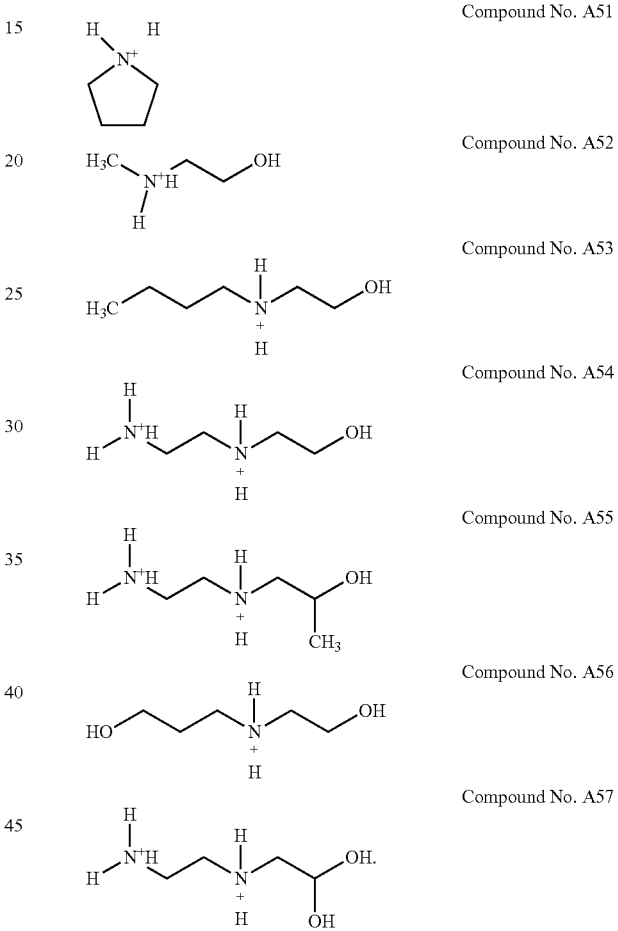

Examples of the tertiary sulfonium cation include (2-carboxyethyl)dimethyl sulfonium, (3-chloropropyl)diphenyl sulfonium, cyclopropyldiphenyl sulfonium, diphenyl (methyl) sulfonium, tri-n-butyl sulfonium, tri-p-tolyl sulfonium, triethyl sulfonium, trimethyl sulfonium, and triphenyl sulfonium.

Examples of the tertiary oxonium cation include triethyl oxonium and trimethyl oxonium.

Examples of the quaternary phosphonium cation include tetrabutyl phosphonium and butyltriphenyl phosphonium.

Examples of the tertiary carbocation include trisubstituted carbocations, such as triphenyl carbocation and tri(substituted phenyl)carbocation. Examples of the tri(substituted phenyl)carbocation include tri(methylphenyl)carbocation and tri(dimethylphenyl)carbocation.

As the cationic component, from the standpoint of making it easier to adjust the absorption wavelength for, for example, improving the light absorption efficiency in a long-wavelength range, a compound represented by Formula (A2) below (hereinafter, may be referred to as "compound A2") can be preferably used. In other words, the compound A of the present invention may be a salt formed by a compound A represented by Formula (A) that has an acidic group salt and a compound A represented by Formula (A) that has a salt of the basic group B, namely a salt formed by an anionic group contained in the salt-forming group of one of the compounds A and a cationic group contained in the salt-forming group of the other compound A.

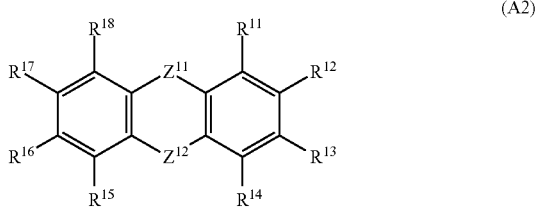

(A2)

In Formula (A2), $Z^{11}$ represents a direct bond, $-NR^{201}-$, $-O-$, $-S-$, $-SO-$, or $-CO-$; $Z^{12}$ represents $-C(R^{202})_2-$, $NR^{201}-$, $-O-$, $-S-$, $-SO-$, or $-CO-$; $R^{11}$ to $R^{18}$ each independently represent a hydrogen atom, CN, NO$_2$, a hydroxy group, an alkyl group having 1 to 20 carbon atoms, an aryl group having 6 to 30 carbon atoms, an arylalkyl group having 7 to 30 carbon atoms, a heterocycle-containing group having 2 to 20 carbon atoms, or a group containing a cationic group represented by the following Formula (B2), with at least one of which $R^{11}$ to $R^{18}$ being the group containing the cationic group; and $R^{201}$ and $R^{202}$ each independently represent a hydrogen atom, an alkyl group having 1 to 20 carbon atoms, an aryl group having 6 to 30 carbon atoms, an arylalkyl group having 7 to 30 carbon atoms, or a heterocycle-containing group having 2 to 20 carbon atoms:

(B1)

In Formula (B2), $L_{11}$ represents a direct bond or a (b2+1)-valent linking group; $B^2$ represents a cationic group; b2 represents an integer of 1 to 10; and the asterisk (*) represents a site of binding with a benzene ring.

$L_{11}$ and b2 that are used in Formula (B2) can be the same as $L_1$ and b that are described below in the section of "(2) Other" and, particularly, a case where the salt-forming group B is a basic group salt is preferred. Further, the cationic group represented by Formula (B2) can be the same as the cationic group described below in the section of "(1-2) Basic Group Salt". This is because, by adopting such a structure, the compound A of the present invention has excellent dispersion stability and ease of synthesis.

$Z^{11}$ and $Z^{12}$, $R^{11}$ to $R^{18}$, $R^{201}$ and $R^{202}$ that are used in Formula (A2) can be the same as $Z^1$ and $Z^2$, $R^1$ to $R^8$, $R^{101}$ and $R^{102}$ that are described below in the section of "2. Compound A", respectively.

Examples of the compound A containing the compound A2 as a cationic component include compounds of the below-described Formulae (53) to (60). As the compound A2, a compound in which cationic group-containing moieties of the compounds of the below-described Formulae (29) to (52) that contain a basic group salt as the salt-forming group B are combined can be used as well.

(1-2) Basic Group Salt

The cationic group constituting the basic group salt may be any mono- or higher valent cationic group, and examples thereof include a tertiary sulfonium cation group, a tertiary oxonium cation group, a quaternary phosphonium cation group, a quaternary ammonium cation group, and a tertiary carbocation. Thereamong, the cationic group is preferably a quaternary ammonium cation group. This is because, with the cationic group being any of the above-described groups, the cationic component can form a salt having good storage stability with the above-described anionic group.

The tertiary sulfonium cation group can be a group represented by Formula (C11) and, specifically, it may have a structure in which one of the substituents bound to an S atom of any of the compounds enumerated above as the tertiary sulfonium cation is removed.

The tertiary oxonium cation group can be a group represented by Formula (C12) below and, specifically, it may have a structure in which one of the substituents bound to an O atom of any of the compounds enumerated above as the tertiary oxonium cation is removed.

The quaternary phosphonium cation group can be a group represented by Formula (C13) below and, specifically, it may have a structure in which one of the substituents bound to a P atom of any of the compounds enumerated above as the quaternary phosphonium cation is removed.

The quaternary ammonium cation group can be a group represented by Formula (C14) below and, specifically, it may have a structure in which one of the substituents bound to an N atom of any of the compounds enumerated above as the quaternary ammonium cation is removed.

The tertiary carbocation group can be a group represented by Formula (C15) below and, specifically, it may have a structure in which one of the substituents bound to a C atom of any of the compounds enumerated above as the tertiary carbocation is removed.

(C11)

(C12)

(C13)

(C14)

(C15)

In Formulae (C11) to (C15) $R^{401}$s each independently represent an alkyl group having 1 to 20 carbon atoms, an aryl group having 6 to 30 carbon atoms, an arylalkyl group having 7 to 30 carbon atoms, or a heterocycle-containing group having 2 to 20 carbon atoms and, in Formula (C14), two or three $R^{401}$s optionally form a ring. In Formulae (C11) to (C15), the asterisk (*) represents a site of binding with $L_{11}$.

The alkyl group having 1 to 20 carbon atoms, the aryl group having 6 to 30 carbon atoms, the arylalkyl group having 7 to 30 carbon atoms and the heterocycle-containing group having 2 to 20 carbon atoms, which are used as $R^{401}$, may be the same as the respective groups used as $R^1$ and the like described below in the section of "2. Compound A".

Examples of a group represented by Formula (C14) in which two $R^{401}$s form a ring include a pyrrolidinium cation group, a morpholinium cation group, and a piperazine cation group. Examples of a group represented by Formula (C14) in which three $R^{401}$s form a ring include a pyridinium cation group.

The anionic component forming a salt with the cationic group may be any anionic component as long as it allows the compound A to exhibit a solubility in water. Examples of the anionic component include: halide anions, such as a chloride anion, a bromide anion, an iodide anion, and a fluoride anion; inorganic anions, such as a perchlorate anion, a chlorate anion, a thiocyanate anion, a hexafluorophosphate anion, a hexafluoroantimonate anion, a hexafluoroarsenate anion, and a tetrafluoroborate anion; organic sulfonate anions, such as a methanesulfonate ion, a fluorosulfonate ion, a benzenesulfonate anion, a toluenesulfonate anion, a 1-naphthylsulfonate anion, a 2-naphthylsulfonate anion, a trifluoromethanesulfonate anion, a pentfluoroethanesulfonate anion, a heptafluoropropanesulfonate anion, a nonafluorobutanesulfonate anion, an undecafluoropentanesulfonate anion, a tridecafluorohexanesulfonate anion, a pentadecafluoroheptanesulfonate anion, a heptadecafluorooctanesulfonate ion, a perfluoro-4-ethylcyclohexanesulfonate ion, an N-alkyl(or aryl)diphenylamine-4-sulfonate anion, a 2-amino-4-methyl-5-chlorobenzenesulfonate anion, a 2-amino-5-nitrobenenesulfonate anion, the sulfonate anions described in Japanese Unexamined Patent Application Publication No. 2004-53799, a camphorsulfonate anion, a fluorobenzenesulfonate anion, a difluorobenzenesulfonate anion, a trifluorobenzenesulfonate anion, a tetrafluorobenzenesulfonate anion, and a pentafluorobenzenesulfonate anion; organic phosphate anions, such as an octylphosphate anion, a dodecylphosphate anion, an octadecylphosphate anion, a phenylphosphate anion, a nonylphenylphosphate anion, and a 2,2'-methylenebis(4,6-di-t-butylphenyl)phosphonate anion; organic fluorosulfonimide ions, such as a bis(trifluoromethanesulfone)imide ion, a bis(pentafluoroethanesulfone)imide ion, a bis(heptafluoropropanesulfone)imide ion, a bis(nonafluorobutanesulfone)imide ion, a bis(undecafluoropentanesulfone)imide ion, a bis(pentadecafluoroheptanesulfone)imide ion, a bis(tridecafluorohexanesulfone)imide ion, a bis(heptadecafluorooetanesulfonimide) ion, a (trifluoromethanesulfone)(nonafluorobutanesulfone)imide ion, a (methanesulfone)(trifluoromethanesulfone)imide ion, and a cyclo-hexafluoropropane-1,3-bis(sulfonyl)imide anion; tetraarylborate anions, such as a tetrakis(pentafluorophenyl)borate anion, a tetrakis(4-fluorophenyl)borate ion, a tetraphenylborate ion, and the borate anions described in Japanese Unexamined Patent Application Publication Nos. 2008-81470, 2007-112854 and H6-184170, Japanese Unexamined Patent Application Publication (Translation of PCT Application) No. 2002-526391, and WO PCT/JP2008/069562; various aliphatic or aromatic carboxylate anions; and organic sulfonylmethide ions, such as tris(trifluoromethanesulfonyl)methide and tris(methanesulfonyl)methide, as well as alkylsulfonate ions, fluoro-substituted alkylsulfonate ions, and alkylsulfonimides or fluoro-substituted alkylsulfonimides that are substituted with an acryloyloxy group, a methacryloyloxy group, or an aliphatic cycloalkyl group such as a norbornyl group or an adamantyl group. Further, for example, a quencher anion having a function of deexciting (quenching) an active molecule in an excited state, and a metallocene compound anion such as ferrocene or ruthenocene, which has a cyclopentadienyl ring with an anionic group such as a carboxyl group, a phosphonic acid group or a sulfonic acid group, can also be used as required.

Among the above-described anions, the anionic component is preferably a halide anion, particularly preferably a chloride anion, a bromide anion or the like. This is because, with the anionic component being any of these ions, the compound A has excellent ease of synthesis, storage stability and the like.

(2) Other

In Formula (B1), b represents an integer of 1 to 10, denoting the number of acidic group salts or basic group salts that are bound to $L_1$, namely the number of salt-forming groups B. In the compound A of the present invention, b may be any number as long as the compound A can be imparted with the desired sensitivity and solubility in water; however, b is preferably an integer of 1 to 5, more preferably an integer of 1 or 2, particularly preferably 1. This is because, with the value of b being in this range, the compound A has excellent dispersion stability and ease of synthesis.

In Formula (B1), $L_1$ represents a direct bond or a (b+1)-valent linking group. $L_1$ used as the (b+1)-valent linking group can be a nitrogen atom, an oxygen atom, a sulfur atom, a phosphorus atom, a group represented by the below-described (II-a) or (II-b), —CO—, —NH—CO—, —CO—NH—, —NR$^{53}$—, or an aliphatic hydrocarbon group having 1 to 120 carbon atoms, an aromatic ring-containing hydrocarbon group having 6 to 35 carbon atoms or a heterocycle-containing group having 2 to 35 carbon atoms, which has the same valence as (b+1).

The above-described $R^{53}$ may represent a hydrogen atom, an aliphatic hydrocarbon group having 1 to 120 carbon atoms, an aromatic ring-containing hydrocarbon group having 6 to 35 carbon atoms, or a heterocycle-containing group having 2 to 35 carbon atoms.

The methylene groups in the aliphatic hydrocarbon group, the aromatic ring-containing hydrocarbon group and the heterocycle-containing group, which groups are used as $L_1$ and $R^{53}$, are optionally substituted with —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NH—CO—O—, —NR'—, —S—S—, —SO$_2$—, a nitrogen atom, or a combination thereof, and the hydrogen atoms of the methylene groups may be substituted with hydroxy groups. The aromatic ring and the heterocycle are optionally fused with another ring. It is noted here that (b+1) is 3 when the linking group $L_1$ is a nitrogen atom, a phosphorus atom or a linking group represented by Formula (II-a) or (II-b) below, or (b+1) is 2 when the linking group $L_1$ is an oxygen atom, a sulfur atom, —CO—, —NH—CO—, —CO—NH— or —NR$^{53}$—.

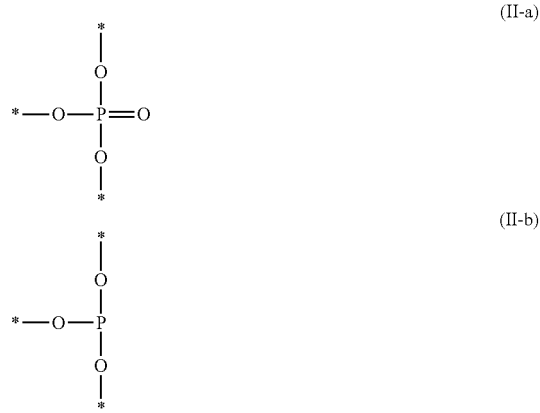

Examples of the aliphatic hydrocarbon group having 1 to 120 carbon atoms that is used as $R^{53}$ include: alkyl groups, such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, and decyl; alkoxy groups, such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, Cert-heptyloxy, n-octyloxy, isooctyloxy, tert-octyloxy, 2-ethylhexyloxy, nonyloxy, and decyloxy; alkylthio groups, such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, and 2-ethylhexylthio; alkenyl groups, such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl; and these groups that are substituted with any of the below-described substituents.

Examples of the aromatic ring-containing hydrocarbon group having 6 to 35 carbon atoms that is used as $R^{53}$ include: arylalkyl groups, such as benzyl, phenethyl, diphenylmethyl, triphenylmethyl, styryl, and cinnamyl; aryl groups, such as phenyl and naphthyl; aryloxy groups, such as phenoxy and naphthyloxy; arylthio groups, such as phenylthio and naphthylthio; and these groups that are substituted with any of the below-described substituents.

Examples of the heterocycle-containing group having 2 to 35 carbon atoms that is used as $R^{53}$ include pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, 2,4-dioxyoxazolidin-3-yl, benzotriazolyl, and these groups that are substituted with any of the below-described substituents.

The structure of the aliphatic hydrocarbon group having 1 to 120 carbon atoms that is used as the linking group $L_1$ and has the same valence as (b+1) can be set as appropriate in accordance with the intended use and the like of the compound A of the present invention. As this aliphatic hydrocarbon group, any of such linear, branched or cyclic (alicyclic) hydrocarbons and combinations thereof can be used.

Further, one or more methylene groups in the above-described aliphatic hydrocarbon group are optionally substituted with —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NH—CO—O—, —NR'—, —S—S—, —SO$_2$—, a nitrogen atom, or a combination thereof.

A di- or higher valent aliphatic hydrocarbon group having 1 to 120 carbon atoms that is used as the linking group $L_1$ may have a structure in which some of the hydrogen atoms are removed from a monovalent aliphatic hydrocarbon group having 1 to 120 carbon atoms that is used as the above-described $R^{53}$.

Specific examples of a divalent aliphatic hydrocarbon group having 1 to 120 carbon atoms that is used as the linking group $L_1$ include: alkylenes, such as methylene, ethylene, propylene, butylene, and butyldiyl; groups obtained by substituting the methylene groups of these alkylenes with —O—, —S—, —CO—O—, or —O—CO—; residues of diols, such as ethanediol, propanediol, butanediol, pentanediol, and hexanediol; residues of dithiols, such as ethanedithiol, propanedithiol, butanedithiol, pentanedithiol, and hexanedithiol; and these groups that are substituted with any of the below-described substituents.

Specific examples of a trivalent (b+1) aliphatic hydrocarbon group having 1 to 120 carbon atoms that is used as the linking group $L_1$ include: alkylidynes, such as propylidyne and 1,1,3-butylidyne; and these groups that are substituted with any of the below-described substituents.

The structure of the aromatic ring-containing hydrocarbon group having 6 to 35 carbon atoms that is used as the linking group $L_1$ and has the same valence as (b+1) can be set as appropriate in accordance with the intended use and the like of the compound A of the present invention.

Further, one or more methylene groups in the above-described aromatic ring-containing hydrocarbon group are optionally substituted with —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NH—CO—O—, —NR'—, —S—S—, —SO$_2$—, a nitrogen atom, or a combination thereof.

A di- or higher valent aromatic ring-containing hydrocarbon group having 6 to 35 carbon atoms that is used as the linking group $L_1$ may have a structure in which some of the hydrogen atoms are removed from a monovalent aromatic ring-containing hydrocarbon group having 6 to 35 carbon atoms that is used as the above-described $R^{53}$.

Specific examples of a divalent aromatic ring-containing hydrocarbon group having 6 to 35 carbon atoms that is used as the linking group $L_1$ include: arylene groups, such as phenylene and naphthylene; residues of bifunctional phenols, such as catechol and bisphenol; 2,4,8,10-tetraoxaspiro[5,5]undecane; and these groups that are substituted with any of the below-described substituents.

Examples of a trivalent aromatic ring-containing hydrocarbon group having 6 to 35 carbon atoms which is used as the linking group $L_1$ include phenyl-1,3,5-trimethylene, and this group substituted with any of the below-described substituents.

The structure of the heterocycle-containing group having 2 to 35 carbon atoms that is used as the linking group $L_1$ and has the same valence as (b+1) can be set as appropriate in accordance with the intended use and the like of the compound A of the present invention.

Further, one or more methylene groups in the above-described heterocycle-containing group are optionally substituted with —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NH—CO—O—, —NR'—, —S—S—, —SO$_2$—, a nitrogen atom, or a combination thereof.

A di- or higher valent heterocycle-containing group having 2 to 35 carbon atoms that is used as the linking group $L_1$ may have a structure in which some of the hydrogen atoms are removed from a monovalent heterocycle-containing group having 2 to 35 carbon atoms that is used as the above-described $R^{53}$.

Specific examples of a divalent heterocycle-containing group having 2 to 35 carbon atoms that is used as the linking group $L_1$ include groups having a pyridine ring, a pyrimidine ring, a piperidine ring, a piperazine ring, a triazine ring, a furan ring, a thiophene ring, an indole ring or the like, and these groups that are substituted with any of the below-described substituents.

Examples of a trivalent heterocycle-containing group having 2 to 35 carbon atoms which is used as the linking group $L_1$ include isocyanuric ring-containing groups, triazine ring-containing groups, and these groups that are substituted with any of the below-described substituents.

The above-described functional groups, such as aliphatic hydrocarbon group, aromatic ring-containing hydrocarbon group and heterocycle-containing group, may each have a substituent and, unless otherwise specified, they are each unsubstituted with no substituent, or have a substituent. Substituents that substitute hydrogen atoms of such aliphatic hydrocarbon group, aromatic ring-containing hydrocarbon group and heterocycle-containing group may be the same as the respective substituents that substitute hydrogen atoms of the alkyl group and the like used as $R^1$ and the like described below in the section of "2. Compound A". As the substituents, for example, from the standpoint of further improving the solubility in water and the like of the compound A, hydrophilic groups such as a hydroxy group can be used.

When the salt-forming group B is an acidic group salt, the linking group $L_1$ is preferably a direct bond, —CO—, —NH—CO—, —CO—NH—, —NR$^{53}$—, or an aliphatic hydrocarbon group having 1 to 120 carbon atoms that has the same valence as (b+1), more preferably a direct bond or an aliphatic hydrocarbon group having 1 to 20 carbon atoms that has the same valence as (b+1), particularly preferably a direct bond, i.e. the acidic group salt is directly bound to a benzene ring. This is because it allows the compound A of the present invention to be used as a radical polymerization initiator having superior sensitivity. For example, when the anionic group constituting the salt-forming group B is a carboxylic acid ion group or the like, a conjugated structure is easily formed between a tricyclic structure and a group containing the salt-forming group B, as a result of which the compound A more readily absorbs light in a long wavelength range as compared to a case of having only the tricyclic structure.

When the salt-forming group B is a basic group salt, the linking group $L_1$ is preferably an aliphatic hydrocarbon group having 1 to 20 carbon atoms, more preferably an aliphatic hydrocarbon group having 2 to 10 carbon atoms. This is because it allows the compound A to have excellent dispersion stability and ease of synthesis.

In the linking group $L_1$, when the salt-forming group B is a basic group salt, one or more methylene groups in the above-described aliphatic hydrocarbon group, aromatic ring-containing hydrocarbon group and heterocycle-containing group are preferably substituted with —O—, —S—, —CO—, —O—CO—, —OCO—O—, —O—CO—O—, —S—CO—, —CO—S—, —S—CO—O—, —O—CO—S—, —CO—NH—, —NH—CO—, —NH—CO—O—, —NH—CO—O—, —NR'—, —S—S—, —SO$_2$—, or a combination thereof, more preferably substituted with —O—, and it is particularly preferred that the terminal on the benzene ring side be substituted with —O—, i.e. a terminal of $L_1$ be bound to a benzene ring via —O—. This is because, by adopting the above-described structure, the compound A of the present invention is imparted with excellent ease of synthesis.

In the compound A of the present invention, at least one of $R^1$ to $R^8$ is a group containing the salt-forming group B. The number of groups containing the salt-forming group B, namely the number of such groups contained as $R^1$ to $R^8$, may be any number as long as the compound A can be imparted with the desired sensitivity and solubility in water, and the number of such groups in the compound A may be 8 or less, preferably 1 to 2, more preferably 1. This is because, in this range, the compound A of the present invention has excellent ease of synthesis, storage stability, solubility in water, and the like.

The binding position of a group containing the salt-forming group B may be any position as long as the compound A can be imparted with the desired sensitivity and solubility in water, and the group containing the salt-forming group B may be contained as a substituent of any of $R^1$ to $R^8$; however, it is preferably, for example, $R^4$. This is because, by adopting such a structure, the compound A of the present invention is imparted with excellent ease of synthesis. In addition, the compound A of the present invention is imparted with excellent storage stability, solubility in water, and the like.

2. Compound A

Examples of the alkyl group having 1 to 20 carbon atoms that is used as $R^1$ to $R^8$ and $R^{101}$ and $R^{102}$ include methyl, ethyl, propyl, iso-propyl, butyl, sec-butyl, tert-butyl, iso-butyl, amyl, iso-amyl, tert-amyl, cyclopentyl, hexyl, 2-hexyl, 3-hexyl, cyclohexyl, 4-methylcyclohexyl, heptyl, 2-heptyl, 3-heptyl, iso-heptyl, tort-heptyl, 1-octyl, iso-octyl, tert-octyl, and adamantyl.

Examples of the aryl group having 6 to 30 carbon atoms that is used as $R^1$ to $R^8$ and $R^{101}$ and $R^{102}$ include phenyl, naphthyl, and anthracenyl.

One or more hydrogen atoms in the above-described aryl group may be substituted with an alkyl group. As the alkyl group substituting a hydrogen atom(s) in the aryl group, among those alkyl groups having 6 to 20 carbon atoms that are used as $R^1$ and the like, one having a prescribed number of carbon atoms can be used.

Examples of the arylalkyl group having 7 to 30 carbon atoms that is used as $R^1$ to $R^8$ and $R^{101}$ and $R^{102}$ include benzyl, fluorenyl, indenyl, and 9-fluorenylmethyl. One or more hydrogen atoms in the above-described arylalkyl group may be substituted with an alkyl group. As the alkyl group substituting a hydrogen atom(s) in the arylalkyl group, among those alkyl groups having 6 to 20 carbon atoms that are used as $R^1$ and the like, one having a prescribed number of carbon atoms can be used.

Examples of the heterocycle-containing group having 2 to 20 carbon atoms that is used as $R^1$ to $R^8$ and $R^{101}$ and $R^{102}$ include pyridyl, pyrimidyl, pyridazyl, piperidyl, pyranyl, pyrazolyl, triazyl, pyrrolyl, quinolyl, isoquinolyl, imidazolyl, benzimidazolyl, thiazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, and 2,4-dioxyoxazolidin-3-yl.

The above-described functional groups, such as alkyl group having 1 to 20 carbon atoms, aryl group having 6 to 30 carbon atoms, arylalkyl group having 7 to 30 carbon atoms and heterocycle-containing group having 2 to 20 carbon atoms, may each have a substituent and, unless otherwise specified, they are unsubstituted with no substituent, or each have a substituent.

In the compound of the present invention, when a hydrogen atom in a group is substituted with a substituent, the number of carbon atoms of the group means the number of carbon atoms of the group after the substitution. For example, when a hydrogen atom of the above-described alkyl group having 1 to 20 carbon atoms is substituted, "1 to 20 carbon atoms" indicates the number of carbon atoms after the hydrogen atom is substituted, not the number of carbon atoms before the hydrogen atom is substituted. Meanwhile, in the compound of the present invention, when a methylene group in a group having a prescribed number of carbon atoms is substituted with a divalent group, the number of carbon atoms means the number of carbon atoms of the group before the substitution. For example, in the present specification, the number of carbon atoms of a group obtained by substituting a methylene group of an alkyl group having 1 to 20 carbon atoms with a divalent group is 1 to 20.

Examples of a substituent that substitutes a hydrogen atom of the alkyl group, aryl group, arylalkyl group, heterocycle-containing group or the like include ethylenically unsaturated groups, such as vinyl, allyl, acryl, and methacryl; halogen atoms, such as fluorine, chlorine, bromine, and iodine; acyl groups, such as acetyl, 2-chloroacetyl, propionyl, octanoyl, acryloyl, methacryloyl, phenylcarbonyl (benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups, such as acetyloxy and benzoyloxy; substituted amino groups, such as amino, ethylamino, methylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, and phenylsulfonylamino; a sulfonamide group; a sulfonyl group; a carboxyl group; a cyano group; a sulfo group; a hydroxyl group; a nitro group; a mercapto group; an imide group; a carbamoyl group; a phosphonate group; and a phosphate group.

In other words, one or more hydrogen atoms in the alkyl group, the aryl group, the arylalkyl group and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group.

In the above-described alkyl group having 1 to 20 carbon atoms, aryl group having 6 to 30 carbon atoms, arylalkyl group having 7 to 30 carbon atoms, and heterocycle-containing group having 2 to 20 carbon atoms, one or more methylene groups may be substituted with a combination of groups selected a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, and —SO$_2$— such that oxygen atoms are not arranged adjacent to one another, or the methylene groups may be unsubstituted. Further, R' represents a hydrogen atom or an alkyl group having 1 to 8 carbon atoms.

In other words, one or more methylene groups in the alkyl group, the aryl group, the arylalkyl group and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another. R' represents a hydrogen atom or an alkyl group having 1 to 8 carbon atoms.

As a group substituted with a divalent group such as —O—, a group in which a terminal methylene group is substituted can be used, and examples thereof include alkyl groups in which a terminal methylene group is substituted with —O—, namely alkoxy groups.

Further, in the alkyl group, the aryl group, the arylalkyl group and the heterocycle-containing group that are used as $R^1$, $R^2$, $R^3$, $R^4$, $R^5$, $R^6$, $R^7$, $R^8$, $R^{101}$ and $R^{102}$, one or more hydrogen atoms may be substituted with a substituent, and one or more methylene groups may be substituted with any of the above-described divalent groups.

For example, as exemplified below in Formulae (302), (303) and the like, an alkyl group in which one or more methylene groups are substituted with —O— and one or more hydrogen atoms are further substituted with hydroxy groups can also be used as $R^1$, $R^2$, $R^3$, $R^4$, $R^5$, $R^6$, $R^7$ and $R^8$ and $R^{101}$ and $R^{102}$.

As for $R^1$ to $R^8$, adjacent groups of $R^1$ and $R^2$, $R^2$ and $R^3$, $R^3$ and $R^4$, $R^5$ and $R^6$, $R^6$ and $R^7$, and $R^7$ and $R^8$ are optionally bound together to form a ring, and optionally form a fused ring with a benzene ring constituting a three-membered ring in Formula (A).

Examples of a ring structure that is formed by adjacent groups bound together include a cyclopentene ring, a cyclohexene ring, a dihydrofuran ring, a dihydropyran ring, a benzene ring, and a naphthalene ring.

When $R^1$ to $R^8$ are groups other than a group containing the salt-forming group B, they are each a hydrogen atom, CN, NO$_2$, a hydroxy group, an alkyl group having 1 to 20 carbon atoms, an aryl group having 6 to 30 carbon atoms, an arylalkyl group having 7 to 30 carbon atoms, or a heterocycle-containing group having 2 to 20 carbon atoms, preferably a hydrogen atom or an alkyl group having 1 to 10 carbon atoms, more preferably a hydrogen atom or an alkyl group having 1 to 5 carbon atoms, particularly preferably a hydrogen atom. More specifically, as the compound A of the present invention, when $R^4$ is a group containing a salt-forming group, a compound in which $R^1$ to $R^3$ and $R^5$ to $R^8$ are hydrogen atoms can be preferably used. This is because it allows the compound A of the present invention to have excellent ease of synthesis, storage stability, solubility in water, and the like.

When $R^1$ to $R^8$ are groups other than a group containing the salt-forming group B, from the standpoint of improving the light absorption efficiency of the compound A of the present invention in a long wavelength range, $R^1$ to $R^8$ are each preferably a group capable of forming a conjugated system with the three-membered ring, such as $NO_2$ or an aryl group having 6 to 30 carbon atoms.

$R^{101}$ and $R^{102}$ are each a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms, preferably a hydrogen atom or an alkyl group having 1 to 20 carbon atoms, more preferably a hydrogen atom or an alkyl group having 1 to 5 carbon atoms. This is because it allows the compound A of the present invention to have excellent dispersion stability and ease of synthesis.

The above-described $Z^1$ is a direct bond, $-NR^{101}-$, $-O-$, $-S-$, $-SO-$, or $-CO-$, and the above-described $Z^2$ is $-C(R^{102})_2-$, $NR^{101}$, $-O-$, $-S-$, $-SO-$, or $-CO-$.

As a combination of $Z^1$ and $Z^2$, such a combination that allows the tricyclic structure containing two benzene rings bound by $Z^1$ and $Z^2$ to exhibit an aromatic property is preferred. This is because it enables the compound A of the present invention to absorb light in a broad wavelength range including long-wavelength light.

Examples of the combination of $Z^1$ and $Z^2$ include combinations of $-S-$ and $-CO-$ (thioxanthone structure), $-N-$ and $-N-$ (phenazine structure), $-N-$ and $-CO-$ (acridone structure), and a direct bond and $-CO-$ (fluorenone structure). It is noted here that the three-membered ring structures formed by the respective combinations are shown in parentheses.

Among these combinations, the combination of $-S-$ and $-CO-$ (thioxanthone structure) is preferred in the compound A of the present invention. In other words, the compound A represented by Formula (A) in the present invention is preferably a compound represented by Formula (A1) below. This is because, with $Z^1$ and $Z^2$ being the above-described combination, the compound A of the present invention can be easily used as a radical polymerization initiator which has superior sensitivity and solubility in water. It is noted here that, when $Z^1$ is a direct bond, the ring structure containing $Z^1$ and $Z^2$, which is interposed between two benzene rings, is a 5-membered ring structure.

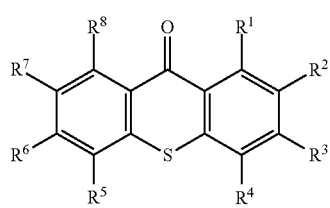

(A1)

In Formula (A1), $R^1$, $R^2$, $R^3$, $R^4$, $R^5$, $R^6$, $R^2$ and $R^8$ each independently represent a hydrogen atom, CN, $NO_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group B, which is represented by the above-described Formula (B1), and at least one of $R^1$ to $R^8$ is the salt-forming group B.

With regard to $R^1$ to $R^8$ used in Formula (A1) and the above-described Formula (B1), the same as described above for Formula (A) is applied.

Specific examples of the compound A of the present invention include the following compounds:

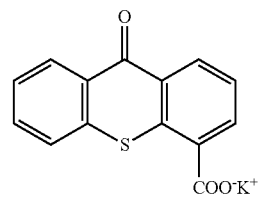

(1)

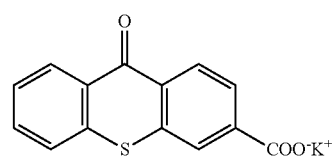

(2)

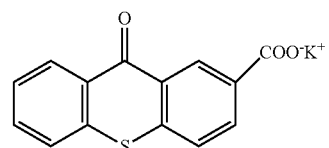

(3)

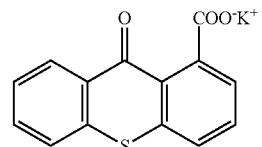

(4)

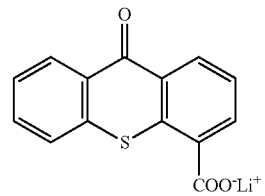

(5)

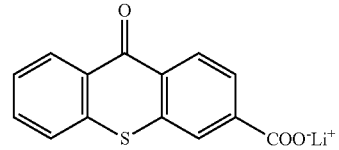

(6)

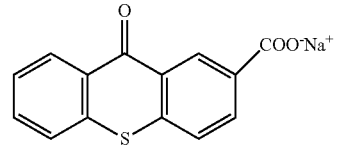

(7)

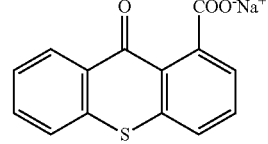

(8)

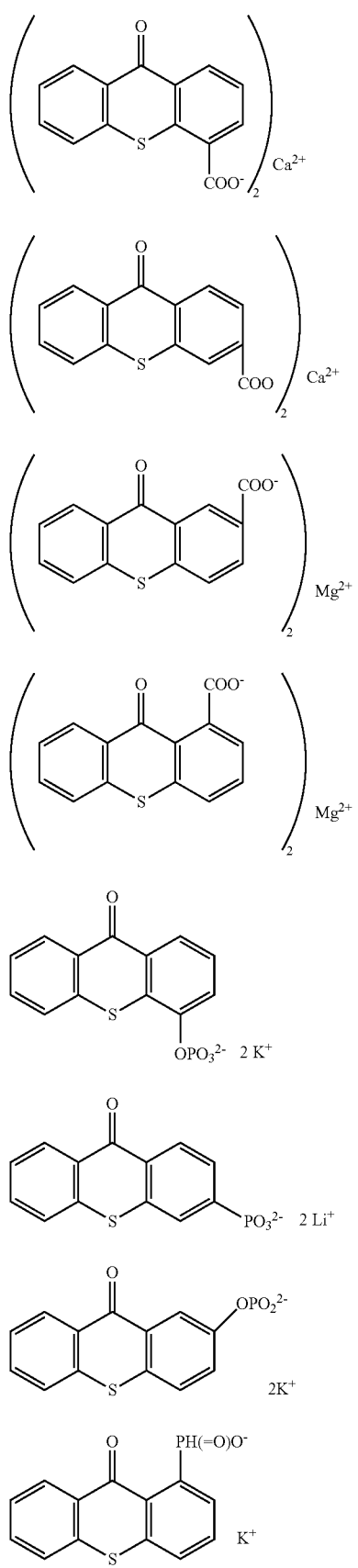
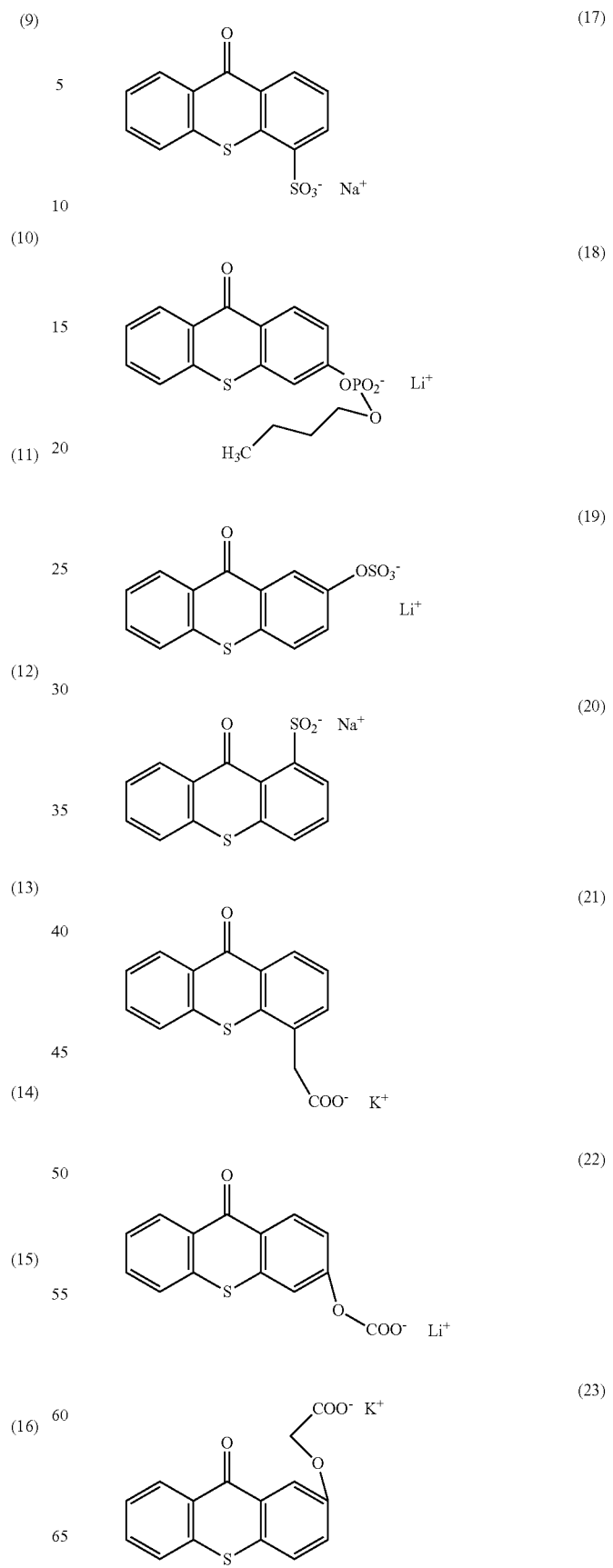

-continued
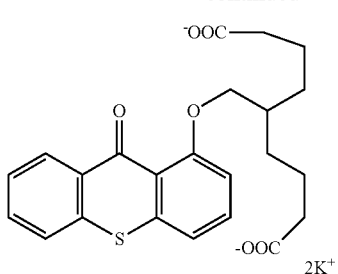
(24)
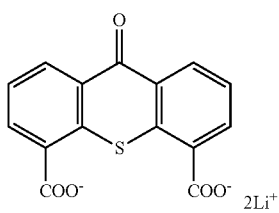
(25)
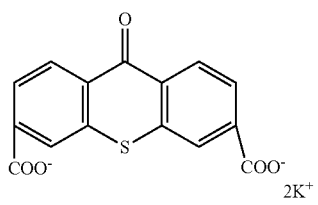
(26)
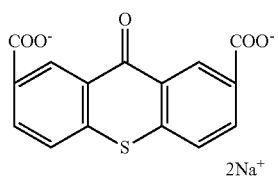
(27)
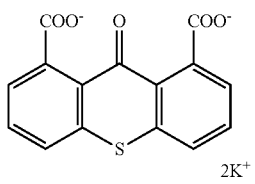
(28)
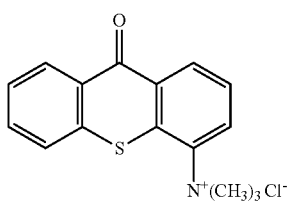
(29)
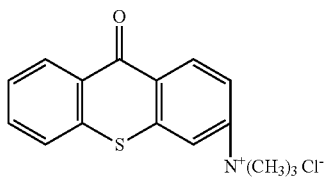
(30)
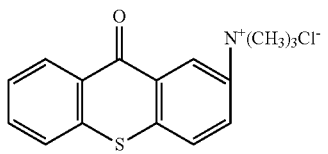
(31)
-continued
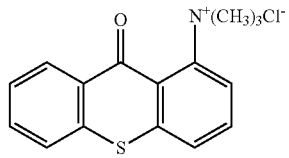
(32)
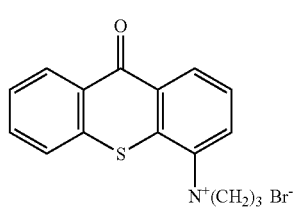
(33)
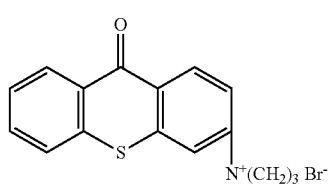
(34)
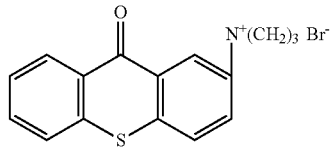
(35)
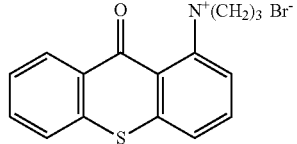
(36)
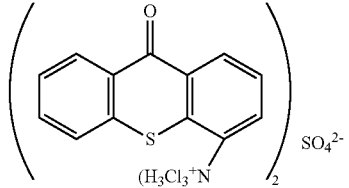
(37)
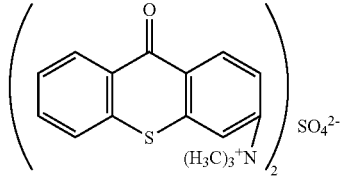
(38)
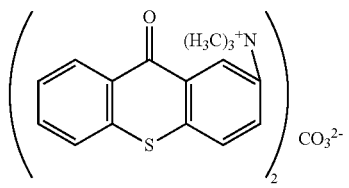
(39)

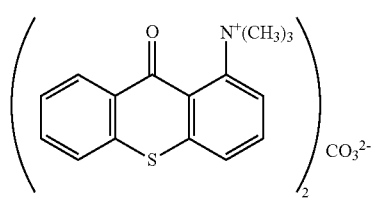
(40)
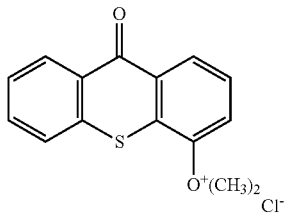
(41)
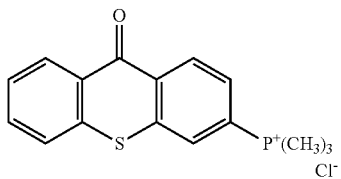
(42)
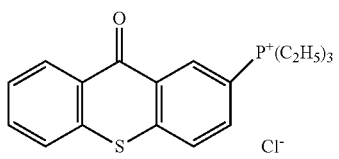
(43)
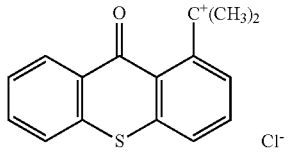
(44)
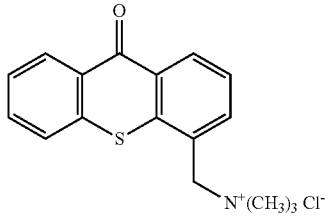
(45)
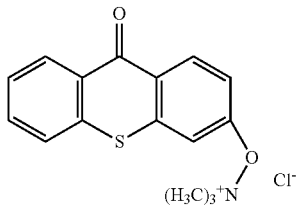
(46)
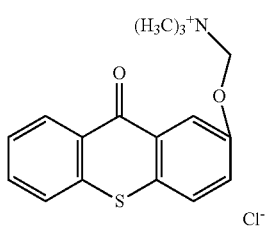
(47)
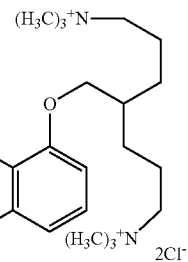
(48)
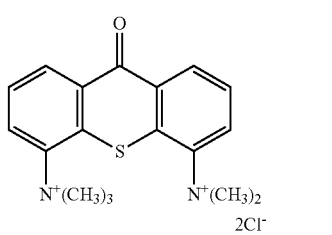
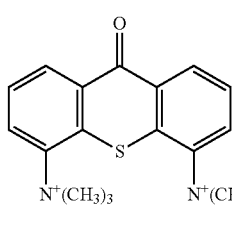
(49)
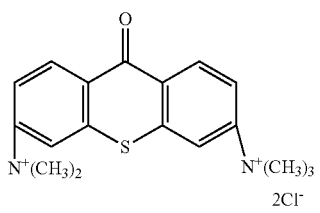
(50)
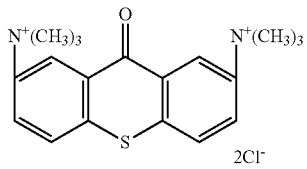
(51)
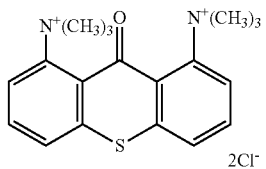
(52)
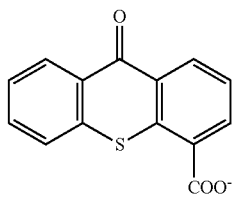
(53)
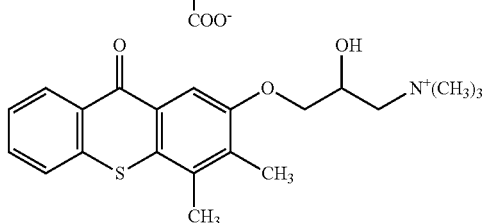
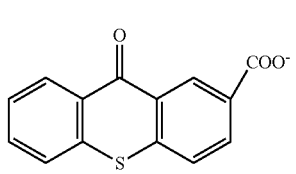
(54)

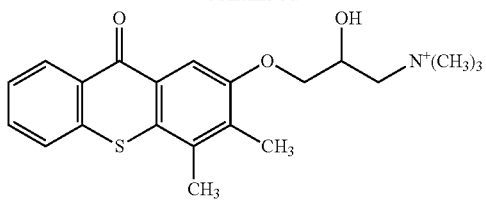
(55)
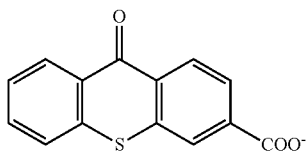
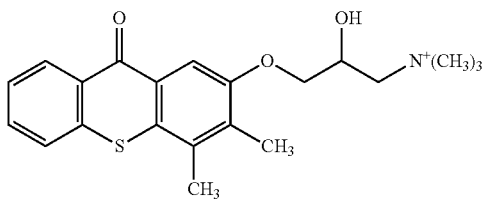
(56)
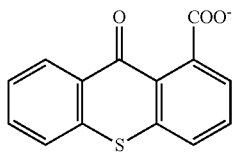
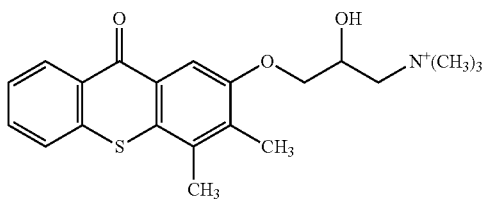
(57)
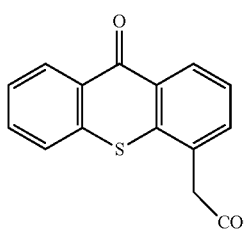
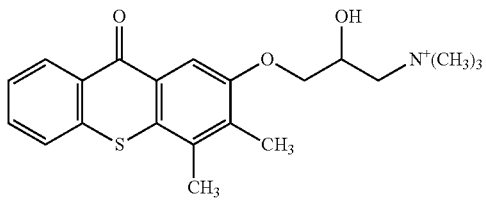
(58)
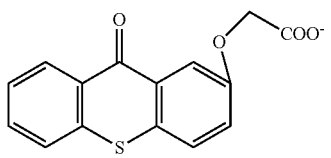
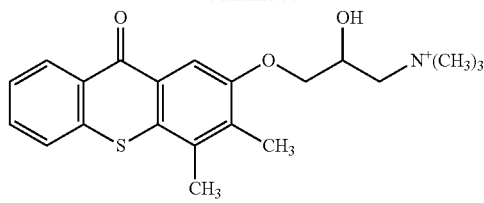
(59)
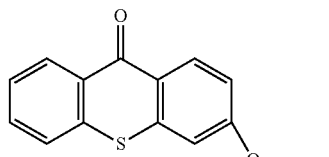
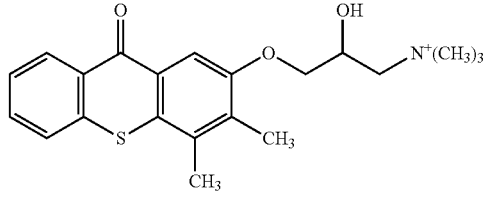
(60)
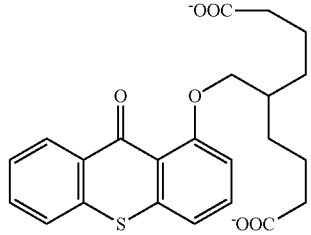
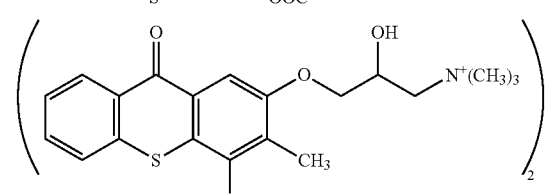
(61)
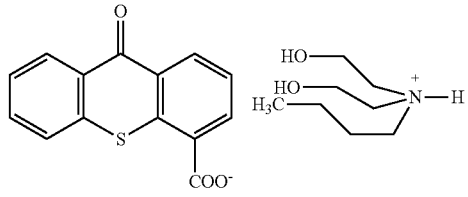
(62)
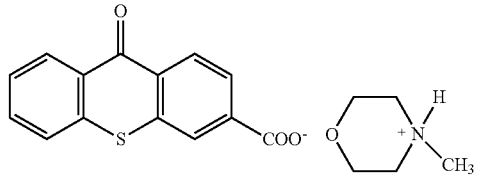
(63)
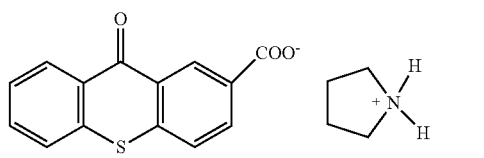

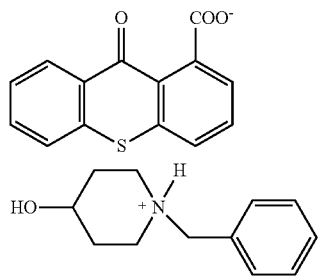
(64)
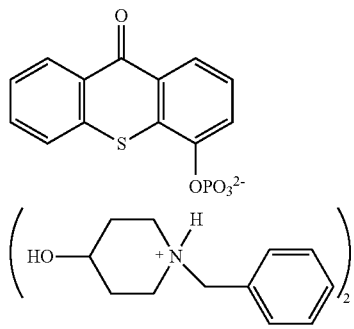
(65)
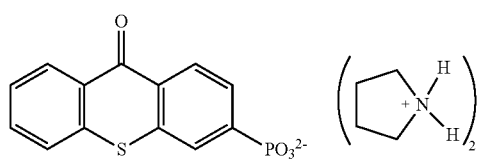
(66)
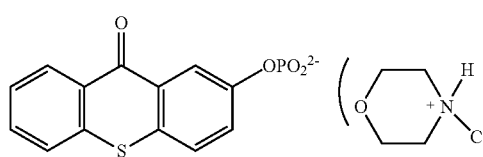
(67)
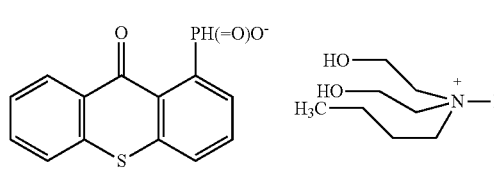
(68)
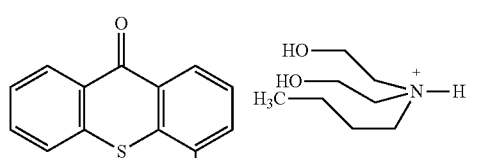
(69)
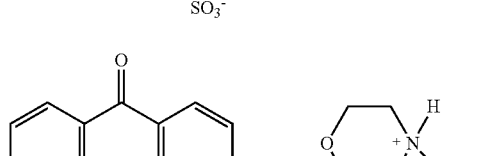
(70)
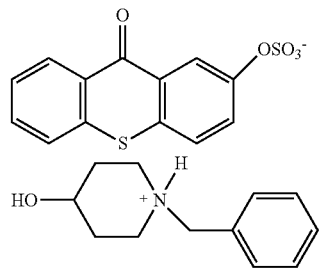
(71)
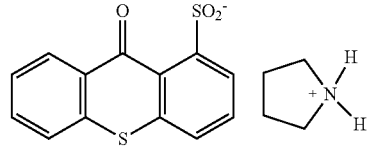
(72)
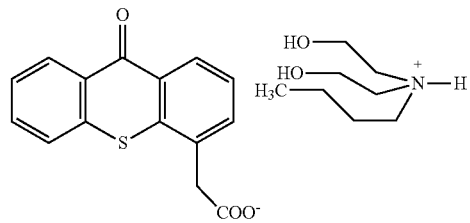
(73)
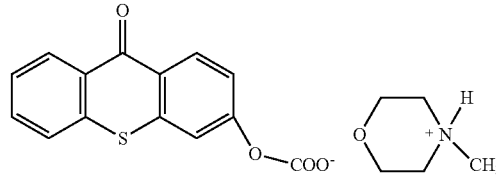
(74)
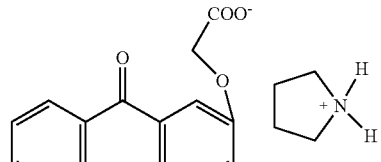
(75)
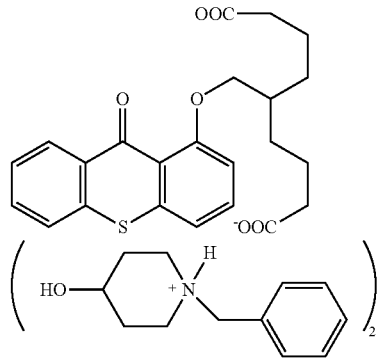
(76)
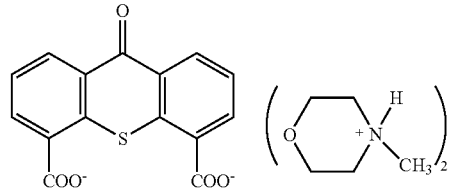
(77)

(78) 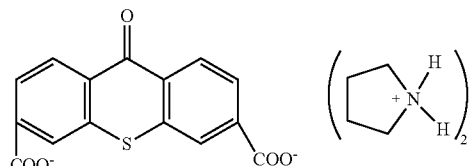
(79) 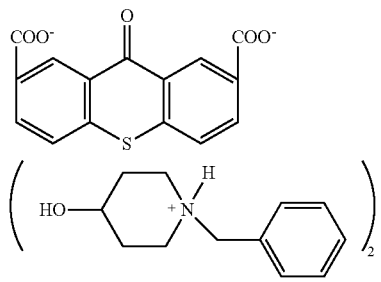
(80) 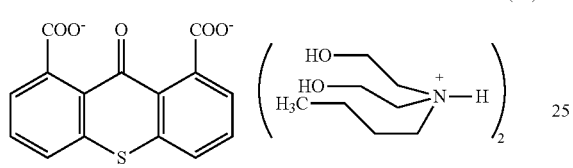
(81) 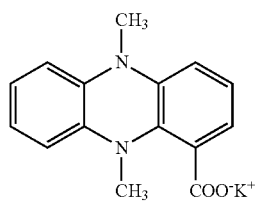
(82) 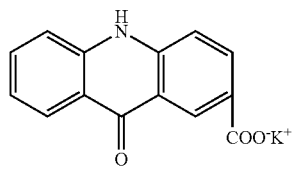
(83) 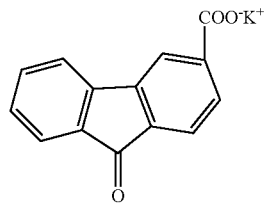
(84) 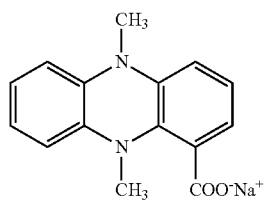
(85) 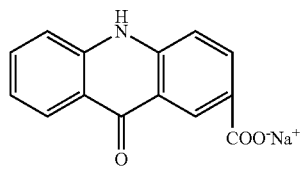
(86) 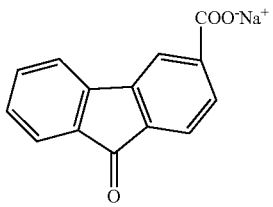
(87) 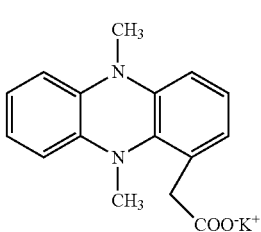
(88) 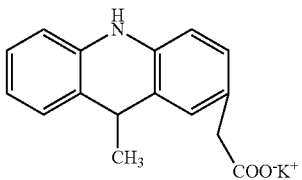
(89) 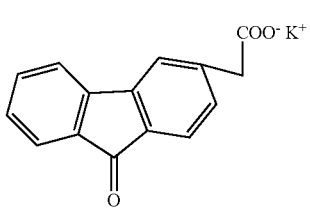
(90) 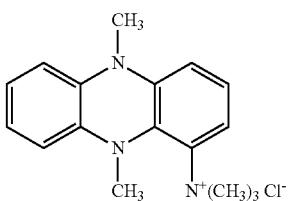
(91) 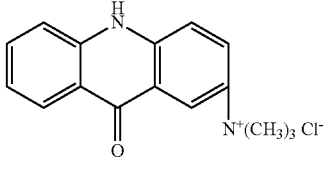
(92) 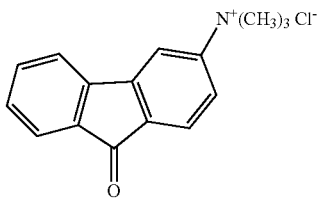
(93) 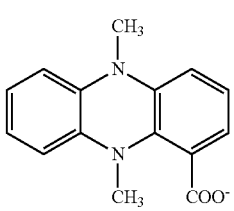

(94) 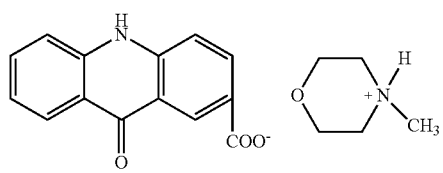
(95) 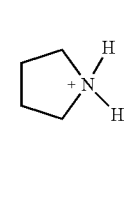 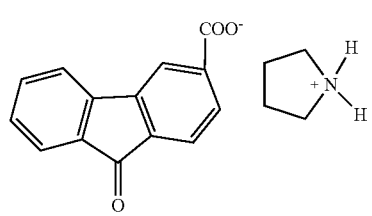
(96) 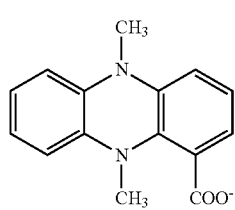
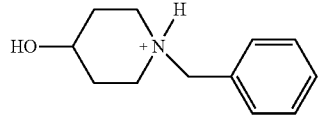
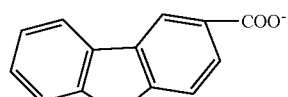
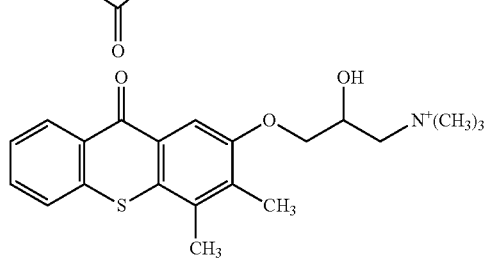
(301) 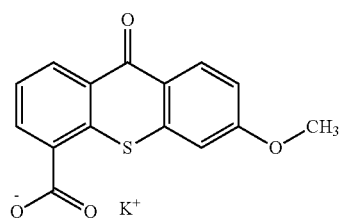
(302) 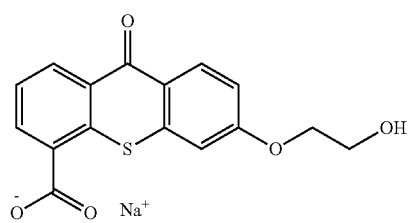
(303) 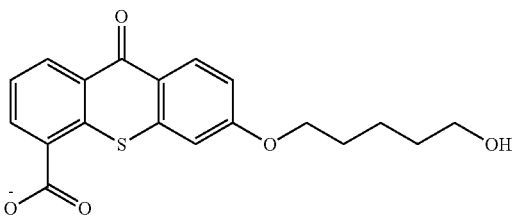
(304) 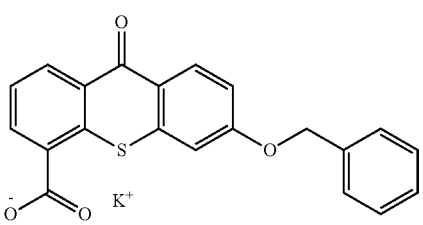
(305) 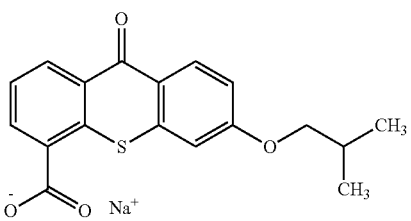
(306) 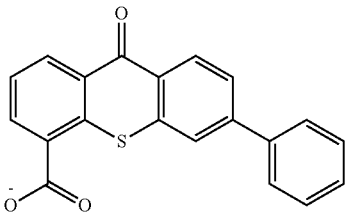
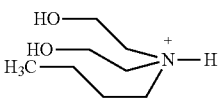
(307) 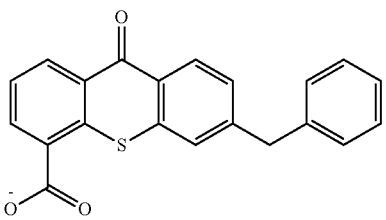
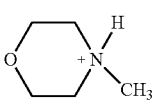

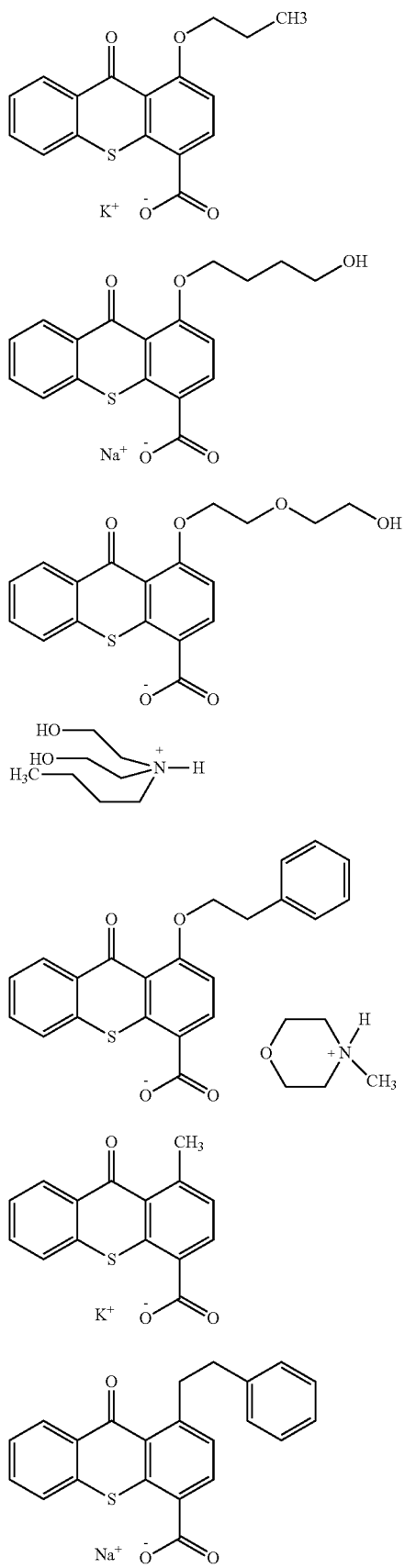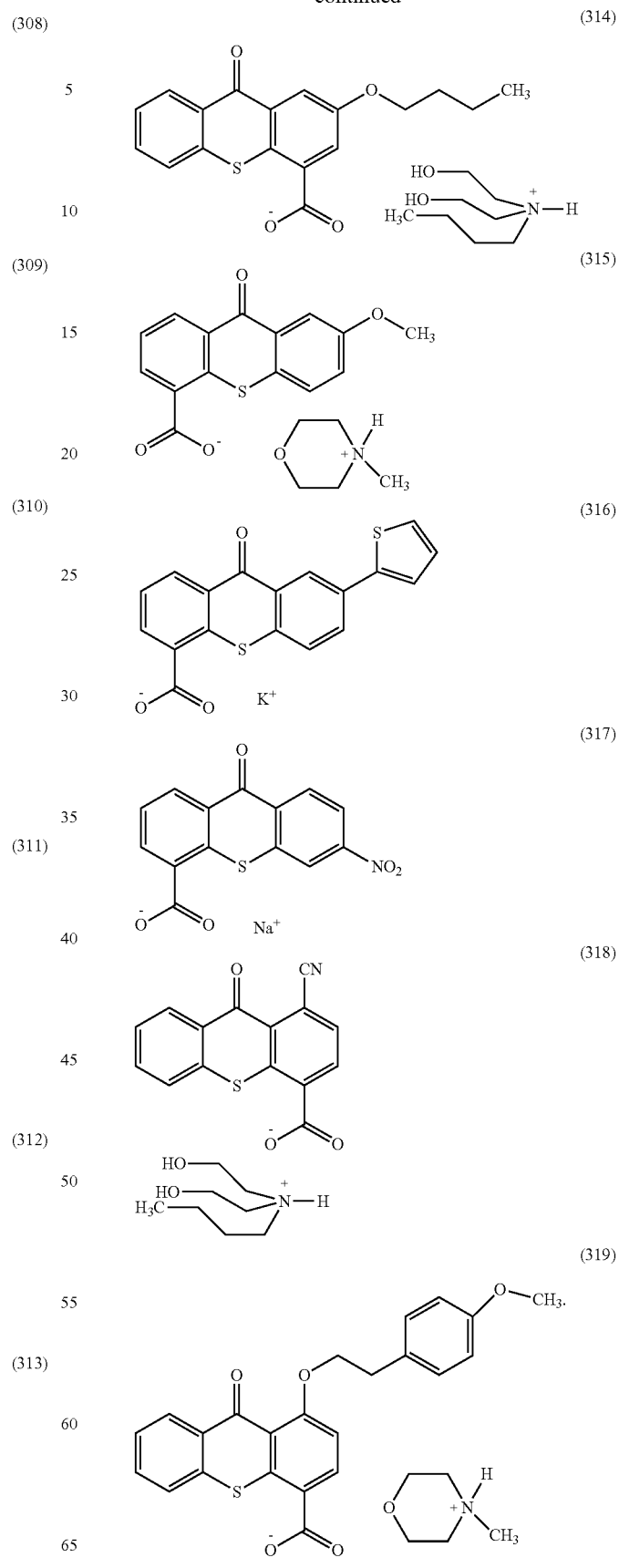

The compound A of the present invention may have any maximum absorption wavelength in a range of 300 nm to 600 nm as long as the compound A can absorb an exposure light and generate a radical; however, the maximum absorption wavelength is preferably 380 nm or longer, more preferably 385 nm to 550 nm, particularly preferably 390 nm to 500 nm, especially preferably 390 nm to 450 nm. This is because, with the maximum absorption wavelength being in this range, the compound A of the present invention is more useful as a radical polymerization initiator having excellent sensitivity.

Hereinafter, a method of measuring the maximum absorption wavelength presents no problem as long as it is capable of measuring the maximum absorption wavelength with good accuracy and, for example, the following method can be employed:

(1) dissolve the compound A in water to prepare a measurement aqueous solution, and (2) load the measurement aqueous solution to a quartz cell (optical path length=10 mm, thickness 1.25 mm), and measure the absorption spectrum using a spectrophotometer (e.g., visible-ultraviolet absorption spectrometer V-670 manufactured by JASCO Corporation).

As the absorption spectrum of the measurement aqueous solution, a corrected absorption spectrum obtained by measuring the absorption spectrum of water alone in advance and deducting this absorption spectrum of water from the absorption spectrum of the measurement aqueous solution is used.

The solubility of the compound A of the present invention in 100 parts by mass of water can be set as appropriate in accordance with the intended use and the like of the compound A of the present invention and, from the standpoint of making it easy to use the compound A as a water-soluble initiator in a composition containing water, the solubility is preferably not less than 0.5 parts by mass, more preferably not less than 0.9 parts by mass, particularly preferably not less than 1.0 part by mass, especially preferably not less than 1.2 parts by mass. Further, the solubility is preferably not less than 2.0 parts by mass, more preferably not less than 3.0 parts by mass, particularly preferably not less than 4.0 parts by mass, especially preferably not less than 5.0 parts by mass. An upper limit of the solubility in water is not particularly restricted since a higher solubility in water is more preferred; however, it is preferably 10 parts by mass or less in 100 parts by mass of water.

Hereinafter, the solubility in water is defined as a dissolved amount that is measured at a point when the compound A of the present invention is no longer dissolved (when floatation, sedimentation, precipitation, or turbidity is observed) after being slowly dissolved in 100 g of deionized water with stirring using a stirrer in an environment having a temperature of 25° C. and a relative humidity (RH) of 65%. Specifically, the measurement is performed by adding the compound in an amount of 0.1 g at a time.

A method of producing the compound A of the present invention may be any method as long as a desired structure can be obtained, and any known method can be employed.

As a method of producing the compound A of the present invention, for example, when the compound A of the present invention has an acidic group salt-containing group, as exemplified in reaction formulae (R1) and (R2) below, a known method is employed, or a commercially available compound containing an acidic group (carboxylic acid group (—COOH) in reaction formulae below) is prepared, and this compound is dissolved or dispersed in an organic solvent, such as methylene chloride, to prepare a solution or a dispersion.

Next, a compound capable of forming a counter cation (a tertiary amine capable of generating a tertiary ammonium cation through abstraction of the hydrogen atom of a carboxylic acid group in reaction formula (R1) below, or an alcohol solution of an alkali metal hydroxide capable of generating an alkali metal cation (KOH alcohol solution) in reaction formula (R2) below) is added to the above-obtained solution or dispersion.

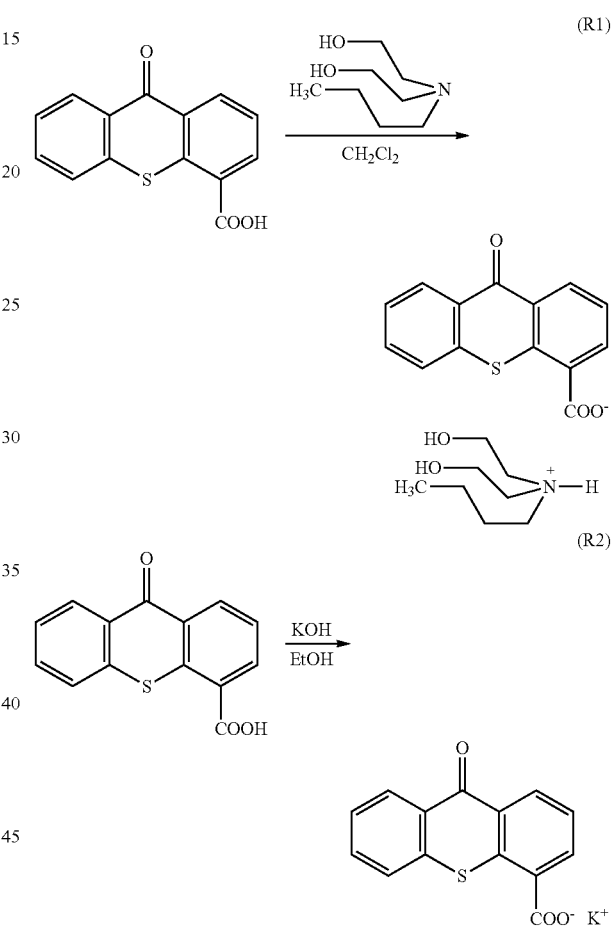

Examples of the use of the compound A of the present invention include radical polymerization initiators that generate radicals when irradiated with light and, particularly, the compound A can be preferably used in a water-soluble radical polymerization initiator that is used in a composition containing water as a solvent, since the compound A can more effectively exert its effect of having excellent solubility in water.

Specific examples of the use of a curable composition in which such a radical polymerization initiator is used include optical materials represented by eyeglasses and imaging lenses; paints; various coating agents; lining agents; inks; resists; liquid resists; adhesives; sealing agents for liquid-crystal dropping method; image-forming materials; pattern-forming materials; printing boards; insulating varnishes; insulating sheets; laminated plates; printed circuit boards; sealants for semiconductor devices, LED packages, liquid crystal inlets, organic ELs, optical elements, electrical insulating materials, electronic components, separator membranes and the like; molding materials; electrodes of secondary batteries; separators; putties; building materials; sidings; glass fiber impregnants; fillers; passivation films for semiconductors, solar cells and the like; interlayer insulating films; protective films; prism lens sheets used in backlights of liquid crystal displays; Fresnel lens sheets used in the screens of projection televisions and the like; lens parts of lens sheets (e.g., lenticular lens sheets) as well as backlights and the like using such sheets; protective films and spacers of liquid crystal color filters; DNA separation chips; microreactors; nano-biodevices; recording materials for hard disks; solid-state image sensing devices; solar cell panels; light-emitting diodes; organic light-emitting devices; luminescent films; fluorescent films; MEMS elements; actuators; holograms; plasmon devices; polarizing plates; polarizing films; optical lenses such as microlenses; optical elements; optical connectors; optical waveguides; casting agents for stereolithography; and curable composition applications that come into contact with the human body, such as dental materials and nail decorations (nails), and examples of a substrate to which the curable composition can be applied as a coating agent include products made of metal, wood material, rubber, plastic, glass, ceramic or the like.

Thereamong, from the standpoint of more effectively exerting an effect of having excellent sensitivity, the curable composition is preferably used in ink applications including thick member applications such as 3D printers as well as colorant-containing colored photocurable ink applications and, from the standpoint of more effectively exerting an effect of having excellent solubility in water, the curable composition is preferably used in low-organic-solvent composition applications, such as curable compositions for nail decoration (nails) and the like that come into contact with the human body.

B. Radical Polymerization Initiator

Next, the radical polymerization initiator of the present invention will be described.

The radical polymerization initiator of the present invention contains a compound represented by the following Formula (A), namely the compound A of the present invention.

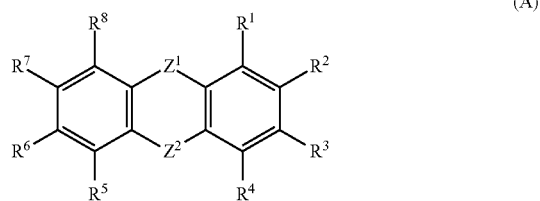

(A)

In Formula (A), $Z^1$ represents a direct bond, $-NR^{101}-$, $-O-$, $-S-$, $-SO-$, or $-CO-$; $Z^2$ represents $-C(R^{102})_2-$, $-NR^{101}-$, $-O-$, $-S-$, $-SO-$, or $-CO-$; $R^1$, $R^2$, $R^3$, $R^4$, $R^5$, $R^6$, $R^7$ and $R^8$ each independently represent a hydrogen atom, CN, $NO_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group, which is represented by the following Formula (B1); at least one of $R^1$, $R^2$, $R^3$, $R^4$, $R^5$, $R^6$, $R^7$ and $R^8$ is the group containing a salt-forming group B; and $R^{101}$ and $R^{102}$ each independently represent a hydrogen atom, an alkyl group having 1 to 20 carbon atoms, an aryl group having 6 to 30 carbon atoms, an arylalkyl group having 7 to 30 carbon atoms, or a heterocycle-containing group having 2 to 20 carbon atoms.

$$*-L_1-(-B)_b \qquad (B1)$$

In Formula (B1), $L_1$ represents a direct bond or a (b+1)-valent linking group; B represents an acidic group salt or a basic group salt; b represents an integer of 1 to 10; and the asterisk (*) represents a site of binding with a benzene ring.

The radical polymerization initiator of the present invention contains the compound A of the present invention and, therefore, has excellent sensitivity and solubility in water.

The radical polymerization initiator of the present invention contains the compound A of the present invention. Components of the radical polymerization initiator of the present invention will now be described in detail.

1. Compound A

The compound A of the present invention is a compound represented by the above-described Formula (A). With regard to this compound A, description thereof is omitted here since the same as described above in the section of "A. Compound" can be applied.

In the radical polymerization initiator, only one, or two or more types of the compound A of the present invention may be contained. The radical polymerization initiator of the present invention can contain, for example, two to five types of the compound A. For example, the radical polymerization initiator of the present invention can contain, as two types of the compound A of the present invention, the compound A having an acidic group salt-containing group and the compound A having a basic group salt-containing group. Alternatively, the radical polymerization initiator of the present invention can contain two types of the compound A, which are the compound A that has a single acidic group salt-containing group and the compound A that has two acidic group salt-containing groups.

The content of the compound A of the present invention is set as appropriate in accordance with the type and the like of the radical polymerization initiator. The content may be 100 parts by mass in 100 parts by mass of the solid content of the radical polymerization initiator, i.e. the radical polymerization initiator of the present invention may consist of only the compound A of the present invention. Alternatively, the content of the compound A of the present invention in 100 parts by mass of the solid content of the radical polymerization initiator may be less than 100 parts by mass, i.e. the radical polymerization initiator may be a composition that contains the compound A of the present invention and other component(s). For example, the content of the compound A can be more than 10 parts by mass but 99 parts by mass or less, preferably 50 parts by mass to 95 parts by mass. It is noted here that the term "solid content" used herein encompasses all components other than a solvent. The reason for such a content of the compound A is because it allows the radical polymerization initiator of the present invention has superior sensitivity and solubility in water.

2. Other Radical Polymerization Initiators

The radical polymerization initiator of the present invention contains the compound A of the present invention and, as required, may further contain a radical polymerization initiator compound other than the compound A of the present invention (hereinafter, also referred to as "other initiator compound"). This is because the use of other initiator compounds in combination with the compound A of the present invention allows the radical polymerization initiator of the present invention to effectively absorb light in a long wavelength range and to have superior sensitivity.

In the radical polymerization initiator of the present invention, the above-described other initiator compounds are preferably soluble in water and, particularly, their solubility in 100 parts by mass of water is preferably not less than 0.5 parts by mass, more preferably not less than 1 part by mass, still more preferably not less than 2 parts by mass, yet still more preferably not less than 10 parts by mass, particularly preferably not less than 30 parts by mass, especially preferably not less than 50 parts by mass. This is because it allows the compound A of the present invention to more effectively exert its effect of having excellent solubility in water. This also makes the radical polymerization initiator useful for an aqueous composition. The higher the upper limit of the solubility, the more preferred it is, and the upper limit of the solubility is not particularly restricted; however, it may be, for example, 1,000 parts by mass or less, preferably 300 parts by mass or less.

Such other initiator compounds may be any compound other than the compound A of the present invention, and any known radical polymerization initiator can be used. Examples of the other initiator compounds include the radical polymerization initiators that are described in JP2016-176009A.

Examples of commercially available products of the other initiator compounds include N-1414, N-1717, N-1919, PZ-408, NCI-831, NCI-930, and SP-246 (which are manufactured by ADEKA Corporation); IRGACURE 184, IRGACURE 2959, IRGACURE 1173, IRGACURE 369, IRGACURE 907, IRGACURE 651, IRGACURE 379EG, IRGACURE 819, IRGACURE 754, IRGACURE TPO, IRGACURE OXE 01, IRGACURE OXE, 02, IRGACURE OXE: 03, IRGACURE OXE 04, IRGACURE 127, IRGACURE MBE, and IRGACURE 500 (which are manufactured by BASF Japan, Ltd.); TR-PBG-304, TR-PBG-305, TR-PBG-309, TR-PBG-311, TR-PBG-314, TR-PBG-315, TR-PBG-327, TR-HABI 101, TR-HABI 102, TR-HABI 103, TR-HABI 104, TR-HABI 105, TR-HABI 106, TR-HABI 107, TR-OBM, TR-BDK, TR-EDB, TR-EHA, TR-DMB, TR-PTSA, TR-4MBP, TR-BMS, TR-MBF, TR-EMK, TR-NPG, and TR-LCV (which are manufactured by Changzhou Tronly New Electronic Materials Co., Ltd.); and SPI-02 and SPI-03 (which are manufactured by Samyang Corporation).

Among the above-described compounds, the other initiator compounds are preferably compounds represented by Formula (I) below (hereinafter, also referred to as "compound I"). This is because the compound I has excellent solubility in water and allows the compound A of the present invention to more effectively exert its effect of having excellent solubility in water. In addition, the compound I can more effectively absorb light in a long wavelength range and thus exhibits superior sensitivity when used in combination with the compound A of the present invention.

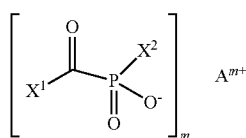

In Formula (I), $X^1$ represents an aryl group having 6 to 15 carbon atoms; $X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or aryl group having 6 to 15 carbon atoms; $A^{m+}$ represents an m-valent cationic component; and m represents an integer of 1 to 3.

The hydrogen atoms in the aryl group having 6 to 15 carbon atoms that is used as $X^1$ in Formula (I) may be unsubstituted, or may be substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, or a branched halogenated alkoxy group having 3 to 8 carbon atoms.

In Formula (I), $X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms.

The hydrogen atoms in the aryl group having 6 to 15 carbon atoms that is used as $X^2$ may be unsubstituted, or may be substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, a branched halogenated alkoxy group having 3 to 8 carbon atoms, a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group. A methylene group in the group represented by $X^2$ may be substituted with an oxygen atom or a sulfur atom.

Examples of the aryl group having 6 to 15 carbon atoms that is used as $X^1$ and $X^2$ include phenyl, trimethylphenyl, tolyl, xylyl, naphthyl, and anthryl.

Examples of the linear alkyl group having 1 to 8 carbon atoms that is used as $X^1$ and $X^2$ as well as a substituent for substituting a hydrogen atom of $X^1$ and $X^2$ include methyl, ethyl, propyl, butyl, amyl, hexyl, heptyl, and octyl.

Examples of the branched alkyl group having 3 to 8 carbon atoms that is used as $X^1$ and $X^2$ as well as a substituent for substituting a hydrogen atom of $X^1$ and $X^2$ include isopropyl, butyl, isobutyl, s-butyl, t-butyl, isoamyl, t-amyl, isooctyl, 2-ethylhexyl, and t-octyl.

The linear halogenated alkyl group having 1 to 8 carbon atoms, which is used as $X^1$ and $X^2$ as well as a substituent for substituting a hydrogen atom of $X^1$ and $X^2$, represents the above-described linear alkyl group having 1 to 8 carbon atoms in which at least one hydrogen atom is substituted with a halogen atom.

The branched halogenated alkyl group having 3 to 8 carbon atoms, which is used as $X^1$ and $X^2$ as well as a substituent for substituting a hydrogen atom of $X^1$ and $X^2$, represents the above-described linear alkyl group having 3 to 8 carbon atoms in which at least one hydrogen atom is substituted with a halogen atom.

Examples of the linear alkoxy group having 1 to 8 carbon atoms that is used as $X^1$ and $X^2$ as well as a substituent for substituting a hydrogen atom of $X^1$ and $X^2$ include methoxy, ethoxy, n-propoxy, n-butoxy, t-butoxy, n-pentyloxy, n-hexyloxy, and n-octyloxy.

Examples of the branched alkoxy group having 3 to 8 carbon atoms that is used as $X^1$ and $X^2$ as well as a substituent for substituting a hydrogen atom of $X^1$ and $X^2$ include isopropoxy, isobutoxy, cyclobutoxy, t-butoxy, isopentyloxy, neopentyloxy, and isooctyloxy.

The linear halogenated alkoxy group having 1 to 8 carbon atoms, which is used as $X^1$ and $X^2$ as well as a substituent for substituting a hydrogen atom of $X^1$ and $X^2$, represents the above-described linear alkoxy group having 1 to 8 carbon atoms in which at least one hydrogen atom is substituted with a halogen atom.

The branched halogenated alkoxy group having 3 to 8 carbon atoms, which is used as $X^1$ and $X^2$ as well as a substituent for substituting a hydrogen atom of $X^1$ and $X^2$, represents the above-described linear alkoxy group having 3 to 8 carbon atoms in which at least one hydrogen atom is substituted with a halogen atom.

Examples of the halogen atom used in the halogenated alkyl group and the halogenated alkoxy group used as $X^1$ and $X^2$ and the halogen atom used as a substituent for substituting a hydrogen atom of the groups represented by $X^1$ and $X^2$ include a fluorine atom, a chlorine atom, a bromine atom, and an iodine atom.

In the compound I of the present invention, $X^1$ is preferably phenyl, tolyl, xylyl, 2,4,6-trimethylphenyl, or naphthyl. This is because, with $X^1$ being any of these groups, the compound I has excellent stability, absorption wavelength, and solubility in water. Particularly, in the compound I of the present invention, $X^1$ is preferably a 2,4,6-trimethylphenyl group. This is because it allows the compound I of the present invention to have superior sensitivity.

In the compound I of the present invention, $X^2$ is preferably an aryl group having 6 to 15 carbon atoms, particularly phenyl, tolyl, xylyl, 2,4,6-trimethylphenyl, or naphthyl. This is because, with $X^2$ being any of these groups, the compound I has excellent stability, absorption wavelength, and solubility in water. Particularly, in the present invention, $X^2$ is preferably a phenyl group. This is because it allows the compound I of the present invention to have superior sensitivity.

The above-described m represents a number of 1 to 3 and, from the standpoint of the solubility in water, m is preferably an integer of 1 or 2, more preferably an integer of 1.

The above-described $A^{m+}$, which an m-valent cationic component, is capable of forming a counter ion with acylphosphinic acid. The cationic component may be any component that is capable of imparting the compound I of the present invention with the desired solubility in water and, for example, it may be the same as the cationic component described above in the section of "(1-1) Acidic Group Salt" in "(1) Salt-forming Group B" under "1. Group Containing Salt-forming Group" of "A. Compound".

When the compound A of the present invention contains an acidic group salt as the salt-forming group B, the cationic component is preferably the same cation as the cationic component constituting the acidic group salt in the compound A of the present invention. This is because such a cationic component allows the radical polymerization initiator of the present invention to exhibit excellent dispersion stability with only minor aggregation or precipitation when, for example, mixed with a solvent, a resin or the like.

In the radical polymerization initiator of the present invention, the cationic component is preferably an alkali metal ion, an alkaline earth metal ion, or an amine cation, more preferably an alkali metal ion or a tertiary ammonium cation represented by the above-described Formula (C3) (cation C3), particularly preferably an alkali metal ion or a cation C3, especially preferably a cation C3. This is because, with the cationic component being a cation C3, the compound I of the present invention has superior sensitivity and solubility in water. In addition, a combination of the compound I of the present invention with the compound A of the present invention allows the radical polymerization initiator of the present invention to have superior sensitivity.

The content of the above-described other initiator compound can be set as appropriate in accordance with the intended use and the like of the radical polymerization initiator of the present invention, and it may be, for example, in a range of 1 part by mass to 1,000 parts by mass, preferably 100 parts by mass to 800 parts by mass, particularly preferably 200 parts by mass to 600 parts by mass, with respect to 100 parts by mass of the compound A of the present invention.

3. Radical Polymerization Initiator

The radical polymerization initiator of the present invention may also contain a component other than the compound A of the present invention and the above-described other initiator compound. Examples of such other component include the same ones as those described below in the sections of "2. Radical Polymerizable Compound", "4. Solvent", "5. Resin Component" and "6. Other Components" under "C. Composition". Thereamong, as other component, the radical polymerization initiator of the present invention preferably contains a non-photosensitive resin described in the section of "5. Resin Component". This is because it allows the radical polymerization initiator of the present invention to have excellent moldability and storage stability.

In the radical polymerization initiator of the present invention, the content of a solvent is preferably low and, for example, in 100 parts by mass of the radical polymerization initiator, the solvent content is preferably 10 parts by mass or less, more preferably 5 parts by mass or less, particularly preferably 1 part by mass. This is because such a low solvent content makes it easy to perform a curing treatment of a composition to which the radical polymerization initiator of the present invention is added.

A method of producing the radical polymerization initiator of the present invention may be any method as long as the above-described components can be mixed in the desired amounts, and any known mixing method can be employed. As for the use of the radical polymerization initiator of the present invention, for example, the radical polymerization initiator of the present invention can be used in a curable composition that is to be cured by photoirradiation or the like. Specific use of the curable composition may be the same as described above in the section of "A. Compound".

C. Composition Next, the composition of the present invention will be described.

The composition of the present invention contains the above-described compound A represented by Formula (A) and a radical polymerizable compound.

According to the composition of the present invention, by using the compound A of the present invention, a composition that has excellent sensitivity and a low organic solvent content can be easily obtained. Components of the composition of the present invention will now be described in detail.

1. Compound A

The compound A of the present invention may have any maximum absorption wavelength in a range of 300 nm to 600 nm as long as the compound A is capable of absorbing an exposure light to generate a radical; however, the maximum absorption wavelength is preferably 380 nm or longer. With regard to a more preferred range of the maximum absorption wavelength of the compound A of the present invention, description thereof is omitted here since the same as described above in the section of "A. Compound" can be applied.

The content of the compound A of the present invention is not particularly restricted as long as the composition can be imparted with the desired curability and the like. The content may be, for example, 0.05 parts by mass to 10 parts by mass, preferably 0.1 parts by mass to 5 parts by mass, with respect to 100 parts by mass of the solid content of the composition. It is noted here that the term "solid content" used herein encompasses all components other than a solvent.

In the composition of the present invention, only one, or two or more types of the compound A of the present invention may be contained and, for example, the composition of the present invention can contain two to five types of the compound A. With regard to the compound A of the present invention, description thereof is omitted here since the same as described above in the section of "B. Radical Polymerization Initiator" can be applied.

2. Radical Polymerizable Compound

The radical polymerizable compound according to the composition of the present invention is a compound which has a radical polymerizable group and can be polymerized by a radical. Examples of the radical polymerizable group include ethylenically unsaturated double bond-containing groups, such as a (meth)acryl group, a methacryl group, and a vinyl group. The use of the term "(meth)acryl" is meant to encompass acryl and methacryl. Further, the use of the term "(meth)acrylate" is meant to encompass acrylate and methacrylate.

The radical polymerizable compound according to the composition of the present invention may be a compound having an acid value, or a compound having no acid value. Examples of the compound having an acid value include carboxyl group-containing compounds. By incorporating a compound having an acid value into the radical polymerizable compound according to the composition of the present invention, the composition is imparted with excellent dispersion stability when it contains water as a solvent.

In addition, the solubility of a photoirradiated part into an alkaline developer is reduced. Therefore, the composition of the present invention can be used as, for example, a photosensitive composition whose solubility in a solvent such as an alkaline developer changes before and after photoirradiation. More specifically, by containing a compound having an acid value, the composition of the present invention can be used as a negative-type composition.

As the alkaline developer, an aqueous solution generally used as an alkaline developer, such as a tetramethyl ammonium hydroxide (TMAH) aqueous solution or a potassium hydroxide aqueous solution, can be used.

Examples of the compound having an acid value include (meth)acrylate compounds containing a carboxyl group or the like, such as (meth)acrylic acid.

Examples of the compound having no acid value include (meth)acrylate compounds containing no carboxyl group or the like, such as epoxy acrylate resins and 2-hydroxyethyl (meth)acrylate.

In the composition of the present invention, the radical polymerizable compound may be used individually, or two or more thereof may be used in combination. As the radical polymerizable compound, for example, a combination of a compound that contains an ethylenically unsaturated double bond group and has an acid value and a compound that contains an ethylenically unsaturated double bond group and has no acid value can be used. In the composition of the present invention, when two or more radical polymerizable compounds are used in combination, they may be copolymerized in advance to be used as a copolymer. More specific examples of such radical polymerizable compounds include those described in Japanese Unexamined Patent Application Publication No. 2016-176009.

In the composition of the present invention, the content of the radical polymerizable compound is not particularly restricted as long as the composition can yield a cured product having the desired strength, and it may be, for example, 10 parts by mass to 99 parts by mass with respect to 100 parts by mass of the solid content of the composition. This is because, with the content of the radical polymerizable compound being in this range, the composition of the present invention can, for example, maintain the compound A of the present invention in a stable manner.

3. Other Radical Polymerization Initiators

The composition of the present invention contains the compound A and, as required, may further contain a radical polymerization initiator compound other than the compound A (hereinafter, also referred to as "other initiator compound"). With regard to the content, the type and the like of the other initiator compound, description thereof is omitted here since the same as described above in the section of "2. Other Radical Polymerization Initiator" under "B. Radical Polymerization Initiator" can be applied.

4. Solvent

The composition of the present invention contains the compound A of the present invention and the radical polymerizable compound and, as required, may further contain a solvent. The solvent is one that is capable of dispersing or dissolving the respective components, such as the compound A of the present invention and the radical polymerizable compound. Accordingly, even in a liquid state at normal temperature (25° C.) under atmospheric pressure, the solvent contains neither the compound A of the present invention nor the radical polymerizable compound. As the solvent, water and an organic solvent can both be used. The solvent preferably contains water from the standpoints of, for example, reducing the environmental load and the effects on the human body as well as, when the composition is to be applied onto an organic material, inhibiting the dissolution of the organic material.

In the composition of the present invention, the water content in 100 parts by mass of the solvent is preferably not less than 50 parts by mass, more preferably not less than 80 parts by mass, particularly preferably not less than 90 parts by mass, especially preferably 100 parts by mass (i.e. the composition of the present invention contains only water as a solvent). This is because, with the water content being in this range, the composition of the present invention is superior in terms of, for example, reducing the environmental load and the effects on the human body as well as, when the composition is to be applied onto an organic material, inhibiting the dissolution of the organic material.

Examples of an organic solvent that can be used as the solvent in the composition of the present invention include ketones, such as methyl ethyl ketone, methyl amyl ketone, diethyl ketone, acetone, methyl isopropyl ketone, methyl isobutyl ketone, cyclohexanone, and 2-heptanone; ether-based solvents, such as ethyl ether, dioxane, tetrahydrofuran, 1,2-dimethoxyethane, 1,2-diethoxyethane, and dipropylene glycol dimethyl ether; ester-based solvents, such as methyl acetate, ethyl acetate, n-propyl acetate, isopropyl acetate, n-butyl acetate, cyclohexyl acetate, ethyl lactate, dimethyl succinate, and TEXANOL; cellosolve-based solvents, such as ethylene glycol monomethyl ether and ethylene glycol monoethyl ether; alcohol-based solvents, such as methanol, ethanol, iso- or n-propanol, iso- or n-butanol, and amyl alcohol; ether ester-based solvents, such as ethylene glycol monomethyl acetate, ethylene glycol monoethyl acetate, propylene glycol-1-monomethyl ether (PGM), propylene glycol 1-monomethyl ether-2-acetate (PGMEA), dipropylene glycol monomethyl ether acetate, 3-methoxybutyl acetate, and ethoxyethyl propionate; aromatic solvents, such as benzene, toluene, and xylene; aliphatic hydrocarbon-based solvents, such as hexane, heptane, octane, and cyclohexane; terpene-based hydrocarbon oils, such as turpentine oil, D-limonene, and pinene; paraffin-based solvents, such as mineral spirit, SWASOL #310 (manufactured by COSMO Matsuyama Oil Co., Ltd.) and SOLVESSO #100 (manufactured by Exon Chemical Co., Ltd.); halogenated aliphatic hydrocarbon-based solvents, such as carbon tetrachloride, chloroform, trichloroethylene, methylene chloride, and 1,2-dichloroethane; halogenated aromatic hydrocarbon-based solvents, such as chlorobenzene; carbitol-based solvents; aniline; triethylamine; pyridine; acetic acid; acetonitrile; carbon disulfide; N,N-dimethylformamide; N,N-dimethylacetamide; N-methylpyrrolidone; and dimethyl sulfoxide. The organic solvent is preferably an alcohol-based solvent because of its good compatibility with water.

In the composition of the present invention, the solvent content can be set as appropriate in accordance with the intended use and the like of the composition of the present invention and may be, for example, not less than 10 parts by mass, preferably 50 parts by mass to 95 parts by mass, in 100 parts by mass of the composition of the present invention. This is because such a solvent content makes it easy to adjust the coating film thickness.

5. Resin Component

The composition of the present invention may also contain a resin component other than the radical polymerizable compound. Examples of the resin component include: polymerizable group-containing polymerizable compounds, such as cationically polymerizable compounds and anionically polymerizable compounds; and polymers having no polymerizable group.

The content of the resin component, which is selected as appropriate in accordance with the purpose of its use, is not particularly restricted and may be, for example, 10 parts by mass to 90 parts by mass with respect to 100 parts by mass of the solid content of the composition. A total content of the resin component and the radical polymerizable compound, which is selected as appropriate in accordance with the purpose of their use, is not particularly restricted and may be, for example, 10 parts by mass to 99 parts by mass with respect to 100 parts by mass of the solid content of the composition.

(1) Cationically Polymerizable Compound

In the composition of the present invention, a cationically polymerizable compound may have one or more polymerizable groups that can be cationically polymerized, and a monofunctional compound having one of such a polymerizable group, or a polyfunctional compound having two or more of such polymerizable groups can be used.

Examples of the cationically polymerizable compound include: cyclic ether group-containing compounds, such as epoxy group-containing epoxy compounds and oxetane group-containing oxetane compounds; and vinyl ether group-containing vinyl ether compounds. More specific examples of the cationically polymerizable compound include those described in Japanese Unexamined Patent Application Publication No. 2016-176009. When two or more cationically polymerizable compounds are used in combination, they may be copolymerized in advance to be used as a copolymer. The cationically polymerizable compound(s) can be used together with a cationic initiator, such as a photocationic initiator or a thermal cationic initiator.

(2) Anionically Polymerizable Compound

In the composition of the present invention, an anionically polymerizable compound may have one or more polymerizable groups that can be anionically polymerized, and a monofunctional compound having one of such a polymerizable group, or a polyfunctional compound having two or more of such polymerizable groups can be used. Examples of the anionically polymerizable compound include epoxy group-containing epoxy compounds, lactone group-containing lactone compounds, and (meth)acryl group-containing compounds.

Examples of the lactone compounds include β-propiolactone and ε-caprolactone. As the epoxy compounds, those exemplified above for the cationically polymerizable compound can be used. Further, as the (meth)acryl group-containing compounds, those exemplified above for the radical polymerizable compound can be used. When two or more anionically polymerizable compounds are used in combination, they may be copolymerized in advance to be used as a copolymer.

(3) Photosensitive Group-Containing Compound

In the composition of the present invention, as a polymerizable compound, a compound that contains a photosensitive group having a photodimerizable unsaturated bond (hereinafter, also referred to as "photosensitive group-containing compound") can be used as well. The photosensitive group and the photosensitive group-containing compound containing the same may be the same as described in Japanese Unexamined Patent Application Publication No. 2016-193985.

More specific examples of the photosensitive group include a stilbazolium group and a cinnamoyl group.

The photosensitive group-containing compound is preferably, for example, a compound having a hydroxy group. This is because such a photosensitive group-containing compound has excellent solubility in water.

(4) Polymer Having No Polymerizable Group

The above-described polymer has no polymerizable group. This polymer may be any polymer that contains a repeating structure, and examples thereof include a photosensitive resin having a photosensitivity and a non-photosensitive resin having no photosensitivity.

(4-1) Photosensitive Resin

The above-described photosensitive resin has a photosensitivity, and examples thereof include positive-type resins that are used in combination with an acid generator and changed toward having an increased solubility in a developer through, for example, cleavage of a chemical bond of an ester group, an ether group or the like caused by the action of an acid. As the positive-type resins, for example, the resist base resins or compounds that are described in Japanese Unexamined Patent Application Publication No. 2016-89085 can be used.

(4-2) Non-Photosensitive Resin

The above-described non-photosensitive resin may be any resin that has no photosensitivity, and examples thereof include thermoplastic resins, such as polycarbonates (PC), polyethylene terephthalates (PET), polyether sulfones, polyvinyl butyrals, polyphenylene ethers, polyamides, polyamide imides, polyether imides, norbornene-based resins, acrylic resins, methacrylic resins, isobutylene-maleic anhydride copolymer resins, cyclic olefin resins, polyvinyl alcohols, polyethylene glycols, and polyvinylpyrrolidones.

As a polyvinyl alcohol, for example, a polyvinyl alcohol that is generally referred to as "poval" and obtained by polymerization of vinyl alcohol, a partially saponified polyvinyl alcohol, a completely saponified polyvinyl alcohol, or a saponification product of a copolymer composed of vinyl acetate and a copolymerizable monomer can be used. In addition, modified polyvinyl alcohols obtained by modifying these polyvinyl alcohols with various functional groups can be used as well. As the modified polyvinyl alcohols, for example, the acetoacetate group-containing polyvinyl alcohols that are described in Japanese Unexamined Patent Application Publication No. 2009-113347 can be used. As the non-photosensitive resin, a polymerization product of a polymerizable compound can be used as well. In other words, the composition of the present invention may be a cured product of a composition containing a polymerizable compound.

(4-3) Polymer

The weight-average molecular weights (Mw) of these polymers can be set as appropriate in accordance with the intended use and the like of the composition of the present invention and may be, for example, 1,500 or higher, or 1,500 to 300,000. The weight-average molecular weight Mw can be measured using, for example, HLC-8120GPC manufactured by Tosoh Corporation along with N-methylpyrrolidone added with 0.01 mol/L of lithium bromide as an elution solvent, polystyrenes having a Mw of 377,400, 210,500, 96,000, 50,400, 20,650, 10,850, 5,460, 2,930, 1,300, or 580 (EASI PS-2 Series, manufactured by Polymer Laboratories, Ltd.) and a polystyrene having a Mw of 1,090,000 (manufactured by Tosoh Corporation) as polystyrene standards for a calibration curve, and two TSK-GEL ALPHA-M columns (manufactured by Tosoh Corporation) as measurement columns. The measurement temperature and the flow rate can be set at 40° C. and 1.0 mL/min, respectively.

6. Other Components

The composition of the present invention may contain other component(s) as required in addition to the compound A of the present invention, the radical polymerizable compound, other polymerization initiator, the solvent, and the resin component. Examples of the other components include polymerization initiators, such as a cationic polymerization initiator that can be added along with a cationically polymerizable compound or can be added as an acid generator along with a photosensitive compound, or an anionic polymerization initiator that can be added along with an anionically polymerizable compound.

As the cationic polymerization initiator and the like, more specifically, for example, the cationic initiators and the like that are described in Japanese Unexamined Patent Application Publication No. 2016-176009 can be used. Further, more specific examples of the anionic polymerization initiator and the like include the photoanionic polymerization initiators, thermal anionic polymerization initiators and the like that are described in Japanese Unexamined Patent Application Publication No. 2017-073389.

In addition to the above-described polymerization initiators, examples of the other components also include additives, such as a colorant, an inorganic compound, a dispersant for dispersing a colorant and an inorganic compound, a chain transfer agent, a sensitizer, a surfactant, a silane coupling agent, and melamine.

As the additives, known materials such as those described in WO 2014/021023 can be used.

In addition to the above-described compounds, the composition of the present invention may also contain, as required, a salt component such as sodium chloride, potassium chloride, ammonium chloride, sodium acetate, sodium nitrate, lithium chloride, ammonium sulfate, sodium sulfate, lithium sulfate, or potassium sulfate. The content of the other components, which is selected as appropriate in accordance with the purpose of their use, is not particularly restricted and may be, for example, a total of 50 parts by mass or less with respect to 100 parts by mass of the solid content of the composition.

7. Composition

A method of producing the composition of the present invention may be any method as long as the above-described components can be mixed in the desired amounts, and any known mixing method can be employed. As for the use of the composition of the present invention, for example, the composition of the present invention can be used as a photocurable composition that is cured by photoirradiation. Specific use of the composition of the present invention may be the same as described above in the section of "A. Compound".

D. Cured Product

Next, the cured product of the present invention will be described.

The cured product of the present invention is a cured product of the composition of the present invention. The cured product of the present invention will now be described in detail. With regard to the composition of the present invention, the same as described above in the section of "C. Composition" can be applied.

The cured product of the present invention is composed of the composition of the present invention and contains at least a polymer of a radical polymerizable compound. The content of the polymer of the radical polymerizable compound may be the same as that of the radical polymerizable compound described above in the section of "C. Composition".

The cured product of the present invention can contain substantially no solvent. The content of a solvent in the cured product of the present invention may be, for example, 1 part by mass or less, preferably 0.5 parts by mass or less, with respect to 100 parts by mass of the cured product. This is because, with the solvent content being in this range, the cured product of the present invention exhibits excellent stability over time.

The plan view shape, the thickness and the like of the cured product of the present invention can be set as appropriate in accordance with the intended use and the like of the cured product of the present invention.

A method of producing the cured product of the present invention is not particularly restricted as long as a cured product of the composition of the present invention can be formed in a desired shape. With regard to this production method, description thereof is omitted here since, for example, the same as described below in the section of "E. Method of Producing Cured Product" can be applied.

With regard to the use and the like of the cured product of the present invention, the same as described above in the section of "A. Compound" can be applied.

E. Method of Producing Cured Product

Next, the method of producing a cured product according to the present invention will be described.

The method of producing a cured product according to the present invention includes the step of irradiating the composition of the present invention with light. The steps in this production method of the present invention will now be described in detail.

1. Photoirradiation Step

This step is the step of irradiating the composition of the present invention with light. In this step, the light irradiated to the composition of the present invention may be any light as long as it can cause the compound A of the present invention to generate a radical. As for the wavelength of the light, in order to allow the light to sufficiently penetrate into the inside, the light has a wavelength peak of preferably 300 mu to 500 nm, more preferably 350 nm to 500 nm, particularly preferably 380 nm to 480 nm, especially preferably 400 nm to 470 nm.

The amount of the light to be irradiated may be any amount as long as a cured product having a desired hardness can be formed, and it is adjusted as appropriate in accordance with the thickness and the like of a coating film of the composition of the present invention. The intensity of the light is, for example, preferably 10 mW/cm$^2$ to 300 mW/cm$^2$, more preferably 25 mW/cm$^2$ to 100 mW/cm$^2$, and the irradiation time may be preferably 5 seconds to 500 seconds, more preferably 10 seconds to 300 seconds.

Examples of a light source for this photoirradiation include ultrahigh-pressure mercury lamps, mercury vapor arc lamps, carbon arc lamps, xenon arc lamps, and LED light sources.

As the light to be irradiated, a laser light may be used. As the laser light, one containing a light having a wavelength of 340 nm to 430 nm can be used. As a source of this laser light, a light source which emits a light of the visible to the infrared region, such as an argon ion laser, a helium neon laser, a YAG laser, or a semiconductor laser can be used as well. When any of these lasers is used, the composition of the present invention may contain a sensitizing dye that absorbs the light of the visible to the infrared region.

In the method of producing a cured product according to the present invention, as a photoirradiation method, a method of irradiating a light to the entire surface or a part of a coating film of the composition of the present invention in a plan view may be employed. When the coating film is to be partially irradiated with a light, as the photoirradiation method, for example, a method of irradiating a light through a mask or the like, or a method of irradiating a light only to the part of the composition to be cured may be employed.

With regard to the composition of the present invention, the same as described above in the section of "C. Composition" can be applied. For the formation of a cured product, the composition of the present invention usually contains a polymerizable compound.

2. Other Steps

The method of producing a cured product according to the present invention includes the photoirradiation step and may also include other steps as required. Examples of the other steps include the step of forming a coating film of the composition of the present invention before the photoirradiation step, the developing step performed after the photoirradiation step, the step of removing a solvent after the step of forming the coating film, and the heating step (post-baking step) performed after the photoirradiation step. Further, when the composition of the present invention contains a thermal polymerization initiator, such as a thermal radical polymerization initiator, a thermal cationic polymerization initiator or a thermal anionic polymerization initiator, the method may also include the step of heat-curing the composition of the present invention before or after the photoirradiation step.

The step of forming a coating film may be performed by any method as long as a coating film of the composition that has a desired thickness can be obtained and, for example, a known method of spin coating, roll coating, bar coating, die coating, curtain coating, printing, immersion or the like can be employed.

A substrate on which a coating film of the composition of the present invention is formed can be set as appropriate in accordance with the intended use and the like of the resulting cured product, and examples thereof include a soda glass, a quartz glass, a semiconductor substrate, a metal substrate, a piece of paper, and a plastic substrate. The cured product formed on such a substrate may be detached from the substrate before the use or transferred from the substrate to another substrate before the use.

A development method in the developing step may be any method that can remove uncured composition and, for example, a known development method such as a method of removing uncured composition using an alkaline developer can be employed.

As a solvent removal method in the step of removing a solvent, any method that can adjust the resulting cured product to have a desired solvent content, and examples thereof include a heating method, namely a method of performing a prebaking process as the step of removing the solvent.

The heating temperature in the heating step (post-baking step) performed after the photoirradiation step may be any temperature as long as the mechanical strength of the cured product can be improved, and it can be set as appropriate in accordance with the type, the intended use and the like of the cured product.

3. Other

With regard to the cured product produced by the method of producing a cured product according to the present invention as well as the use and the like thereof, the same as described above in the section of "D. Cured Product" can be applied.

The radical polymerization initiator of the present invention, a composition containing the same, a cured product of the composition, a method of producing the cured product, and the compound of the present invention are not restricted to the above-described embodiments. The above-described embodiments are merely examples, and any embodiment that has substantially the same constitution as the technical idea described in the claim of the present invention and exerts comparable actions and effects is included in the technical scope of the present invention.

EXAMPLES

I. Evaluation of Compounds

Example 1-1

In 100 mL of methylene chloride, 10.0 g of 9-oxo-thioxanthene-4-carboxylic acid was dispersed, and 7.0 g of N-butyldiethanolamine was added thereto at room temperature. The resultant was stirred for 30 minutes to obtain a homogeneous solution. This solution was concentrated using a rotary evaporator and then washed with 100 mL of diethyl ether, whereby 15.5 g of a compound represented by the below-described Formula (61) was obtained. The NMR and IR results of the thus obtained compound are shown in Tables 1 and 2 below.

Example 1-2

In 100 mL of methylene chloride, 10.0 g of 9-oxo-thioxanthene-4-carboxylic acid was dispersed. A solution obtained by dissolving 2.4 g of KOH in 42 mL of ethanol was added thereto at room temperature. The resultant was stirred for 30 minutes to obtain a homogeneous solution. This solution was concentrated using a rotary evaporator and then washed with 100 mL of diethyl ether, whereby 11.1 g of a compound represented by Formula (1) below was obtained. The NMR and IR results of the thus obtained compound are shown in Tables 1 and 2 below.

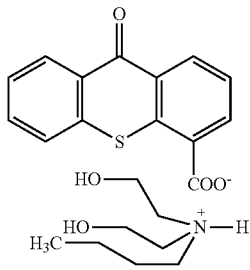

(61)

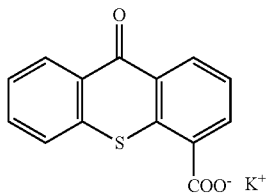

(1)

Comparative Example 1-1

As a radical polymerization initiator, a compound represented by the below-described Formula (101) (IRGACURE 2959 manufactured by BASF Japan, Ltd.; hereinafter also referred to as "Compound 101") was prepared.

Comparative Example 1-2

As a radical polymerization initiator, a compound represented by the below-described Formula (102) (IRGACURE 184 manufactured by BASF Japan, Ltd.; hereinafter also referred to as "Compound 102") was prepared.

Comparative Example 1-3

As a radical polymerization initiator, a compound represented by the below-described Formula (103) (benzophenone; hereinafter also referred to as "Compound 103") was prepared.

Comparative Example 1-4

As a radical polymerization initiator, a compound represented by the below-described Formula (104) (camphor quinone; hereinafter also referred to as "Compound 104") was prepared.

Comparative Example 1-5

To a reaction flask, 5.0 g (17.3 mmol) of phenyl(2,4,6-trimethylbenzoyl)phosphinic acid and 50 ml of dichloromethane were added, and these materials were completely dissolved with stirring at room temperature. Then, 2.8 g (17.3 mmol) of N-butyldiethanolamine was further added, and the resultant was continuously stirred for 5 hours at room temperature. This reaction solution was desolvated and solidified by cooling to 10° C. or lower, and the resulting residue was washed with hexane and then dried under a reduced pressure, whereby an acylphosphinate represented by the below-described Formula (105) (hereinafter, also referred to as "Compound 105") was obtained as pale yellow crystals in an amount of 7.5 g (yield: 97.4%). It is note here that this acrylphosphinate is a compound which corresponds to the above-described compound I and functions as a radical polymerization initiator.

Comparative Example 1-6

As a radical polymerization initiator, a compound represented by the below-described Formula (106) (thioxanthone carboxylic acid; hereinafter also referred to as "Compound 106") was prepared.

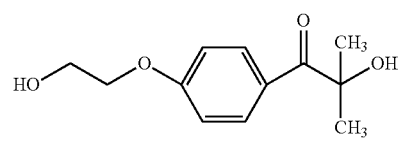

(101)

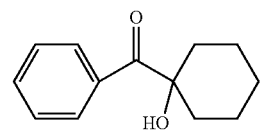

(102)

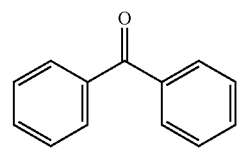

(103)

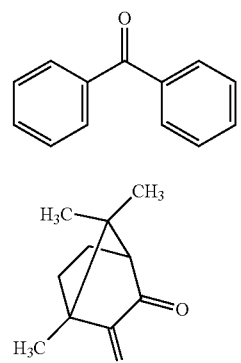

(104)

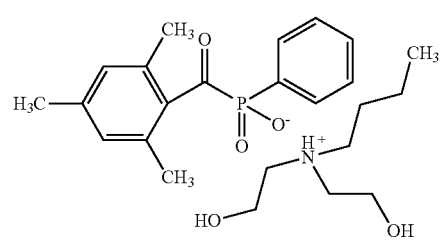

(105)

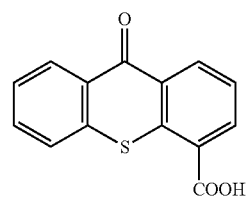

(106)

TABLE 1

| | Chemical shift/ppm (multiplicity, number of protons) in CDCl$_3$ |
|---|---|
| Example 1-1 (Compound 61) | 0.98 (t, 3H), 1.43 (sext, 2H), 1.81 (m, 2H), 3.2-3.3 (m, 6H), 4.1 (m, 4H), 7.4-7.7 (m, 4H), 8.3-8.5 (m, 2H), 8.81 (dd, 1H), 7.0-8.0 (brs, 1H) |
| Example 1-2 (Compound 1) | 7.4-7.7 (m, 5H), 8.3-8.5 (m, 1H), 8.84 (dd, 1H) |

TABLE 2

| | IR absorption spectrum/cm$^{-1}$ |
|---|---|
| Example 1 (Compound 61) | 610, 620, 647, 675, 703, 739, 770, 838, 911, 964, 1010, 1034, 1056, 1108, 1079, 1159, 1173, 1226, 1292, 1327, 1396, 1446, 1495, 1566, 1598, 1631, 3255 |
| Example 2 (Compound 1) | 621, 629, 645, 670, 708, 737, 770, 808, 863, 963, 1054, 1054, 1108, 1079, 1159, 1173, 1192, 1295, 1333, 1389, 1443, 1571, 1592, 1607, 1645, 3047, 3411 |

[Evaluation]

The compounds obtained in Examples and Comparative Examples were evaluated as follows.

1. Solubility in Water

In an environment having a temperature of 25° C. and a relative humidity (RH) of 65%, while stirring 100 g of deionized water using a stirrer, each of the compounds obtained in Examples and Comparative Examples was slowly dissolved therein in an amount of 0.1 g at a time, and the dissolved amount was measured at a point when the compound was no longer dissolved (when floatation, sedimentation, precipitation, or turbidity was observed) to determine the solubility in water (parts by mass). The results thereof are shown in Table 3 below.

2. Maximum Absorption Wavelength (1) The compounds obtained in Examples and Comparative Examples were each dissolved in deionized water to obtain 0.1%-by-mass aqueous solutions as measurement aqueous solutions.

(2) The thus obtained measurement aqueous solutions were each loaded to a quartz cell (optical path length—10 mm, thickness 1.25 mm), and an absorption spectrum was measured using a spectrophotometer (e.g., visible-ultraviolet absorption spectrometer V-670 manufactured by JASCO Corporation).

(3) From the thus obtained absorption spectrum, the maximum absorption wavelength in a range of 300 nm to 600 nm was determined. The results thereof are shown in Table 3 below. It is noted here that, in the below-described Comparative Examples 1-2 to 1-4 and 1-6, since these compounds had a low solubility in water, the measurement was performed using a measurement solution obtained by dissolving each compound in acetonitrile as a solvent. Further, as the absorption spectrum, a corrected absorption spectrum obtained by measuring the absorption spectrum of the solvent itself in advance and deducting this absorption spectrum of the solvent from the absorption spectrum of the measurement solution was used.

TABLE 3

| | Compound | Solubility in 100 parts by mass of water (parts by mass) | Maximum absorption wavelength (nm) |
|---|---|---|---|
| Example 1-1 | Compound 61 | 1.2 | 391 |
| Example 1-2 | Compound 1 | 0.9 | 391 |
| Comparative Example 1-1 | Compound 101 | 0.8 | 270 |
| Comparative Example 1-2 | Compound 102 | <0.1 | 325 |
| Comparative Example 1-3 | Compound 103 | <0.1 | 253 |
| Comparative Example 1-4 | Compound 104 | <0.1 | 460 |
| Comparative Example 1-5 | Compound 105 | ≥50 | 371 |
| Comparative Example 1-6 | Compound 106 | <0.1 | 391 |

II. Evaluation of Compositions

Production Example 1: Aqueous Solution No. 1 of Water-Soluble Polymer Having Photosensitive Groups and Hydroxy Groups To a reaction flask containing 1,000 parts of ion-exchanged water, 138 parts of NICHIGO G-Polymer OKS-1083 (saponification degree=99; manufactured by The Nippon Synthetic Chemical Industry Co., Ltd.) was slowly added as a hydroxy group-containing polymer, and this mixture was stirred for 1 hour and then heated to 90° C. so as to completely dissolve the polymer. The resultant was cooled to 40° C., and formylstyryl pyridinium as a photosensitive group donor in an amount equivalent to 2% by mole of hydroxy groups and 0.7 parts of phosphoric acid were added thereto, followed by 2 hours of continuous stirring at 40° C. The resulting solution was cooled to room temperature, and ion-exchanged water was subsequently added thereto such that the solid content was adjusted to 15%. This solution was further stirred for 1 hour at room temperature and then filtered through a 5-μm filter, after which ion-exchanged water was further added to adjust the solid content to be 10% by mass, whereby an aqueous solution No. 1 of water-soluble polymer having photosensitive groups and hydroxy groups was obtained.

Production Example 2: Aqueous Solution No. 1 of Water-Soluble Polymer Having Radical Polymerizable Groups and Hydroxy Groups To a reaction flask containing 1,000 parts of ion-exchanged water, 138 parts of GOHSENOL GL-05 (saponification degree=87; manufactured by The Nippon Synthetic Chemical Industry Co., Ltd.) was slowly added as a hydroxy group-containing polymer, and this mixture was stirred for 1 hour and then heated to 90° C. so as to completely dissolve the polymer. The resultant was cooled to 50° C., and N-methylolacrylamide as a photosensitivity-imparting agent in an amount equivalent to 2% by mole of hydroxy groups and 0.1 parts of p-toluenesulfonic acid were added thereto, followed by 3 hours of continuous stirring at 50° C. The resulting solution was cooled to room temperature, ion-exchanged water was added thereto, and this solution was further stirred for 1 hour at room temperature and subsequently filtered through a 5-μm filter, after which ion-exchanged water was further added to adjust the solid content to be 10% by mass, whereby an aqueous solution No. 1 of water-soluble polymer having radical polymerizable groups and hydroxy groups was obtained.

Production Example 3: Aqueous Solution No. 1 of Polyvinyl Alcohol Water-Soluble Polymer To 90.0 g of ion-exchanged water under stirring, 10.0 g of a polyvinyl alcohol GOHSENOL NL-05 (saponification degree=98; manufactured by The Nippon Synthetic Chemical Industry Co., Ltd.) was slowly added, and the resultant was stirred for 1 hour at room temperature. Subsequently, the internal temperature was adjusted to be 85° C. to 90° C., and the stirring was continued for 2 hours. After confirming that the polyvinyl alcohol was dissolved, the resulting solution was cooled to room temperature and then filtered through a 1-pin filter, after which ion-exchanged water was further added to adjust the solid content to be 10% by mass, whereby an aqueous solution No. 1 of polyvinyl alcohol water-soluble polymer was obtained.

Production Example 4: Aqueous Solution No. 2 of Polyvinyl Alcohol Water-Soluble Polymer To 90.0 g of ion-exchanged water under stirring, 10.0 g of GOHSENX Z-200 (saponification degree=99; manufactured by The Nippon Synthetic Chemical Industry Co., Ltd.) was slowly added, and the resultant was stirred for 1 hour at room temperature. Subsequently, the internal temperature was adjusted to be 85° C. to 90° C., and the stirring was continued for 2 hours. After confirming that GOHSENX Z-200 was dissolved, the resulting solution was cooled to room temperature and then filtered through a 1-μm filter, whereby an aqueous solution No. 2 of polyvinyl alcohol water-soluble polymer was obtained.

Production Example 5: Aqueous Polypynolidone Solution No. 1

To 90.0 g of ion-exchanged water under stirring, 10.0 g of K90 (manufactured by Nippon Shokubai Co., Ltd.) was slowly added as a polyvinylpyrrolidone, and the resultant was stirred for 1 hour at room temperature. Subsequently, the internal temperature was adjusted to be 85° C. to 90° C., and the stirring was continued for 2 hours. After confirming that the polyvinylpyrrolidone was dissolved, the resulting solution was cooled to room temperature and then filtered through a 1-μm filter, whereby an aqueous polypyrrolidone solution No. 1 was obtained.

Examples 2-1 to 2-38 and Comparative Examples 2-1 to 2-16

In accordance with the respective formulations shown in Tables 4 to 9, compositions were obtained by stirring the respective components at room temperature for 1 hour. In these Tables, the numerical values of the formulations each indicate an amount in parts by mass. Further, the composition of Example 2-13 contains 400 parts by mass of the aqueous solution No. 1 of water-soluble polymer having radical polymerizable groups and hydroxy groups (solid content: 10% by mass) and 400 parts by mass of the aqueous solution No. 2 of polyvinyl alcohol-modified water-soluble polymer (solid content: 10% by mass) and, therefore, contains 720 parts by mass of water derived from these polymer aqueous solutions. Moreover, the symbols used for the respective components in these Tables indicate the below-described components. The thus obtained compositions of Examples and Comparative Examples were evaluated by the procedures described below.

1. Compatibility (Compatibility with Composition)

For each composition, the condition immediately after the 1-hour stirring was visually checked and evaluated based on the following criteria.

○: transparent and uniform to slightly turbid

Δ: turbid x: not compatible, observed with gelation or insoluble matter

It can be judged that: an evaluation of ○ means that the radical polymerization initiator was sufficiently dissolved or dispersed in the composition; and an evaluation of Δ means that the radical polymerization initiator was dispersed and had excellent compatibility with the composition. Further, it can be judged that an evaluation of x means that the radical polymerization initiator aggregated or precipitated in the composition and thus had a low solubility in the composition.

2. Curability (Sensitivity)

The compositions of Examples and Comparative Examples were each applied onto a glass substrate using an applicator and exposed to light of various wavelengths (500 mJ/cm$^2$), and the thus obtained test pieces with no surface stickiness were subsequently immersed in 23° C. ion-exchanged water for 30 seconds and then dried at 120° C., after which the change in film thickness was checked (the coating film which was only exposed and dried without being immersed in water had a film thickness of 10 μm). This curing test was performed using, as light sources, a high-pressure mercury lamp (17 mW/cm$^2$ in terms of a wavelength of 365 nm) and LED light sources of various wavelengths (365 nm, 385 nm, 395 nm, 405 nm, 420 nm, 450 nm, and 470 nm).

⊚: After the test piece was immersed in water and dried, the change in film thickness was 5% or less ○: After the test piece was immersed in water and dried, the change in film thickness was less than 20%

Δ: After the test piece was immersed in water and dried, the change in film thickness was 20% or higher, but a film remained.

x: No film remained after the test piece was immersed in water and dried.

It can be judged that an evaluation of ⊚ or ○ means that the test composition was sufficiently cured and thus had a high sensitivity. Further, it can be judged that the curability was superior, and the sensitivity was higher in the order of ⊚, ○ and Δ. Meanwhile, it can be judged that an evaluation of x means that the test composition was not sufficiently cured and thus had a low sensitivity.

(Radical Polymerization Initiators: Components A and B)

A-1: compound obtained in Example 1-1 (compound represented by Formula (61))

A-2: compound obtained in Example 1-2 (compound represented by Formula (1))

A-3: compound represented by the following Formula (201)

B-1: compound of Comparative Example 1-1 (compound represented by Formula (101))

B-2: compound of Comparative Example 1-2 (compound represented by Formula (102))

B-3: compound of Comparative Example 1-3 (compound represented by Formula (103))

B-4: compound of Comparative Example 1-4 (compound represented by Formula (104))

B-5: compound of Comparative Example 1-5 (compound represented by Formula (105))

B-6: compound of Comparative Example 1-6 (compound represented by Formula (106))

(201)

(Radical Polymerizable Compounds: Component C)

C-1: NK ESTER A-GLY-20E (alkylene oxide-modified acrylate; manufactured by Shin-Nakamura Chemical Co., Ltd.)

C-2: NK ECONOMERA-PG5054E (alkylene oxide-modified acrylate; manufactured by Shin-Nakamura Chemical Co., Ltd.)

C-3: FAM-301 (polyfunctional acrylamide compound; manufactured by FUJIFILM Corporation)

C-4: acryloylmorpholine

C-5: hydroxyethylacrylamide

C-6: aqueous solution No. 1 of water-soluble polymer having radical polymerizable groups and hydroxy groups, which was obtained in Production Example 2

(Polymerizable Compound: Photosensitive Group-Containing Resin: Component D)

D-1: aqueous solution No. 1 of water-soluble polymer having photosensitive groups and hydroxy groups, which was obtained in Production Example 1

(Polymers Having No Polymerizable Group: Non-photosensitive Resins: Component E)

E-1: aqueous solution No. 1 of polyvinyl alcohol-modified water-soluble polymer

E-2: aqueous solution No. 2 of polyvinyl alcohol-modified water-soluble polymer

E-3: polypyrrolidone aqueous solution No. 1

(Solvent: Component F)

F-1: water (Colorant: Compound G)

G-1: BONJET BLACK CW-1 (modified carbon black self-dispersion, concentration=20%; manufactured by Orient Chemical Industries Co., Ltd.)

G-2: MICROPIGMO WMRD-5 (Pigment Red 17 resin dispersion, concentration=20%; manufactured by Orient Chemical Industries Co., Ltd.)

G-3: MICROPIGMO WMGN-5 (Pigment Green 7 resin dispersion, concentration=21%; manufactured by Orient Chemical Industries Co., Ltd.)

G-4: MICROPIGMO WMBE-5 (Pigment Blue 15:6 resin dispersion, concentration=20%; manufactured by Orient Chemical Industries Co., Ltd.)

(Additives: Component H)

H-1: MEGAFACE F-444 (fluorine-based leveling agent; manufactured by DIC Corporation)

H-2: ORGATIX ZC-126 (aqueous zirconyl chloride solution: component concentration=30%, Zr content=11%; manufactured by Matsumoto Fine Chemical Co., Ltd.)

H-3: ORGATIX WS-700 (organic titanium-modified polyethylene imine, an aqueous solution having a component concentration of 10%; manufactured by Matsumoto Fine Chemical Co., Ltd.)

H-4: compound represented by the following Formula (111) (thioxanthone)

H-5: compound represented by the following Formula (112) (isopropylthioxanthone)

H-6: compound represented by the following Formula (113) (diethylthioxanthone)

(111)

(112)

(113)

TABLE 4

|  |  |  | Example | | | | | | | | | |
|---|---|---|---|---|---|---|---|---|---|---|---|---|
|  |  |  | 2-1 | 2-2 | 2-3 | 2-4 | 2-5 | 2-6 | 2-7 | 2-8 | 2-9 | 2-10 |
| Components A and B |  | A-1 | 1 | 2 | 5 | — | — | — | 2 | — | 2 | — |
|  |  | A-2 | — | — | — | 1 | 2 | 5 | — | 2 | — | 2 |
|  |  | A-3 | — | — | — | — | — | — | — | — | — | — |
|  |  | B-1 | — | — | — | — | — | — | — | — | — | — |
|  |  | B-2 | — | — | — | — | — | — | — | — | — | — |
|  |  | B-3 | — | — | — | — | — | — | — | — | — | — |
|  |  | B-4 | — | — | — | — | — | — | — | — | — | — |
|  |  | B-5 | — | — | — | — | — | — | 5 | 5 | 5 | 5 |
|  |  | B-6 | — | — | — | — | — | — | — | — | — | — |
| Component C |  | C-1 | 49 | 49 | 47 | 49 | 49 | 47 | 47 | 47 | — | — |
|  |  | C-2 | — | — | — | — | — | — | — | — | 47 | 47 |
|  |  | C-3 | — | — | — | — | — | — | — | — | — | — |
|  |  | C-4 | — | — | — | — | — | — | — | — | 47 | 47 |
|  |  | C-5 | 49 | 49 | 47 | 49 | 49 | 47 | 47 | 47 | — | — |
|  |  | C-6 | — | — | — | — | — | — | — | — | — | — |
| Resin component | Component D | D-1 | — | — | — | — | — | — | — | — | — | — |
|  | Component E | E-1 | — | — | — | — | — | — | — | — | — | — |
|  |  | E-2 | — | — | — | — | — | — | — | — | — | — |
|  |  | E-3 | — | — | — | — | — | — | — | — | — | — |
| Component F |  | F-1 | 100 | 100 | 100 | 100 | 100 | 100 | 100 | 100 | 100 | 100 |
| Component G |  | G-1 | — | — | — | — | — | — | — | — | — | — |
|  |  | G-2 | — | — | — | — | — | — | — | — | — | — |
|  |  | G-3 | — | — | — | — | — | — | — | — | — | — |
|  |  | G-4 | — | — | — | — | — | — | — | — | — | — |
| Component H |  | H-1 | — | — | — | — | — | — | — | — | — | — |
|  |  | H-2 | — | — | — | — | — | — | — | — | — | — |
|  |  | H-3 | — | — | — | — | — | — | — | — | — | — |
|  |  | H-4 | — | — | — | — | — | — | — | — | — | — |
|  |  | H-5 | — | — | — | — | — | — | — | — | — | — |
|  |  | H-6 | — | — | — | — | — | — | — | — | — | — |
| Evaluation | Compatibility |  | ○ | ○ | ○ | ○ | ○ | △ | ○ | ○ | ○ | ○ |
|  | Curability (sensitivity) | High-pressure mercury lamp | ○ | ◎ | ◎ | ○ | ◎ | ◎ | ◎ | ◎ | ◎ | ◎ |
|  |  | LED 365 nm | ○ | ◎ | ◎ | ○ | ◎ | ◎ | ◎ | ◎ | ◎ | ◎ |
|  |  | LED 385 nm | ○ | ○ | ○ | ○ | ○ | ○ | ○ | ○ | ○ | ○ |
|  |  | LED 395 nm | ○ | ○ | ○ | ○ | ○ | ○ | ○ | ○ | ○ | ○ |
|  |  | LED 405 nm | ○ | ○ | ○ | ○ | ○ | ○ | ○ | ○ | ○ | ○ |
|  |  | LED 420 nm | ○ | ○ | ○ | ○ | ○ | ○ | ○ | ○ | ○ | ○ |
|  |  | LED 450 nm | △ | △ | △ | △ | △ | △ | ○ | ○ | ○ | ○ |
|  |  | LED 470 nm | △ | △ | △ | △ | △ | ○ | ○ | ○ | ○ | ○ |

TABLE 5

|  |  |  | Example | | | | | | | | | |
|---|---|---|---|---|---|---|---|---|---|---|---|---|
|  |  |  | 2-11 | 2-12 | 2-13 | 2-14 | 2-15 | 2-16 | 2-17 | 2-18 | 2-19 | 2-20 |
| Components A and B |  | A-1 | 2 | — | 2 | — | 2 | 2 | — | 2 | — | 2 |
|  |  | A-2 | — | 2 | — | 2 | — | — | 2 | — | 2 | — |
|  |  | A-3 | — | — | — | — | — | — | — | — | — | — |
|  |  | B-1 | — | — | — | — | — | — | — | — | — | — |
|  |  | B-2 | — | — | — | — | — | — | — | — | — | — |
|  |  | B-3 | — | — | — | — | — | — | — | — | — | — |
|  |  | B-4 | — | — | — | — | — | — | — | — | — | — |
|  |  | B-5 | — | — | — | — | — | — | — | — | — | — |
|  |  | B-6 | — | — | — | — | — | — | — | — | — | — |
| Component C |  | C-1 | — | — | — | — | — | — | — | 10 | — | — |
|  |  | C-2 | — | — | — | — | — | — | — | 10 | — | — |
|  |  | C-3 | 47 | 47 | 10 | 10 | 10 | 5 | 5 | — | 10 | 10 |
|  |  | C-4 | — | — | — | — | — | — | — | — | — | — |
|  |  | C-5 | 47 | 47 | 10 | 10 | 10 | 5 | 5 | — | 10 | 10 |
|  |  | C-6 | — | — | 400 | 400 | 400 | 400 | 400 | 400 | — | — |
| Resin component | Component D | D-1 | — | — | — | — | — | — | — | — | 400 | — |
|  | Component E | E-1 | — | — | — | — | — | — | — | — | 400 | — |
|  |  | E-2 | — | — | 400 | 400 | — | — | — | 400 | — | 800 |
|  |  | E-3 | — | — | — | — | 400 | — | — | — | — | — |
| Component F |  | F-1 | 100 | 100 | — | — | — | — | — | — | — | — |
| Component G |  | G-1 | — | — | — | — | — | — | — | — | — | — |
|  |  | G-2 | — | — | — | — | — | — | — | — | — | — |
|  |  | G-3 | — | — | — | — | — | — | — | — | — | — |
|  |  | G-4 | — | — | — | — | — | — | — | — | — | — |

TABLE 5-continued

|  |  | Example |  |  |  |  |  |  |  |  |  |
|---|---|---|---|---|---|---|---|---|---|---|---|
|  |  | 2-11 | 2-12 | 2-13 | 2-14 | 2-15 | 2-16 | 2-17 | 2-18 | 2-19 | 2-20 |
| Component H | H-1 | — | — | 0.05 | 0.05 | 0.05 | 0.05 | 0.05 | 0.05 | 0.05 | 0.05 |
|  | H-2 | — | — | — | — | — | — | — | 0.5 | — | 0.5 |
|  | H-3 | — | — | 1 | 1 | 1 | 1 | 1 | 1 | 1 | — |
|  | H-4 | — | — | — | — | — | — | — | — | — | — |
|  | H-5 | — | — | — | — | — | — | — | — | — | — |
|  | H-6 | — | — | — | — | — | — | — | — | — | — |
| Evaluation | Compatibility | ○ | ○ | ○ | ○ | ○ | ○ | ○ | ○ | ○ | ○ |
| Curability (sensitivity) | High-pressure mercury lamp | ◎ | ◎ | ○ | ○ | ○ | ○ | ○ | ○ | ○ | ○ |
|  | LED 365 nm | ◎ | ◎ | ○ | ○ | ○ | ○ | ○ | ○ | ○ | ○ |
|  | LED 385 nm | ○ | ○ | ○ | ○ | ○ | ○ | ○ | ○ | ○ | ○ |
|  | LED 395 nm | ○ | ○ | ○ | ○ | ○ | ○ | ○ | ○ | ○ | ○ |
|  | LED 405 nm | ○ | ○ | ○ | ○ | ○ | ○ | ○ | ○ | ○ | ○ |
|  | LED 420 nm | ○ | ○ | ○ | ○ | ○ | ○ | ○ | ○ | ○ | ○ |
|  | LED 450 nm | ○ | ○ | ○ | ○ | ○ | ○ | ○ | ○ | ○ | ○ |
|  | LED 470 nm | ○ | ○ | ○ | ○ | ○ | ○ | ○ | ○ | ○ | ○ |

TABLE 6

|  |  | Example |  |  |  |  |  |  |  |  |  |  |
|---|---|---|---|---|---|---|---|---|---|---|---|---|
|  |  |  | 2-21 | 2-22 | 2-23 | 2-24 | 2-25 | 2-26 | 2-27 | 2-28 | 2-29 | 2-30 |
| Components A and B |  | A-1 | — | 2 | — | 2 | — | — | 2 | 2 | 2 | 2 |
|  |  | A-2 | 2 | — | 2 | — | 2 | 2 | — | — | — | — |
|  |  | A-3 | — | — | — | — | — | — | — | — | — | — |
|  |  | B-1 | — | — | — | — | — | — | — | — | — | — |
|  |  | B-2 | — | — | — | — | — | — | — | — | — | — |
|  |  | B-3 | — | — | — | — | — | — | — | — | — | — |
|  |  | B-4 | — | — | — | — | — | — | — | — | — | — |
|  |  | B-5 | — | 5 | 5 | 5 | 5 | 5 | 5 | 5 | 5 | 5 |
|  |  | B-6 | — | — | — | — | — | — | — | — | — | — |
| Component C |  | C-1 | — | — | — | — | — | — | — | — | — | — |
|  |  | C-2 | — | — | — | 5 | 5 | — | — | — | — | — |
|  |  | C-3 | 10 | 10 | 10 | 5 | 5 | 10 | 10 | 10 | 10 | 10 |
|  |  | C-4 | — | — | — | 5 | 5 | — | — | — | — | — |
|  |  | C-5 | 10 | 10 | 10 | 5 | 5 | 10 | 10 | 10 | 10 | 10 |
|  |  | C-6 | — | 400 | 400 | 400 | 400 | — | 800 | — | — | 400 |
| Resin component | Component D | D-1 | — | — | — | — | — | — | — | — | 800 | — |
|  | Component E | E-1 | — | — | — | — | — | — | — | 800 | — | — |
|  |  | E-2 | 800 | — | — | — | — | — | — | — | — | 400 |
|  |  | E-3 | — | — | — | — | — | — | — | — | — | — |
| Component F |  | F-1 | — | — | — | — | — | — | — | — | — | — |
| Component G |  | G-1 | — | — | — | — | — | — | 50 | — | — | — |
|  |  | G-2 | — | — | — | — | — | — | — | 50 | — | — |
|  |  | G-3 | — | — | — | — | — | — | — | — | 50 | — |
|  |  | G-4 | — | — | — | — | — | — | — | — | — | 50 |
| Component H |  | H-1 | 0.05 | 0.05 | 0.05 | 0.05 | 0.05 | 0.05 | 0.05 | 0.05 | 0.05 | 0.05 |
|  |  | H-2 | 0.5 | — | — | — | — | 0.5 | — | 0.5 | — | 0.5 |
|  |  | H-3 | — | 1 | 1 | 1 | 1 | 1 | 1 | — | 1 | 1 |
|  |  | H-4 | — | — | — | — | — | — | — | — | — | — |
|  |  | H-5 | — | — | — | — | — | — | — | — | — | — |
|  |  | H-6 | — | — | — | — | — | — | — | — | — | — |
| Evaluation | Compatibiity |  | ○ | ○ | ○ | ○ | ○ | ○ | ○ | ○ | ○ | ○ |
| Curability (sensitivity) | High-pressure mercury lamp |  | ○ | ◎ | ◎ | ◎ | ◎ | ◎ | ◎ | ◎ | ◎ | ◎ |
|  | LED 365 nm |  | ○ | ◎ | ◎ | ◎ | ◎ | ○ | ◎ | ◎ | ◎ | ◎ |
|  | LED 385 nm |  | ○ | ◎ | ◎ | ◎ | ◎ | ○ | ○ | ○ | ○ | ○ |
|  | LED 395 nm |  | ○ | ◎ | ◎ | ◎ | ◎ | ○ | ○ | ○ | ○ | ○ |
|  | LED 405 nm |  | ○ | ○ | ○ | ○ | ○ | ○ | ○ | ○ | ○ | ○ |
|  | LED 420 nm |  | ○ | ○ | ○ | ○ | ○ | ○ | ○ | ○ | ○ | ○ |
|  | LED 450 nm |  | ○ | ○ | ○ | ○ | ○ | ○ | ○ | ○ | ○ | ○ |
|  | LED 470 nm |  | ○ | ○ | ○ | ○ | ○ | ○ | ○ | ○ | ○ | ○ |

TABLE 7

| | | | Example | | | | | | | |
|---|---|---|---|---|---|---|---|---|---|---|
| | | | 2-31 | 2-32 | 2-33 | 2-34 | 2-35 | 2-36 | 2-37 | 2-38 |
| Components A and B | | A-1 | — | — | 1 | 2 | 5 | — | 2 | — |
| | | A-2 | — | — | — | — | — | 2 | — | 2 |
| | | A-3 | 1 | 1 | — | — | — | — | — | — |
| | | B-1 | — | — | — | — | — | — | — | — |
| | | B-2 | — | — | — | — | — | — | — | — |
| | | B-3 | — | — | — | — | — | — | — | — |
| | | B-4 | — | — | — | — | — | — | — | — |
| | | B-5 | 5 | 5 | — | — | — | — | 5 | 5 |
| | | B-6 | — | — | — | — | — | — | — | — |
| Component C | | C-1 | 49 | — | — | — | — | — | — | — |
| | | C-2 | — | — | — | — | — | — | — | — |
| | | C-3 | — | 5 | 50 | 50 | 50 | 50 | 50 | 50 |
| | | C-4 | — | — | 50 | 50 | 50 | 50 | 50 | — |
| | | C-5 | 49 | 5 | — | — | — | — | — | 50 |
| | | C-6 | — | 400 | — | — | — | — | — | — |
| Resin component | Component D | D-1 | — | — | — | — | — | — | — | — |
| | Component E | E-1 | — | — | — | — | — | — | — | — |
| | | E-2 | — | — | — | — | — | — | — | — |
| | | E-3 | — | — | — | — | — | — | — | — |
| Component F | | F-1 | 100 | — | — | — | — | — | — | — |
| Component G | | G-1 | — | — | — | — | — | — | — | — |
| | | G-2 | — | — | — | — | — | — | — | — |
| | | G-3 | — | — | — | — | — | — | — | — |
| | | G-4 | — | — | — | — | — | — | — | — |
| Component H | | H-1 | — | 0.05 | — | — | — | — | — | — |
| | | H-2 | — | — | — | — | — | — | — | — |
| | | H-3 | — | 1 | — | — | — | — | — | — |
| | | H-4 | — | — | — | — | — | — | — | — |
| | | H-5 | — | — | — | — | — | — | — | — |
| | | H-6 | — | — | — | — | — | — | — | — |
| Evaluation | Compatibility | | ○ | ○ | ○ | ○ | ○ | ○ | ○ | ○ |
| | Curability (sensitivity) | High-pressure mercury lamp | ◎ | ◎ | ◎ | ◎ | ◎ | ◎ | ◎ | ◎ |
| | | LED 365 nm | ◎ | ◎ | ◎ | ◎ | ◎ | ◎ | ◎ | ◎ |
| | | LED 385 nm | ○ | ○ | ○ | ○ | ○ | ○ | ○ | ○ |
| | | LED 395 nm | ○ | ○ | ○ | ○ | ○ | ○ | ○ | ○ |
| | | LED 405 nm | ○ | ○ | ○ | ○ | ○ | ○ | ○ | ○ |
| | | LED 420 nm | ○ | ○ | ○ | ○ | ○ | ○ | ○ | ○ |
| | | LED 450 nm | ○ | ○ | Δ | ○ | ○ | ○ | ○ | ○ |
| | | LED 470 nm | ○ | ○ | Δ | Δ | ○ | ○ | ○ | ○ |

TABLE 8

| | | | Comparative Example | | | | | | | | | |
|---|---|---|---|---|---|---|---|---|---|---|---|---|
| | | | 2-1 | 2-2 | 2-3 | 2-4 | 2-5 | 2-6 | 2-7 | 2-8 | 2-9 | 2-10 |
| Components A and B | | A-1 | — | — | — | — | — | — | — | — | — | — |
| | | A-2 | — | — | — | — | — | — | — | — | — | — |
| | | A-3 | — | — | — | — | — | — | — | — | — | — |
| | | B-1 | 5 | — | — | — | — | — | 5 | — | 5 | — |
| | | B-2 | — | 5 | — | — | — | — | — | — | — | — |
| | | B-3 | — | — | 5 | — | — | — | 1 | 2 | — | — |
| | | B-4 | — | — | — | 5 | — | — | — | — | — | — |
| | | B-5 | — | — | — | — | 5 | — | — | 5 | 2 | 5 |
| | | B-6 | — | — | — | — | — | 5 | — | — | — | — |
| Component C | | C-1 | 47 | 47 | 47 | 47 | 47 | 47 | 47 | 47 | 47 | — |
| | | C-2 | — | — | — | — | — | — | — | — | — | — |
| | | C-3 | — | — | — | — | — | — | — | — | — | — |
| | | C-4 | — | — | — | — | — | — | — | — | — | — |
| | | C-5 | 47 | 47 | 47 | 47 | 47 | 47 | 47 | 47 | 47 | — |
| | | C-6 | — | — | — | — | — | — | — | — | — | 800 |
| Resin component | Component D | D-1 | — | — | — | — | — | — | — | — | — | — |
| | Component E | E-1 | — | — | — | — | — | — | — | — | — | — |
| | | E-2 | — | — | — | — | — | — | — | — | — | — |
| | | E-3 | — | — | — | — | — | — | — | — | — | — |
| Component F | | F-1 | 100 | 100 | 100 | 100 | 100 | 100 | 100 | 100 | 100 | — |
| Component G | | G-1 | — | — | — | — | — | — | — | — | — | 50 |
| | | G-2 | — | — | — | — | — | — | — | — | — | — |
| | | G-3 | — | — | — | — | — | — | — | — | — | — |
| | | G-4 | — | — | — | — | — | — | — | — | — | — |

TABLE 8-continued

|  |  | Comparative Example | | | | | | | | | |
|---|---|---|---|---|---|---|---|---|---|---|---|
|  |  | 2-1 | 2-2 | 2-3 | 2-4 | 2-5 | 2-6 | 2-7 | 2-8 | 2-9 | 2-10 |
| Component H | H-1 | — | — | — | — | — | — | — | — | — | 0.05 |
|  | H-2 | — | — | — | — | — | — | — | — | — | — |
|  | H-3 | — | — | — | — | — | — | — | — | — | 1 |
|  | H-4 | — | — | — | — | — | — | — | — | — | — |
|  | H-5 | — | — | — | — | — | — | — | — | — | — |
|  | H-6 | — | — | — | — | — | — | — | — | — | — |
| Evaluation Compatibility |  | ◯ | X | ◯ | X | ◯ | X | ◯ | ◯ | ◯ | ◯ |
| Curability (sensitivity) | High-pressure mercury lamp | ◯ | ◯ | ◯ | ◯ | ◯ | ◯ | ◎ | ◯ | ◯ | ◯ |
|  | LED 365 nm | Δ | Δ | Δ | ◯ | ◯ | ◯ | Δ | ◯ | ◯ | Δ |
|  | LED 385 nm | X | X | X | ◯ | ◯ | ◯ | X | Δ | ◯ | Δ |
|  | LED 395 nm | X | X | X | ◯ | ◯ | ◯ | X | Δ | ◯ | Δ |
|  | LED 405 nm | X | X | X | ◯ | ◯ | ◯ | X | Δ | Δ | X |
|  | LED 420 nm | X | X | X | ◯ | ◯ | ◯ | X | Δ | Δ | X |
|  | LED 450 nm | X | X | X | ◯ | Δ | Δ | X | Δ | Δ | X |
|  | LED 470 nm | X | X | X | ◯ | X | Δ | X | X | X | X |

TABLE 9

|  |  |  | Comparative Example | | | | | |
|---|---|---|---|---|---|---|---|---|
|  |  |  | 2-11 | 2-12 | 2-13 | 2-14 | 2-15 | 2-16 |
| Components A and B |  | A-1 | — | — | — | — | — | — |
|  |  | A-2 | — | — | — | — | — | — |
|  |  | A-3 | — | — | — | — | — | — |
|  |  | B-1 | 5 | — | 5 | — | — | — |
|  |  | B-2 | — | — | — | — | — | — |
|  |  | B-3 | — | — | — | — | — | — |
|  |  | B-4 | — | — | — | — | — | — |
|  |  | B-5 | — | 5 | — | 5 | 5 | 5 |
|  |  | B-6 | — | — | — | — | — | — |
| Component C |  | C-1 | — | — | — | 47 | 47 | 47 |
|  |  | C-2 | — | — | — | — | — | — |
|  |  | C-3 | — | — | — | — | — | — |
|  |  | C-4 | — | — | — | — | — | — |
|  |  | C-5 | — | — | — | 47 | 47 | 47 |
|  |  | C-6 | — | — | 400 | — | — | — |
| Resin component | Component D | D-1 | — | 800 | — | — | — | — |
|  | Component E | E-1 | 800 | — | — | — | — | — |
|  |  | E-2 | — | — | 400 | — | — | — |
|  |  | E-3 | — | — | — | — | — | — |
| Component F |  | F-1 | — | — | — | 100 | 100 | 100 |
| Component G |  | G-1 | — | — | — | — | — | — |
|  |  | G-2 | 50 | — | — | — | — | — |
|  |  | G-3 | — | 50 | — | — | — | — |
|  |  | G-4 | — | — | 50 | — | — | — |
| Component H |  | H-1 | 0.05 | 0.05 | 0.05 | 0.05 | 0.05 | 0.05 |
|  |  | H-2 | 0.5 | — | 0.5 | 0.5 | 0.5 | 0.5 |
|  |  | H-3 | — | 1 | 1 | 1 | 1 | 1 |
|  |  | H-4 | — | — | — | 1 | — | — |
|  |  | H-5 | — | — | — | — | 1 | — |
|  |  | H-6 | — | — | — | — | — | 1 |
| Evaluation Compatibility |  |  | ◯ | ◯ | ◯ | X | X | X |
| Curability (sensitivity) | High-pressure mercury lamp |  | Δ | ◯ | Δ | ◯ | ◯ | ◯ |
|  | LED 365 nm |  | Δ | Δ | Δ | ◯ | ◯ | ◯ |
|  | LED 385 nm |  | X | Δ | X | ◯ | ◯ | ◯ |
|  | LED 395 nm |  | X | Δ | X | ◯ | ◯ | ◯ |
|  | LED 405 nm |  | X | X | X | ◯ | ◯ | ◯ |
|  | LED 420 nm |  | X | X | X | Δ | Δ | Δ |
|  | LED 450 nm |  | X | X | X | Δ | Δ | Δ |
|  | LED 470 nm |  | X | X | X | X | X | X |

It was confirmed from Tables 3 to 9 that the compounds A of Examples were excellent in both sensitivity and compatibility with the respective compositions. For example, it was confirmed that these compounds A can also be favorably dissolved or dispersed in a composition containing water as a solvent. From the results of Examples 2-33 to 2-38 that the compounds A of Examples exhibited excellent compatibility with the radical polymerizable compounds and the like having hydrophilic groups such as an acrylamide group and a hydroxy group, it was confirmed that these compounds A can exhibit excellent compatibility with a composition even if the composition contains no solvent.

The compounds A of Examples (Compounds A-1 and A-2) had a maximum absorption wavelength of 380 nm or longer, and it was confirmed that these compounds A can be sufficiently cured and exhibit excellent sensitivity even when they are cured using an exposure light having a wavelength peak of 400 nm or longer. On the other hand, it was confirmed that the compounds of Comparative Examples 1-1 to 1-3, 1-5 and the like sometimes cannot be sufficiently cured using an exposure light having a wavelength peak of 400 nm or longer. Accordingly, the compounds A of Examples were confirmed to have excellent depth curability in that they allow even a deep part of a composition to be cured in a stable manner. Further, it was confirmed that, because of this depth curability, the compounds A of Examples are useful for, for example, curing a colorant-containing composition such as an ink.

From a comparison between Example 2-2 and Example 2-7, it was confirmed that, by using the compound A of these Examples in combination with other radical polymerization initiator, particularly a compound corresponding to the compound I, a composition can be cured with light in a longer wavelength range and imparted with superior sensitivity as compared to a case where the compound A of these Examples was used by itself.

On the other hand, comparing the results of Examples 2-2 and 2-7 with the results of Comparative Examples 2-5 and 2-14 to 2-16, it was confirmed that a sensitivity-improving effect cannot be obtained by using a compound simply having a thioxanthone skeleton in combination with the compound I, while a combination of the compound A and the compound I can exert a sensitivity-improving effect.

Moreover, the compositions of Examples 2-1 to 2-30 had superior transparency as compared to the composition of Comparative Example 2-4. From these results, it was confirmed that excellent color reproduction is attained by using any of the compounds A of Examples, or a radical polymerization initiator or composition that contains the same, as an ink or the like.

The invention claimed is:

1. A radical polymerization initiator, comprising a compound represented by the following, Formula (A):

(A)

[chemical structure]

wherein,
$Z^1$ represents a direct bond, $-NR^{101}-$, $-S-$, $-SO-$, or $-CO-$;
$Z^2$ represents $-C(R^{102})_2-$, $NR^{101}-$, $-O-$, $-S-$, $-SO-$, or $-CO-$;
$R^1$, $R^2$, $R^3$, $R^4$, $R^5$, $R^6$, $R^7$ and $R^8$ each independently represent a hydrogen atom, CN, $NO_2$, a hydroxy group, an alkyl group having 1 to 20 carbon, atoms, an aryl group having 6 to 30 carbon atoms which is optionally substituted with an alkyl group, an arylalkyl group having 7 to carbon atoms which is optionally substituted with an alkyl group, a heterocycle-containing group having 2 to 20 carbon atoms, or a group containing a salt-forming group, which is represented by the following Formula (B1):

$*-L_1-(B)_b$ (B1))

wherein,
$L_1$ represents a direct bond or a (b+1)-valent linking group,
B represents an acidic group salt or a basic group salt,
b represents an integer of 1 to 10, and
the asterisk (*) represents a site of binding with a benzene ring;
at least one of $R^1$, $R^2$, $R^3$, $R^4$, $R^5$, $R^6$, $R^7$ and $R^8$ is the group containing the salt-forming group of Formula (B1);
$R^{101}$ and $R^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms;
one or more hydrogen atoms in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;
one or more methylene groups in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, $-O-$, $-S-$, $-CO-$, $-O-CO-$, $-CO-O-$, $-OCO-O-$, $-O-CO-O-$, $-S-CO-$, $-CO-S-$, $-S-CO-O-$, $-O-CO-S-$, $-CO-NH-$, $-NH-CO-$, $-NH-CO-O-$, $-NR'-$, $-S-S-$, $-SO_2-$, or a combination of groups selected from the above such that oxygen atoms are not arranged adjacent to one another;
adjacent groups of $R^1$ and $R^2$, $R^2$ and $R^3$, $R^3$ and $R^4$, $R^5$ and $R^6$, $R^6$ and $R^7$, and $R^7$ and $R^8$ are optionally bound together to form a ring, and optionally form a fused ring with a benzene ring constituting a three-membered ring in Formula (A); and
R' represents a hydrogen atom or an alkyl group having 1 to 8 carbon atoms,
wherein the radical polymerization initiator satisfies at least one of the following conditions (i) to (iv):
(i) B is the acidic group salt, and a cationic component constituting the acidic group salt is a potassium ion;
(ii) B is the acidic group salt, and a cationic component constituting the acidic group salt is an amine cation;
(iii) $L_1$ is the direct bond, and when B is the acidic group salt, an anionic group constituting the acidic group salt is an anionic group other than a sulfonic acid ion group
(iv) $R^4$ in Formula (A) is the group containing the salt-forming group of Formula (B1).

2. The radical polymerization initiator according to claim 1, wherein the compound has a maximum absorption wavelength of 380 nm or longer in a range of 300 nm to 600 nm.

3. The radical polymerization initiator according to claim 1, wherein a combination of $Z^1$ and $Z^2$ is a combination of $-S-$ and $-CO-$.

4. The radical polymerization initiator according to claim 1, wherein
the radical polymerization initiator satisfies condition (iii), and
B is the acidic group salt.

5. The radical polymerization initiator according to claim 1, wherein
B is the acidic group salt, and
an anionic group constituting the acidic group salt is a carboxylic acid ion group.

6. The radical polymerization initiator according to claim 1, wherein the compound has a solubility of not less than 0.5 parts by mass in 100 parts by mass of water.

7. The radical polymerization initiator according to claim 1, further comprising a compound represented by the following Formula (1):

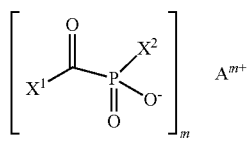

(I)

wherein,
represents an aryl group having 6 to 15 carbon atoms which optionally has a substituent;
$X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms which optionally has a substituent;
$A^{m+}$ represents, an m-valent cationic component;
m represents a number of 1 to 3;
one or more hydrogen atoms in the aryl group used as $X^1$ and $X^2$ and the alkyl group or alkoxy group used as $X^2$ are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;
one or more methylene groups in the aryl group used as $X^1$ and $X^2$ and the alkyl group or alkoxy group used as $X^2$ are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another; and
R' represents a hydrogen atom or an alkyl group having 1 to 8 carbon atoms.

8. A composition comprising:
a compound represented by the following Formula (A):

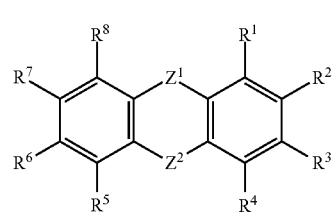

(A)

wherein,
$Z^1$ represents a direct bond, —NR$^{101}$—, —O—, —S—, —SO—, or —CO—;
$Z^2$ represents —C(R$^{102}$)$_2$—, N—R$^{101}$—, —O—, —S—, —SO—, or —CO—;
$R^1$, $R^2$, $R^3$, $R^4$, $R^5$, $R^6$, $R^7$ and $R^8$ each independently represent a hydrogen atom, CN, NO$_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group, which is represented by the following Formula (B1):

*-L$_1$-(-B)$_b$ (B1)

wherein,
$L_1$ represents a direct bond or a (b+1)-valent linking group,
B represents an, acidic group salt or a basic group salt,
b represents an integer of 1 to 10, and
the asterisk (*) represents a site of binding with, a benzene ring);
at least one of $R^1$, $R^2$, $R^3$, $R^4$, $R^5$, $R^6$, $R^7$ and $R^8$ is the group containing the salt-forming group of Formula (B1);
$R^{101}$ and $R^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms;
one or more hydrogen atoms in the alkyl group, the aryl group optionally substituted with, an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with an ethylenically unsaturated group, a halogen atom, an acyl group, an acyloxy group, a substituted amino group, a sulfonamide group, a sulfonyl group, a carboxyl group, a cyano group, a sulfa group, a hydroxy group, a nitro group, a mercapto group, an imide group, a carbamoyl group, a phosphonate group, or a phosphate group;
one or more methylene groups in the alkyl group, the aryl group optionally substituted with an alkyl group, the arylalkyl group optionally substituted with an alkyl group, and the heterocycle-containing, group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, —O—, —S—, —CO—, —O—CO—, —OO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another;

adjacent groups of R$^1$ and R$^2$, R$^2$ and R$^3$, R$^3$ and R$^4$, R$^5$ and R$^6$, R$^6$ and R$^7$, and R$^7$ and R$^8$ are optionally bound together to form a ring, and optionally form a fused ring with a benzene ring constituting a three-membered ring in Formula (A); and R' represents a hydrogen atom or an alkyl group having 1 to 8 carbon atoms, a radical polymerizable compound, wherein the composition satisfies at least one of the following conditions (i) to (iv):

(i) B is the acidic group salt, and a cationic component constituting the acidic group salt is a potassium ion;

(ii) B is the acidic group salt, and a cationic component constituting the acidic group salt is an amine cation;

(iii) L$_1$ is the direct bond, and when B is the acidic group salt, an anionic group constituting the acidic group salt is an anionic group other than a sulfonic acid ion group (iv) R$^4$ in Formula (A) is the group containing the salt-forming group of Formula (B1).

9. The composition according to claim 8, further comprising a solvent that contains water.

10. The composition according, to claim 8, further comprising a compound represented by the following Formula (I):

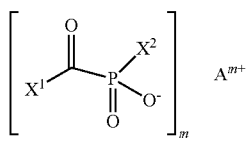

wherein,

X$^1$ represents an aryl group having 6 to 15 carbon atoms which optionally has a substituent;

X$^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms which optionally has a substituent;

A$^{m+}$ represents an m-valent cationic component;

m represents a number of 1 to 3;

one or more hydrogen atoms in the aryl group used as X$^1$ and X$^2$ and the alkyl group or alkoxy group used as X$^2$ are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;

one or more methylene groups in the aryl group used as X$^1$ and X$^2$ and the alkyl group or alkoxy group used as X$^2$ are optionally substituted with a carbon-carbon double bond, —O—, —S—, —CO—, —O—CO—, —OO—, —OCO—O—, —O—CO—O—, —S—CO—, —CO—S—, —S—CO—O—, —O—CO—S—, —CO—NH—, —NH—CO—, —NH—CO—O—, —S—S—, —SO$_2$—, or a combination of groups selected from the above such that oxygen atoms are not arranged adjacent to one another; and R' represents a hydrogen atom or an alkyl group having 1 to 8 carbon atoms.

11. A cured product, comprising the composition according to claim 8.

12. A method of producing a cured product, the method comprising the step of irradiating the composition according to claim 8 with light.

13. A compound represented by the following Formula (A):

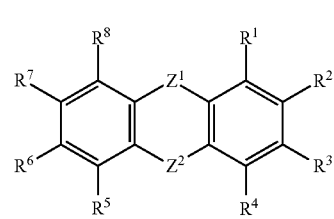

wherein,

Z$^1$ represents a direct bond, —NR$^{101}$, —O—, —S—, —SO—, or —CO—;

Z$^2$ represents —C(R$^{102}$)$_2$—, —NR$^{101}$—, —O—, —S—, —SO—, or —CO—;

R$^1$, R$^2$, R$^3$, R$^4$, R$^5$, R$^6$, R$^7$ and R$^8$ each independently represent a hydrogen atom, CN, NO$_2$, a hydroxy group, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, a heterocycle-containing group having 2 to 20 carbon atoms, or a group containing a salt-forming group, which is represented by the following Formula (B1):

*-L$_1$-(-B)$_b$    (B1)

wherein,

L$_1$ represents a direct bond or a (b+1)-valent linking group,

B represents an acidic group salt or a basic group salt, b represents an integer of 1 to 10, and the asterisk (*) represents a site of binding with a benzene ring;

at least one of R$^1$, R$^2$, R$^3$, R$^4$, R$^5$, R$^6$, R$^7$ and R$^8$ is the group containing salt-forming group of Formula (B1);

R$^{101}$ and R$^{102}$ each independently represent a hydrogen atom, an alkyl group having 1 to 20 carbon atoms, an aryl group having 6 to 30 carbon atoms which is optionally substituted with an alkyl group, an arylalkyl group having 7 to 30 carbon atoms which is optionally substituted with an alkyl group, or a heterocycle-containing group having 2 to 20 carbon atoms;

one or more hydrogen atoms in the alkyl group, the aryl group optionally substituted with an alkyl group, the arylalkyl group optionally substituted with an alkyl group, and the heterocycle-containing group, which groups are used as R$^1$, R$^2$, R$^3$, R$^4$, R$^5$, R$^6$, R$^7$ and R$^8$ and R$^{101}$ and R$^{102}$, are optionally substituted with an ethylenically unsaturated group, a halogen atom, an acyl group, an acyloxy group, a substituted amino group, a sulfonamide group, a sulfonyl group, a carboxyl group, a cyano group, a sulfo group, a hydroxy group, a nitro group, a mercapto group, an imide group, a carbamoyl group, a phosphonate group, or a phosphate group;

one or more methylene groups in the alkyl group, the aryl group optionally substituted with an alkyl group, the arylalkyl group optionally substituted with an alkyl group, and the heterocycle-containing group, which groups are used as $R^1$, $R^2$, $R^3$, $R^4$, $R^5$, $R^6$, $R^7$ and $R^8$ and $R^{101}$ and $R^{102}$, are optionally substituted with a carbon-carbon double bond, —O—, —S—, —CO—, —O—CO—, —CO—O—, —OCO—O—, —O—CO—O—, —S—CO—, —CO—S—, —S—CO—O—, —O—CO—S—, —CO—NH—, —NH—CO—, —NH—CO—O—, —NR'—, —S—S—, —SO$_2$—, or a combination of groups selected from the above such that oxygen atoms are not arranged adjacent to one another;

adjacent groups of $R^1$ and $R^2$, $R^2$ and $R^3$, $R^3$ and $R^4$, $R^5$ and $R^6$, $R^6$ and $R^7$, and $R^7$ and $R^8$ are optionally bound together to form a ring, and optionally form a fused ring with a benzene ring constituting a three-membered ring in Formula (A); and R' represents a hydrogen atom or an alkyl group having 1 to 8 carbon atoms, wherein the compound satisfies at least one of the following conditions (i) to (iv);

(i) B is the acidic group salt, and a cationic component constituting the acidic group salt is a potassium ion;
(ii) B is the acidic group salt, and a cationic component constituting the acidic group salt is an amine cation;
(iii) $L_1$ is the direct bond, and when B is the acidic group salt, an anionic group constituting the acidic group salt is an anionic group other than a sulfonic acid ion group;
(iv) $R^4$ in Formula (A) is the group containing the salt-forming group of Formula (B1).

14. The compound according to claim 13, wherein the compound satisfies condition (iii), a combination of $Z^1$ and $Z^2$ is a combination of —S— and —CO—,
B is the acidic group salt, and
an anionic group constituting the acidic group salt is a carboxylic acid ion group.

15. The compound according to claim 13, wherein the compound satisfies condition (ii), and the amine cation is represented by the following Formula (C2), Formula (C3) or Formula (C4):

$$N^+H_2Y^1Y^2 \qquad (C2)$$

$$N^+HY^1Y^2Y^3 \qquad (C3)$$

$$N^+Y^1Y^2Y^3Y^4 \qquad (C4)$$

wherein
$Y^1$, $Y^2$, $Y^3$ and $Y^4$ each independently represents a hydroxy group, an alkyl group having 1 to 6 carbon atoms, an alkenyl group having 2 to 6 carbon atoms, an aryl group having 6 to 15 carbon atoms, or an arylalkyl group having 7 to 13 carbon atoms;
the hydrogen atoms in the groups represented by $Y^1$, $Y^2$, $Y^3$ and $Y^4$ may each be substituted with a hydroxy group; the methylene groups in the groups represented by $Y^1$, $Y^2$, $Y^3$ and $Y^4$ may each be substituted with an oxygen atom or —N$^+$H—; and two or more of $Y^1$, $Y^2$, $Y^3$ and $Y^4$ may be bound together to form a ring; and
one or more hydrogen atoms in the groups represented by $Y^1$, $Y^2$, $Y^3$ and $Y^4$ are substituted with hydroxy groups, in two or more of $Y^1$, $Y^2$, $Y^3$ and $Y^4$.

16. A method of generating a radical, wherein the method comprises irradiating a radical polymerization initiator according to claim 1 with light.

* * * * *